(12) United States Patent
Jalagam et al.

(10) Patent No.: US 12,275,720 B2
(45) Date of Patent: Apr. 15, 2025

(54) SMALL MOLECULE INHIBITORS OF GALECTIN-3

(71) Applicant: BRISTOL MYERS SQUIBB, Princeton, NJ (US)

(72) Inventors: Prasada Rao Jalagam, Bangalore (IN); Satheesh Kesavan Nair, Bangalore (IN); Susheel Jethanand Nara, Mumbai (IN); Manoranjan Panda, Yelahanka New Town (IN); Pratik Devasthale, Plainsboro, NJ (US); Alicia Regueiro-Ren, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 207 days.

(21) Appl. No.: 17/921,653

(22) PCT Filed: May 4, 2021

(86) PCT No.: PCT/US2021/030540
§ 371 (c)(1),
(2) Date: Oct. 27, 2022

(87) PCT Pub. No.: WO2021/226002
PCT Pub. Date: Nov. 11, 2021

(65) Prior Publication Data
US 2023/0192672 A1 Jun. 22, 2023

Related U.S. Application Data

(60) Provisional application No. 63/020,041, filed on May 5, 2020.

(51) Int. Cl.
*C07H 19/056* (2006.01)
*C07D 405/14* (2006.01)
*C07D 471/04* (2006.01)

(52) U.S. Cl.
CPC ......... *C07D 405/14* (2013.01); *C07D 471/04* (2013.01); *C07H 19/056* (2013.01); *C07B 2200/07* (2013.01)

(58) Field of Classification Search
None
See application file for complete search history.

(56) References Cited

FOREIGN PATENT DOCUMENTS

WO WO-2018209276 A1 * 11/2018 ......... A61K 31/4439

* cited by examiner

*Primary Examiner* — Traviss C McIntosh, III
(74) *Attorney, Agent, or Firm* — Jing G. Sun

(57) ABSTRACT

The present disclosure relates to compounds of Formula (I) or Formula (II), which inhibit Gal-3, and include pharmaceutically acceptable salts, compositions comprising such compounds, and methods using and making such compounds and compositions.

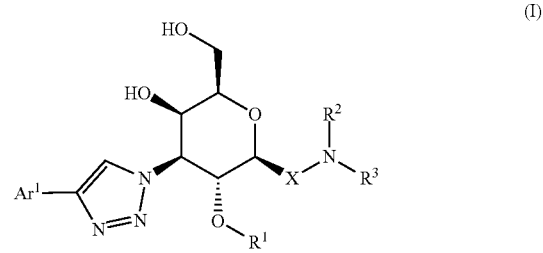

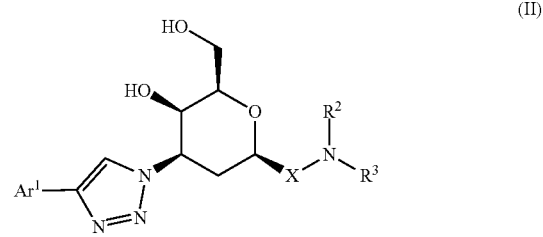

13 Claims, No Drawings

SMALL MOLECULE INHIBITORS OF GALECTIN-3

CROSS-REFERENCE TO RELATED APPLICATIONS

This application is a 371 of International Application No. PCT/US2021/030540 filed on May 4, 2021, which claims the priority benefit of U.S. Provisional Application No. 63/020,041, filed May 5, 2020; the content of which is herein incorporated by reference in its entirety.

BACKGROUND OF THE INVENTION

Galectin-3 (Gal-3) is a β-galactoside binding lectin of about 30 KDa (Cell 76: 597-598), that is involved in the regulation of inflammatory and fibrotic processes. (Immunological Reviews 230: 160-171). Under uncontrolled inflammation and pro-fibrotic condition, Gal-3 promotes fibroblast proliferation and transformation and mediates collagen production (Circulation 110:3121-3128).

Gal-3 is localyzed in many cellular location such as cytoplasm, nucleus, and cell surface. Gal-3 is also secreted by various cell types, mainly macrophages and monocytes into the blood stream (J Pharmacol Exp Ther 351:336-343). There are multiple lines of evidence in the literature supporting the involment of Gal-3 in the development of fibrotic process in multiple organs such as lung (Am J. Respir. Crit. Care Med. 185: 537-546), liver (PNAS 103:5060-5065) and kidney (Am. J. Pathol. 172:288-298). Gal-3 has also been identified as a biomarker for heart failure indicating that modulation of Gal-3 has potential uses in the treatment of heart failure (Curr. Heart Fail. Rep. 7:1-8). Modulation of Gal-3 can be used in the treatment of cancer since Gal-3 is involved in cell growth and differentiation playing a critical role in angiogenic, apoptotic, and metastatic pathways (Galectin-3C: Human Lectin for Treatment of Cancer. ACS Symposium Series, Vol. 1115. Chapter 12, 195-23). Recently, Gal-3 inhibitors have proven to have positive effects when used in combination immunotherapy (Galectin Therapeutics. Press Release, Feb. 7, 2017).

Several publications and patent applications describe synthetic inhibitors of Gal-3 that are being explored as antifibrotic agents. Recent examples of these approach are WO2005113568, WO2005113569, WO2014067986, WO2017080973, WO2016120403, US20140099319 and WO2018209255.

DESCRIPTION OF THE INVENTION

The present disclosure relates to compounds of the present invention, which inhibit Gal-3, and include pharmaceutically acceptable salts, compositions comprising such compounds, and methods using and making such compounds and compositions.

In a 1st aspect, the present invention provides, inter alia, a compound of Formula (I) or Formula (II):

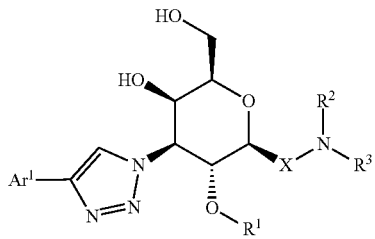
(I)

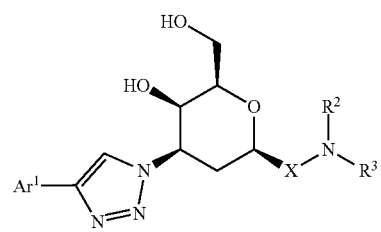
(II)

or a pharmaceutically acceptable salt thereof, wherein:
X is independently selected from —C(O)—, —CH$_2$—, and —CH$_2$C(O)—;
Ar$^1$ is independently phenyl or naphthyl; and wherein each ring moiety is substituted with 1 to 5 substituents selected from cyano, halogen, C$_{1-4}$ alkyl, C$_{1-4}$ alkoxy, C$_{1-4}$ haloalkyl, and C$_{1-4}$ haloalkoxy;
R$^1$ is independently selected from H, C$_{1-4}$ alkyl, C$_{1-4}$ haloalkyl, and —CH$_2$C(O)OH;
R$^2$ is independently selected from H, C$_{1-4}$ alkyl substituted with 0 to 1 OH, C$_{1-4}$ haloalkyl, —(CH$_2$)$_{0-2}$-C$_{3-6}$ cycloalkyl, and —(CH$_2$)$_{0-2}$-phenyl substituted with 0 to 3 halogen;
R$^3$ is independently C$_{3-6}$ cycloalkyl or heterocycloalkyl including from 4 to 7 ring atoms, wherein from 1 to 2 ring atoms are each independently selected from N(, N(R$^B$), and O, and S; wherein said ring moiety is substituted with 0 to 1 R$^5$ and 1 R$^{5A}$;
R$^5$ is independently OH, cyano, halogen, C$_{1-4}$ haloalkyl, C$_{1-4}$ alkoxy, C$_{1-4}$ haloalkoxy, and C$_{1-4}$ alkyl substituted with 0 to 1 OH;
R$^{5A}$ is independently selected from:

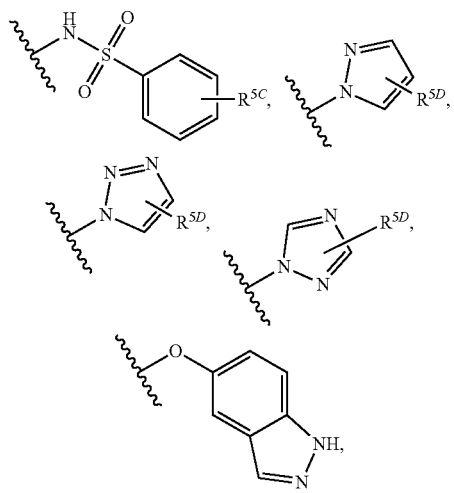

a bicyclic ring selected from

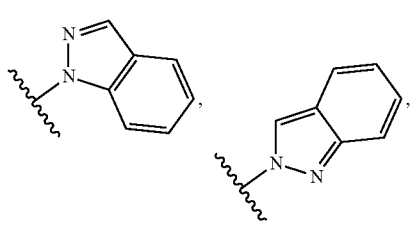

-continued

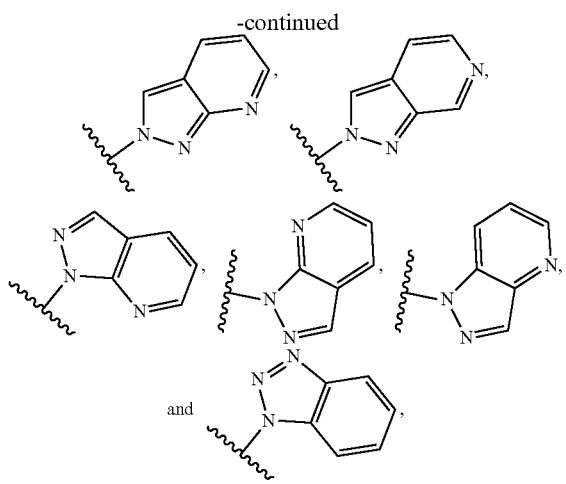

wherein said bicyclic ring is substituted 0 to 2 $R^{5C}$;

$R^{5B}$ is independently

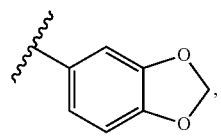 [SMILES: *c1ccc2c(c1)OCO2]

or phenyl substituted with 0 to 2 substituents selected from cyano, halogen, halogen, $C_{1-4}$ alkyl, $C_{1-4}$ alkoxy, $C_{1-4}$ haloalkyl, $C_{1-4}$ haloalkoxy;

$R^{5C}$ is independently selected from: cyano, halogen, $C_{1-4}$ alkyl, $C_{1-4}$ alkoxy, $C_{1-4}$ haloalkyl, and $C_{1-4}$ haloalkoxy;

$R^{5D}$ is independently selected from $R^{5C}$,

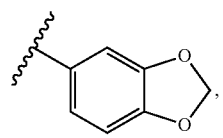

phenyl, naphthyl, pyridinyl, and primidinyl, wherein each ring moiety is substituted with 0 to 2 substituents selected from cyano, halogen, $C_{1-4}$ alkyl, $C_{1-4}$ alkoxy, $C_{1-4}$ haloalkyl, $C_{1-4}$ haloalkoxy;

$R^{5E}$ is independently selected from: H, $C_{1-4}$ alkyl, Bn, —C(O)($C_{1-4}$ alkyl), —C(O)O($C_{1-4}$ alkyl), and

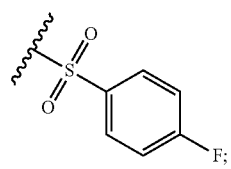

and $R^{5F}$ is independently —NH-phenyl, wherein said phenyl is substituted with 0 to 2 substituents selected from cyano, halogen, halogen, $C_{1-4}$ alkyl, $C_{1-4}$ alkoxy, $C_{1-4}$ haloalkyl, $C_{1-4}$ haloalkoxy.

In a 2nd aspect, within the scope of the 1st aspect, wherein:

X is —C(O)—; and $Ar^1$ is phenyl substituted with 1 to 3 halogen.

In another aspect, within the scope of the 1st or 2nd aspect, wherein:

$Ar^1$ is phenyl substituted with 1 to 3 F.

In another aspect, within the scope of the 1st or 2nd aspect, wherein the compound is of Formula (I).

In another aspect, within the scope of the 1st or 2nd aspect, wherein the compound is of Formula (II).

In a 3rd aspect, within the scope of the 1st or 2nd aspect, wherein:

$R^3$ is independently $C_{5-6}$ cycloalkyl or heterocycloalkyl including from 4 to 6 ring atoms, wherein from 1 to 2 ring atoms are each independently selected from $N(R^B)$, $N(R^E)$, and O; wherein each said ring moiety is substituted with 0 to 1 $R^5$ and 1 $R^{5A}$.

In a 4th aspect, within the scope of the 1st to 3rd aspects, wherein:

$R^3$ is independently selected from: H,

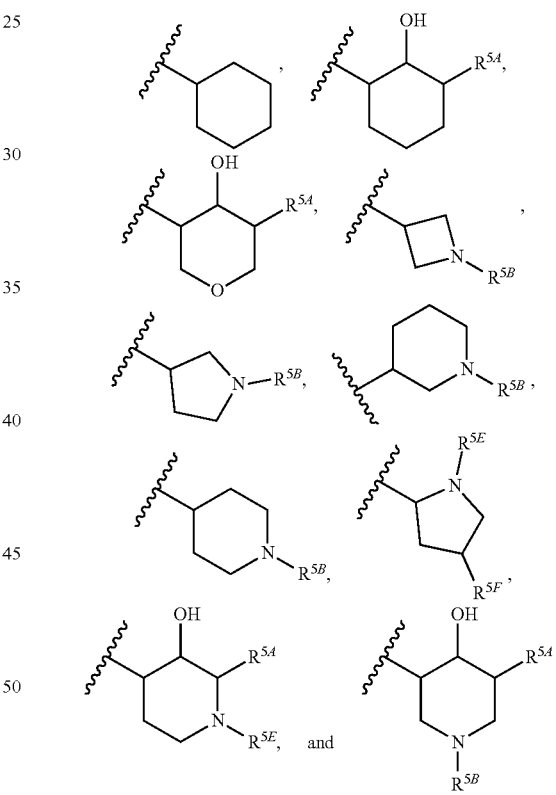

In a 5th aspect, within the scope of the 1st to 4th aspects, wherein:

$R^3$ is independently selected from:

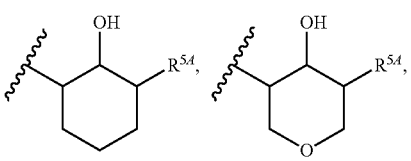

-continued

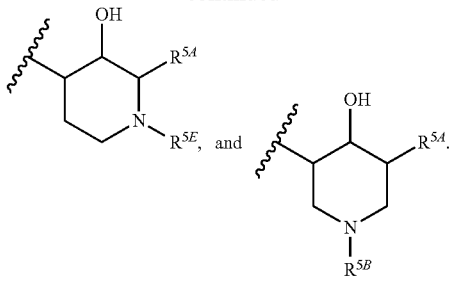

In a 6th aspect, within the scope of the 1st to 4th aspects, wherein:

$R^3$ is independently selected from:

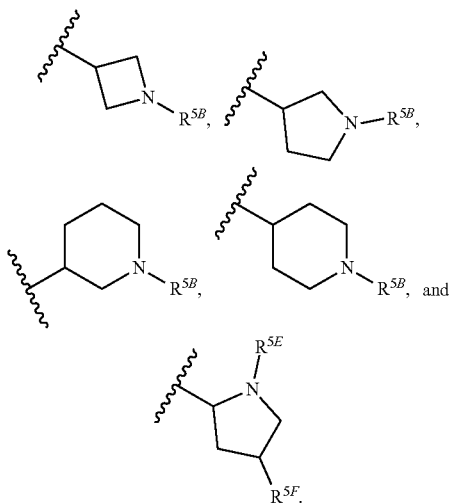

In another aspect, within the scope of the 1st to 4th aspects, wherein:

$R^3$ is independently selected from:

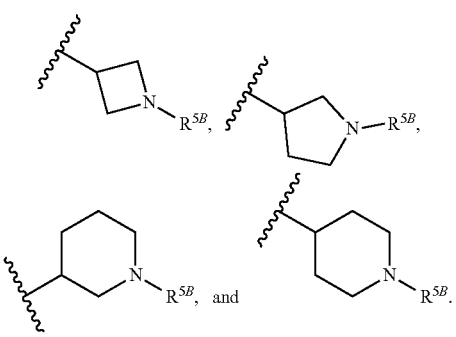

In a 7th aspect, within the scope of the 1st to 4th aspects, wherein:

$R^1$ is independently H or $C_{1-4}$ alkyl; and $R^2$ is independently selected from H, $C_{1-4}$ alkyl substituted with 0 to 1 OH, $C_{1-4}$ haloalkyl, —$(CH_2)_{0-1}$-cyclopropyl, and —$CH_2$-(phenyl substituted with 0 to 2 halogen).

In an 8th aspect, within the scope of the 1st to 5th aspect, wherein:

$R^1$ is independently H or $CH_3$; and $R^2$ is independently selected from: H, $CH_3$, —$CH_2CH_3$, —$CH_2CH_2OH$, —$CH_2CHF_2$, cyclopropyl and cyclopryopylmethyl.

In another aspect, within the scope of any of the 1st to 6th aspects, wherein $R^1$ is H.

In another aspect, within the scope of any of the 1st to 6th aspects, wherein $R^1$ is $CH_3$.

In another aspect, the invention provides a compound selected from the exemplified examples or a pharmaceutically acceptable salt thereof.

In another aspect, the invention provides a compound selected from the exemplified Examples or a pharmaceutically acceptable salt thereof.

Unless specified otherwise, these terms have the following meanings. "Alkyl" means a straight or branched alkyl group composed of 1 to 6 carbons. "Cycloalkyl" means a monocyclic ring system composed of 3 to 7 carbons. Terms with a hydrocarbon moiety (e.g. alkoxy) include straight and branched isomers for the hydrocarbon portion which are composed of 1 to 6 carbons. "Halo" includes fluoro, chloro, bromo, and iodo. "Haloalkyl" and "haloalkoxy" include all halogenated isomers from monohalo to perhalo. "Aryl" means a monocyclic or bicyclic aromatic ring system having 5 to 12 carbon atoms wherein one or both of the rings are aromatic. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Where a bonding attachment location is not specified, the bonding may be attached at any appropriate location as understood by practitioners in the art. Combinations of substituents and bonding patterns are only those that result in stable compounds as understood by practitioners in the art. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Gal 3 HTRF Assay
  ASSAY BUFFER Composition: 25 mM HEPES, 100 mM NaCl, 0.005% Tween 20, 0.05% BSA prepared in sterile water (all reagents from Sigma).
Controls:
  Positive Control: 100% DMSO (1 µL)+His-tagged hGal-3 (20 µL)+B-ASF (20 µL)+Anti-His Terbium Antibody (5 µL)+Strep d2 Antibody (5 µL).
  Negative Control: 100% DMSO (1 µL)+His-tagged hGal-3(20 µL)+Anti His Terbium Antibody (5 µL)+Strep d2 Antibody (5 µL).
Stocks Preparation:

| | Stock Conc. | Intermediate Conc. | Final Assay Conc. | Volume |
|---|---|---|---|---|
| His-tagged hGal-3 | 49.82 µM or can vary batch to batch | 2.525× | 15 nM | 20 µL |
| B-ASF | 25 µM | 2.525× | 15 nM | 20 µL |
| Compounds | 20 mM in 100% DMSO | Various concentration 100% DMSO | Various concentration 2% DMSO | 1 µL |
| Anti-His Tb Ab | 5.75 µM | (10×) 10 nM | 1 nM | 5 µL |
| Strep d2 | 16.67 µM | (10×) 200 nM | 20 nM | 5 µL |
| Total Assay volume | | | | 51 µL |

PROTOCOL: The Gal-3 assays were performed in 384 white Opti plates in three replicates at room temperature with gentle shaking at 250-300 rpm From the original stocks, 2.525× working stock concentrations of His-tagged recombinant human Gal-3 (hGal-3) and that of B-ASF were prepared. From the working stock, 20 µL of hGal-3 (15 nM) and 20 µL B-ASF (15 nM) were added to the plates. In Negative Control, only hGal-3 was added. A concentration range of 50× working stocks were prepared for the compounds in 100% DMSO. Aliquots of 1 µL of the compounds were added to the wells and pre-incubated with 20 µL hGal-3 per well for 30 minutes Then 20 µL B-ASF were added and incubated for another 1 hour. To detect the signal, 5 µL (final conc. of 1.0 nM) terbium labelled Anti-His antibody was added and incubated for 30 min followed by adding 5 µL (final conc. of 20 nM) Streptavidin d2 and incubation for another 1 hour. The assay signal was detected using HTRF screen protocol (Excitation wavelength=340 nm, emission wavelength=615 nm/665 nm) on Envision 2104 Multilabel Reader. Data analysed using Toolset and Curve Master. Results are reported in the experimental section ($IC_{50}$ in µM). All $IC_{50}$ reported were generated using the HTRF assay except when specifically indicated.

Gal-3 ELISA Assay
Materials:
  1. Coating Buffer: Phosphate Buffered Saline (1×)—PBS The Solution was prepared by dissolving the PBS packets procured from Sigma Aldrich (Catalogue No.: P3813-5×10Pak)—1 Pack in 1 Liter of Milli-Q water.
  2. Asialofetuin from fetal Calf Serum, Type-II. Sigma Aldrich (Catalogue No.: A1908-50MG).
  3. Fetal Bovine Serum. Invitrogen (Catalogue No.: 26400-044-500 mL).
  4. Tween-20. Sigma Aldrich (Catalogue No.: P1379-250 mL).
  5. BD OptEIA Enzyme Reagent Streptavidin-HRP (Catalogue No.: 554066).
  6. Sulphuric Acid. Sigma Aldrich (Catalogue No.: 25,810-5).
  7. Paraformaldehyde. Sigma Aldrich (Catalogue No.: P6148-500G).
  8. TMB Substrate. BD Biosciences (Catalogue No.: 555214).
  9. Biotin-tagged hGalectin-3—A 0.82 mg/mL stock solution (28.6 kDa, 28.6713 uM) of biotin tagged hGal-3 in-house synthesized by the proteomic group was used for the titration.
  10. TD-139 (EXT-001109-01-001): A small molecule synthesized in-house, used as an internal standard for the small molecule screening in hGalectin-3 neutralization binding assay.
A. Protocol
  a. Coating of Plate: The ASF at concentration 15 nM was prepared in 1× PBS and was plated in the 96 well flat-bottom nunc plates (Nunc immuno plate, Maxisorp, Catalogue No.: 439454) according to the plate-map and was incubated overnight at 4° C. after sealing the plates with a top-seal.
  b. Fixing and Blocking of Plate: On the assay day, the coating solution was drained and the plates were fixed by addition of 100 µL of 2%
    Paraformaldehyde solution and incubating at 37° C. for 30 min. and washed with 300 µL of wash buffer (PBS with 0.05% Tween-20) for 3 times, spin dried and taken for blocking.
  The plates were later blocked with 10% FBS and incubated for 1 h at room temperature. Later the plate was washed with 300 µL of wash buffer (PBS with 0.05% Tween-20) for 3 times.
  B. Incubation: After spin drying the plates from previous washing, 100 µL of test compounds, at various concentrations as specified in the plate-map (pre-incubated with the hGalectin-3 or mGalectin-3 at concentration 15 nM for 1 h at Room Temperature-RT) were added onto the plate as per the plate map. The plates were run in duplicates for data duplication and reproducibility.
  These plates were incubated at RT for 1 h and were washed for 5 times with wash buffer, spin dried and 100 µL of Streptavidin HRP (1:1000 dilutions) was added and incubated for 1 h at room temperature and washed for 7 times with wash buffer.
  C. Detection: After spin drying the plate from previous washing, 100 µL of TMB Substrate was added to each well and incubated for 15 min. at room temperature. Later the reaction was stopped with 2N sulphuric acid and the plate was read in spectramax at 450 nm
  Results: The read out (OD) obtained were plotted against the control wells after normalization with averaged controls and analyzed for the Log of Inhibitory concentration 50 (Log $IC_{50}$) values for program compounds.

Summary: The $IC_{50}$ values of the program compounds were as presented in the report (attached in excel format from Curve master compilation). The Plate control TD-139 had an $IC_{50}$ value of 10.3 nM and 108.12 nM for human and mouse Galectin-3 respectively. The same was plotted on the semilog graph.

Pharmaceutical Composition and Methods of Use

The compounds of this invention inhibit Gal-3. Accordingly, another aspect of the invention is a pharmaceutical composition comprising a therapeutically effective amount of a compound of the present invention, or a pharmaceutically acceptable salt thereof, and a pharmaceutically acceptable carrier.

Another aspect of the invention is a method for treating a patient afflicted with a disease or condition selected from fibrosis of organs (including liver, kidney, lung, heart and skin), liver diseases and conditions (including acute hepatitis, chronic hepatitis, liver fibrosis, liver cirrhosis, portal hypertension, regenerative failure, non-alcoholic steatohepatitis (NASH), liver hypofunction, and hepatic blood flow disorder), cell proliferative diseases, cancers, and conditions (including solid tumor, solid tumor metastasis, vascular fibroma, myeloma, multiple myeloma, Kaposi's sarcoma, leukemia, chronic lymphocytic leukemia (CLL)) and invasive metastasis of cancer cell), inflammatory diseases and conditions (including psoriasis, nephropathy, and pneumonia), gastrointestinal tract diseases and conditions (including irritable bowel syndrome (IBS), inflammatory bowel disease (IBD), and abnormal pancreatic secretion), renal diseases and conditions, urinary tract-associated diseases and conditions (including benign prostatic hyperplasia or symptoms associated with neuropathic bladder disease, spinal cord tumor, hernia of intervertebral disk, spinal canal stenosis, and symptoms derived from diabetes), lower urinary tract diseases and conditions (including obstruction of lower urinary tract), inflammatory diseases and conditions of lower urinary tract (including dysuria and frequent urination), pancreatic diseases and conditions, abnormal angiogenesis-associated diseases and conditions (including arterial obstruction), scleroderma, brain-associated diseases and conditions (including cerebral infarction and cerebral hemorrhage), neuropathic pain and peripheral neuropathy, ocular diseases and conditions (including age-related macular degeneration (AMD), diabetic retinopathy, proliferative vitreoretinopathy (PVR), cicatricial pemphigoid, and glaucoma filtration surgery scarring) with a compound of the present invention.

Another aspect of the invention is a method of treating renal fibrosis, pulmonary fibrosis, hepatic fibrosis, arterial fibrosis and systemic sclerosis comprising administering to a compound of the present invention to a patient.

Another aspect of the invention is a method for treating fibrosis of organs (including liver, kidney, lung, heart and skin) comprising administering to a compound of the present invention to a patient.

Another aspect of the invention is a method for treating liver diseases and conditions (including acute hepatitis, chronic hepatitis, liver fibrosis, liver cirrhosis, portal hypertension, regenerative failure, non-alcoholic steatohepatitis (NASH), liver hypofunction, and hepatic blood flow disorder) comprising administering to a compound of the present invention to a patient.

Another aspect of the invention is a method for treating cell proliferative diseases, cancers, and conditions (including solid tumor, solid tumor metastasis, vascular fibroma, myeloma, multiple myeloma, Kaposi's sarcoma, leukemia, chronic lymphocytic leukemia (CLL)) and invasive metastasis of cancer cell) comprising administering to a compound of the present invention to a patient.

Another aspect of the invention is a method for treating inflammatory diseases and conditions (including psoriasis, nephropathy, and pneumonia) comprising administering to a compound of the present invention to a patient.

Another aspect of the invention is a method for treating gastrointestinal tract diseases and conditions (including irritable bowel syndrome (IBS), inflammatory bowel disease (IBD), and abnormal pancreatic secretion) comprising administering to a compound of the present invention to a patient.

Another aspect of the invention is a method for treating renal diseases and conditions comprising administering to a compound of the present invention to a patient.

Another aspect of the invention is a method for treating urinary tract-associated diseases and conditions (including benign prostatic hyperplasia or symptoms associated with neuropathic bladder disease, spinal cord tumor, hernia of intervertebral disk, spinal canal stenosis, and symptoms derived from diabetes) comprising administering to a compound of the present invention to a patient.

Another aspect of the invention is a method for treating lower urinary tract diseases and conditions (including obstruction of lower urinary tract), inflammatory diseases and conditions of lower urinary tract (including dysuria and frequent urination) comprising administering to a compound of the present invention to a patient.

Another aspect of the invention is a method for treating pancreatic diseases and conditions comprising administering to a compound of the present invention to a patient.

Another aspect of the invention is a method for treating abnormal angiogenesis-associated diseases and conditions (including arterial obstruction) comprising administering to a compound of the present invention to a patient.

Another aspect of the invention is a method for treating brain-associated diseases and conditions (including cerebral infarction and cerebral hemorrhage) comprising administering to a compound of the present invention to a patient.

Another aspect of the invention is a method for treating neuropathic pain and peripheral neuropathy comprising administering to a compound of the present invention to a patient.

Another aspect of the invention is a method for treating ocular diseases and conditions (including age-related macular degeneration (AMD), diabetic retinopathy, proliferative vitreoretinopathy (PVR), cicatricial pemphigoid, and glaucoma filtration surgery scarring) comprising administering to a compound of the present invention to a patient.

The compounds of the invention may be used in the treatment and/or prophylaxis of conditions in which Gal-3 plays a role.

The compounds of the present invention may be used for the manufacture of a medicament for the treatment and/or prophylaxis of a condition in which inhibition of the physiological activity of Gal-3 is useful, such as diseases in which a Gal-3 receptor participates, is involved in the etiology or pathology of the disease, or is otherwise associated with at least one symptom of the disease.

The compounds of the invention can be used alone, in combination with other compounds of the present invention, or in combination with one or more, preferably one to two other agent(s).

"Therapeutically effective" means the amount of agent required to provide a meaningful patient benefit as understood by practitioners in the field of pain.

"Patient" means a person afflicted with pain and suitable for therapy as understood by practitioners in the field.

"Treatment," "therapy," "regimen," and related terms are used as understood by practitioners in the field.

The compounds of this invention are generally given as pharmaceutical compositions comprised of a therapeutically effective amount of a compound of the present invention or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, PA (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

Chemical Methods

It will be evident to one skilled in the art that the present disclosure is not limited to the foregoing illustrative examples, and that it can be embodied in other specific forms without departing from the essential attributes thereof. The examples therefore should be considered in all respects as illustrative and not restrictive, reference being made to the appended claims, rather than to the foregoing examples, and all changes which come within the meaning and range of equivalency of the claims are therefore intended to be embraced.

Section A

LCMS analyses were performed on Waters Acquity UPLC system coupled with Waters TUV and SQ mass detector (Column: BEH C18 2.1×50 mm; Mobile Phase A: water with 0.05% TFA; Mobile Phase B: acetonitrile with 0.05% TFA; Gradient: 2-98% B over 1.6 minutes; Flow: 0.8 mL/min); HPLC analyses were performed on Shimadzu LC10-AT HPLC system coupled with SPD-10AV UV detector (Column YMC S5 Combiscreen ODS 4.6×50 mm; Mobile Phase A: 5:95 acetonitrile: water with 0.1% TFA; Mobile Phase B: 95:5 acetonitrile:water with 0.1% TFA; Gradient: 0-100% B over 40 minutes, then a 1-minute hold at 100% B; Flow: 1 mL/min); Preparative HPLC purifications were conducted on Shimadzu LC-8 preparative HPLC system coupled with SPD 20 UV detector. Detailed conditions are described in experimental procedures.

Methods of Preparation

Analytical LC-MS/HPLC retention time reported for each example and intermediate uses one of the following general analytical LC-MS/HPLC conditions:

LCMS Conditions:

Method A: Column: Ascentis Express C18 (50×2.1 mm), 2.7 µm; Mobile Phase A: 5:95 acetonitrile:water with 10 mM $NH_4OAc$; Mobile Phase B: 95:5 acetonitrile: water with 10 mM $NH_4OAc$; Temperature: 50° C.; Gradient: 0-100% B over 3 minutes.

Method B: Column: Ascentis Express C18 (50×2.1 mm), 2.7 µm; Mobile Phase A: 5:95 acetonitrile:water with 0.1% TFA; Mobile Phase B: 95:5 acetonitrile:water with 0.1% TFA; Temperature: 50° C.; Gradient:0-100% B over 3 minutes; Flow: 1.1 ml/min.

Method C: Column-KINETEX-XB-C18 (75×3 mm-2.6 µm); Mobile Phase A: 10 mM $NH_4COOH$ IN WATER: ACN(98:02); Mobile Phase B: 10 mM $NH_4COOH$ in WATER:ACN(02:98); Gradient=20-100% B over 4 minutes; Flow rate: 1.1 mL/min; Detection: UV at 254 nm.

Method D: Column: Waters Acquity UPLC BEH C18 (2.1×50 mm), 1.7µ; Mobile phase A: 0.1% TFA in water; Mobile phase B: 0.1% TFA in ACN; Gradient=20-90% B over 1.1 minute, then a 0.6 minute hold at 90% B; Temperature: 50° C.; Flow rate: 0.7 mL/min; Detection: UV at 220 nm.

Method E: Column: Waters Acquity UPLC BEH C18 (2.1×50 mm) 1.7µ, Mobile phase A: 5 mM $NH_4OAc$, Acetonitrile (95:5); Mobile phase B: 5 mM $NH_4OAc$: ACN (5:95), Gradient=20-90% B over 1.1 minute, then a 0.6 minute hold at 90% B; Temperature: 50° C.; Flow rate: 0.7 mL/min; Detection: UV at 220 nm Method F: Column—ZORBAX SB-C18 (50×4.6 mm-5.0 µm); M.phase A: 10 mM $NH_4COOH$ IN WATER:ACN (98:02); M.phase B: 10 mM $NH_4COOH$ IN WATER: ACN(02:98); Gradient=30-100% B over 4 minutes; Flow rate: 1.5 mL/min; Detection: UV at 254 nm.

Prep-HPLC Conditions:

Method A: Column: Waters XBridge C18, 19×150 mm, 5-µm particles; Mobile Phase A: 10-mM $NH_4OAc$; Mobile Phase B: acetonitrile; Gradient: 15-50% B over 20 minutes, then a 5-minute hold at 100% B; Flow: 15 mL/min.

Method B: Column: Inertsil ODS(250*19)mm-5 µm particles; Mobile Phase A: 10-mM $NH_4OAc$-pH 4.5; Mobile Phase B: ACN; Gradient: 30-50% B over 27 minutes, then a 5-minute hold at 100% B; Flow: 17 mL/min.

Method C: Column Symmetry C8 (300 mm×19 mm)-7 µm particles; Mobile Phase A: 10-mM $NH_4OAc$-pH 4.5; Mobile Phase B: ACN; Gradient: 50-70% B over 24 minutes, then a 5-minute hold at 100% B; Flow: 17 mL/min.

Method D: Column: Inertsil ODS(250*19)mm-5 μm particles; Mobile Phase A: 10-mM NH₄OAc-pH 4.5; Mobile Phase B: ACN; Gradient: 25-60% B over 20 minutes, then a 5-minute hold at 100% B; Flow: 30 mL/min.

Method E: Column: Lux-cellulose C4(250×21.2)mm, 5 μm particles; Mobile Phase A: 0.1% DEA in MeOH; Gradient: 100% A over 20 minutes, then a 5-minute hold at 100% B; Flow: 19 mL/min.

Method F: Column: Lux-cellulose C2(250×21.2)mm, 5 μm particles; Mobile Phase A: 10 mM Ammonium formate; Mobile.Phase B: ACN:MeOH(1:1); Gradient: 80% B over 20 minutes, then a 5-minute hold at 100% B; Flow: 19 mL/min.

Synthesis of Carboxylic Acid Intermediate:

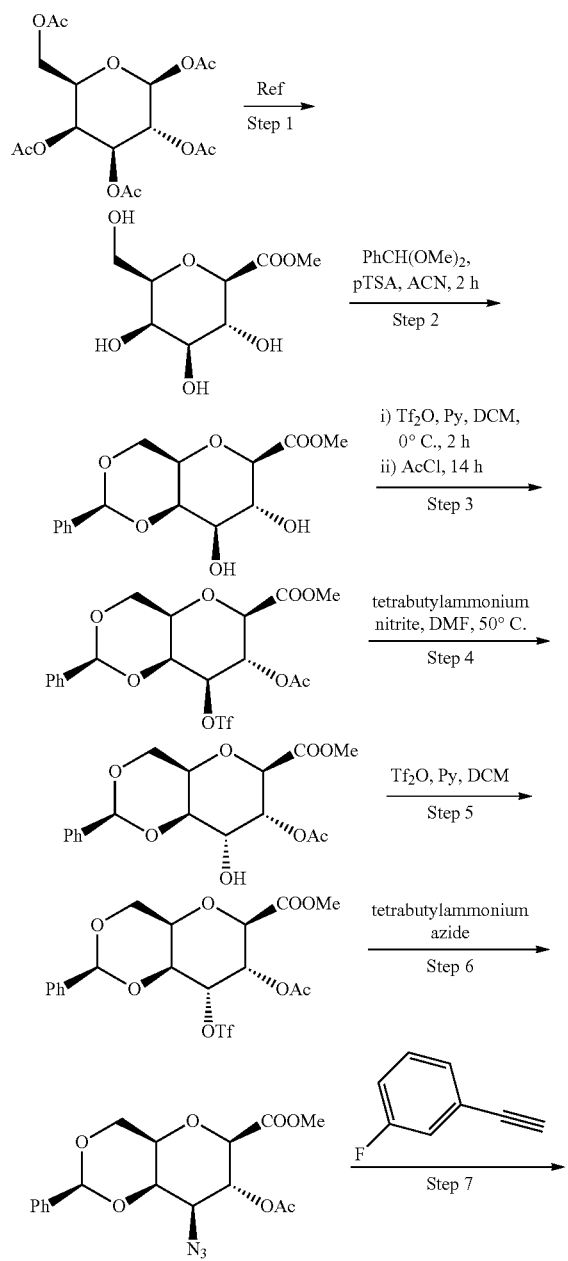

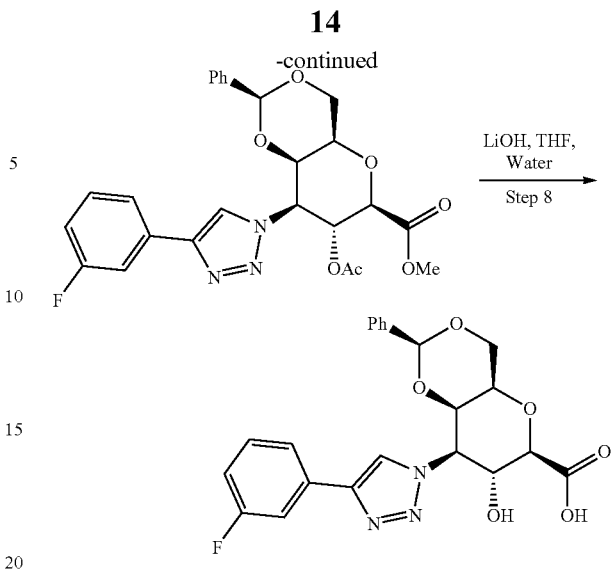

Step 1: Synthesis of (2R,3R,4S,5R,6R)-methyl 3,4,5-trihydroxy-6-(hydroxymethyl)tetrahydro-2H-pyran-2-carboxylate: Synthesized from β-D-galactose pentaacetate by following literature procedure (Ref: Synthesis, 2007, 6, 845-852 and references cited therein).

Step 2: Synthesis of (2S,4aR,6R,7R,8R,8aR)-methyl 7,8-dihydroxy-2-phenylhexahydropyrano[3,2-d][1,3]dioxine-6-carboxylate: p-Toluenesulfonic acid monohydrate (1.199 g, 6.30 mmol) was added to a stirred suspension of (2R,3R, 4S,5R,6R)-methyl 3,4,5-trihydroxy-6-(hydroxymethyl)tetrahydro-2H-pyran-2-carboxylate (29 g, 90 mmol) and benzaldehyde dimethyl acetal (33.8 mL, 225 mmol) in acetonitrile (563 mL) at rt under Ar atmosphere. The mixture was degassed with Ar three times and sonicated for 2 min. Then, the reaction mixture was stirred at rt for 4 h, quenched with TEA (5.77 mL, 41.4 mmol) and stirred for 10 min. The mixture was filtered and the filtrate was concentrated under reduced pressure to get the crude product which was purified via chromatography in silica gel (50-100% EtOAc in n-hexane) to yield the title compound (16.3 g, 52.5 mmol, 58%) as a white solid. 1H NMR (400 MHz, CHLOROFORM-d): δ 7.53-7.49 (m, 2H), 7.40-7.36 (m, 3H), 5.57 (s, 1H), 4.39 (dd, J=12.5, 1.5 Hz, 1H), 4.28 (dd, J=4.0, 1.0 Hz, 1H), 4.15-4.05 (m, 2H), 3.87-3.84 (m, 4H), 3.73 (td, J=9.0, 4.0 Hz, 1H), 3.56 (q, J=1.5 Hz, 1H), 3.24 (d, J=2.5 Hz, 1H), 2.63 (d, J=8.5 Hz, 1H).

Step 3: Synthesis of (2S,4aR,6R,7S,8S,8aS)-methyl-7-acetoxy-2-phenyl-8-(((trifluoromethyl)sulfonyl)oxy)hexahydropyrano[3,2-d][1,3]dioxine-6-carboxylate: To a solution of (2S,4aR,6R,7R,8R,8aR)-methyl 7,8-dihydroxy-2-phenylhexahydropyrano[3,2-d][1,3]dioxine-6-carboxylate (17.3 g, 55.8 mmol) in DCM (180 mL), pyridine (18.04 mL, 223 mmol) was added at −15° C. and the mixture was stirred for 10 min. Triflic anhydride (8.48 mL, 50.2 mmol) was added drop-wise over a period of 15 min under argon and the mixture was stirred for 1 h at −15° C. The reaction mixture was allowed to reach rt over a period of 2 h. Acetyl chloride (4.76 mL, 66.9 mmol) was added at 0° C., and the mixture was allowed to warm to rt and stirred for 10 h. DCM (300 mL) was added, and the solution was washed with 0.7 N HCl (150 mL), saturated sodium bicarbonate (2×100 mL) and brine solution. The organic layer was separated and dried over sodium sulfate. The solvent was removed under reduced pressure and purified via chromatography in silica gel (30-80% EtOAc in n-hexane) to yield the title compound (14 g, 28.9 mmol, 52%) as a white solid. 1H NMR (400

MHz, CHLOROFORM-d): δ 7.53 (dd, J=7.4, 2.1 Hz, 2H), 7.44-7.36 (m, 3H), 5.64 (d, J=9.9 Hz, 1H), 5.60 (s, 1H), 5.00 (dd, J=9.9, 3.6 Hz, 1H), 4.53 (d, J=3.6 Hz, 1H), 4.42 (dd, J=12.8, 1.5 Hz, 1H), 4.08 (dd, J=12.8, 1.5 Hz, 1H), 4.03 (d, J=9.9 Hz, 1H), 3.77 (s, 3H), 3.59 (d, J=1.0 Hz, 1H), 2.10 (s, 3H).

Step 4: Synthesis of (2S,4aR,6R,7R,8R,8aR)-methyl-7-acetoxy-8-hydroxy-2-phenylhexahydropyrano[3,2-d][1,3]dioxine-6-carboxylate: To a solution of (2S,4aR,6R,7S,8S,8a5)-methyl-7-acetoxy-2-phenyl-8-(((trifluoromethyl)sulfonyl)oxy) hexahydropyrano[3,2-d][1,3]dioxine-6-carboxylate (32 g, 66.1 mmol) in DMF (320 mL), tetrabutylammonium nitrate (50.3 g, 165 mmol) was added and degasified twice with argon and the mixture was heated at 50° C. for 6 h. Then the reaction mixture was diluted with EtOAc (500 mL), washed with water (4×200 mL), dried over sodium sulfate and concentrated under reduced pressure. The residue was purified via chromatography in silica gel (60-100% EtOAc in n-hexane) to yield the title compound (15 g, 42.6 mmol, 64%) as a yellow solid. 1H NMR (400 MHz, CHLOROFORM-d): δ 7.55-7.51 (m, 2H), 7.42-7.36 (m, 3H), 5.55 (s, 1H), 5.39 (dd, J=10.3, 2.8 Hz, 1H), 4.45 (d, J=10.3 Hz, 1H), 4.37 (dd, J=12.8, 1.5 Hz, 1H), 4.23 (t, J=3.1 Hz, 1H), 4.16-4.13 (m, 1H), 4.05 (dd, J=12.8, 2.0 Hz, 1H), 3.79 (d, J=1.5 Hz, 1H), 3.75 (s, 3H), 2.10 (s, 3H).

Step 5: Synthesis of (2S,4aR,6R,7S,8R,8aS)-methyl-7-acetoxy-2-phenyl-8-(((trifluoromethyl)sulfonyl)oxy)hexahydropyrano[3,2-d][1,3]dioxine-6-carboxylate: To a solution of (2S,4aR,6R,7R,8R,8aR)-methyl 7-acetoxy-8-hydroxy-2-phenylhexahydropyrano[3,2-d][1,3]dioxine-6-carboxylate (2.3 g, 6.53 mmol) in DCM (20 mL), pyridine (2.112 mL, 26.1 mmol) was added and the mixture was cooled to −15° C. followed by drop wise addition of triflic anhydride (1.654 mL, 9.79 mmol) under argon and stirred for 1 h at −15° C. The reaction mixture was allowed to warm to rt and stirred for 2 h. Then, the reaction mixture was diluted with DCM (200 mL), washed with aq. 0.7 N HCl (50 mL), aq.NaHCO$_3$ (2×50 mL), brine solution and dried over sodium sulphate. The solvent was removed under reduced pressure and the residue was purified via chromatography in silica gel (30-80% EtOAc in n-hexane) to yield the title compound (1.2 g, 2.477 mmol, 38%) as a solid. 1H NMR (400 MHz, CHLOROFORM-d): δ 7.54-7.49 (m, 2H), 7.43-7.38 (m, 3H), 5.60 (s, 1H), 5.54 (dd, J=10.5, 3.0 Hz, 1H), 5.28 (t, J=3.3 Hz, 1H), 4.43-4.37 (m, 2H), 4.30 (dd, J=3.5, 1.0 Hz, 1H), 4.11 (dd, J=12.8, 1.5 Hz, 1H), 3.80 (s, 3H), 3.78 (d, J=1.5 Hz, 1H), 2.10 (s, 3H).

Step 6: Synthesis of (2S,4aR,6R,7R,8S,8aR)-methyl-7-acetoxy-8-azido-2-phenylhexahydropyrano[3,2-d][1,3]dioxine-6-carboxylate: To a solution of (2S,4aR,6R,7S,8R,8aS)-methyl-7-acetoxy-2-phenyl-8-(((trifluoromethyl)sulfonyl)oxy) hexahydropyrano[3,2-d][1,3]dioxine-6-carboxylate (1.8 g, 41.3 mmol) in DMF (18 mL), tetrabutyl ammonium azide (3.17 g, 11.15 mmol) was added in a single portion. The mixture was degasified with Ar and heated at 50° C. for 5 h. The reaction mixture was diluted with EtOAc (200 mL), washed with water (3×100 mL), dried over sodium sulfate and concentrated. The residue was purified via chromatography in silica gel (50-90% EtOAc in n-hexane) to yield the title compound (1.2 g, 3.18 mmol, 86%) as a off-white solid. LC-MS, [M+18]$^+$=395.2, {Method C: t$_R$=2.37 min}. 1H NMR (300 MHz, CHLOROFORM-d): δ 7.53 (dd, J=7.2, 2.3 Hz, 2H), 7.42-7.33 (m, 3H), 5.60 (s, 1H), 5.58-5.51 (m, 1H), 4.40-4.33 (m, 2H), 4.06 (dd, J=12.7, 1.7 Hz, 1H), 3.99 (d, J=9.8 Hz, 1H), 3.76 (s, 3H), 3.50 (s, 1H), 3.41 (dd, J=10.4, 3.2 Hz, 1H), 2.11 (s, 3H).

Step 7: Synthesis of (4aR,6R,7R,8S,8aR)-methyl 7-acetoxy-8-(4-(3-fluorophenyl)-1H-1,2,3-triazol-1-yl)-2-phenylhexahydropyrano[3,2-d][1,3]dioxine-6-carboxylate: To a solution of (4aR,6R,7R,8S,8aR)-methyl 7-acetoxy-8-azido-2-phenylhexahydropyrano[3,2-d][1,3]dioxine-6-carboxylate (1.2 g, 3.18 mmol) in DMF (50 mL) and water (10.00 mL). 1-ethynyl-3-fluorobenzene (1.146 g, 9.54 mmol), Sodium ascorbate (0.693 g, 3.50 mmol) and copper(II) sulfate pentahydrate (0.715 g, 2.86 mmol) were added sequentially. Reaction mixture was degassed with nitrogen for 10 min and heated to 80° C. for 1 h. The reaction mixture was cooled to RT and diluted with water (60 ml) and DCM (50 ml) and stir for 1 h. Reaction mixture was filtered through celite pad, washed with DCM (100 ml), filtrate taken for further workup. The organic layer separated out and aqueous layer was re-extracted with DCM (2×100 ml), combined organic layer was washed with water (400 ml), brine (100 ml), dried the organic layer over sodium sulfate and concentrated under reduced pressure. To the crude residue, diethyl ether was added and solid was filtered through Buchner funnel and dried for 1 h to the title compound (1.1 g, 2.211 mmol, 69.5% yield) as a white solid. LC-MS, [M+H]$^+$=498.2, {Method C: t$_R$=2.71 min}. $^1$H NMR (400 MHz, CDCl$_3$): δ ppm 8.07 (s, 1H), 7.54-7.50 (m, 2H), 7.48-7.35 (m, 6H), 7.05-6.99 (m, 1H), 5.90 (dd, J=11.1, 9.6 Hz, 1H), 5.52 (s, 1H), 5.21 (dd, J=11.1, 3.4 Hz, 1H), 4.51-4.47 (m, 2H), 4.23 (d, J=9.5 Hz, 1H), 4.12 (dd, J=12.8, 1.8 Hz, 1H), 3.81 (s, 3H), 3.80-3.78 (m, 1H), 1.87 (s, 3H).

Step-8: Synthesis of (4aR,6R,7R,8R,8aR)-8-(4-(3-fluorophenyl)-1H-1,2,3-triazol-1-yl)-7-hydroxy-2-phenylhexahydropyrano[3,2-d][1,3]dioxine-6-carboxylic acid: To a stirred solution of (4aR,6R,7R,8S,8aR)-methyl 7-acetoxy-8-(4-(3-fluorophenyl)-1H-1,2,3-triazol-1-yl)-2-phenylhexahydropyrano[3,2-d][1,3]dioxine-6-carboxylate (2 g, 4.02 mmol) in Tetrahydrofuran (20 mL) and Water (10 mL) was added lithium hydroxide (0.48 g, 20.10 mmol) and stirred the mixture at rt for 2 h. After confirmation of completion of reaction with LCMS, tetrahydrofuran was removed under reduced pressure. The residue was diluted with water (100 mL) and pH adjusted to approx 2-3 using 1.5N HCl solution. The precipitated solid was filtered and washed with water and dried under reduced pressure to yield the title compound (1.8 g, quantitative). LC-MS, [M+H]$^+$=442.2, {Method C: t$_R$=3.31 min}. $^1$H NMR (400 MHz, MEOH-d$_4$) δ ppm 8.46 (s, 1H), 7.56 (dt, J=10.2, 2.2 Hz, 2H), 7.49-7.40 (m, 3H), 7.37-7.30 (m, 3H), 7.09 (td, J=8.4, 2.3 Hz, 1H), 5.56 (s, 1H), 5.12 (dd, J=10.5, 3.5 Hz, 1H), 4.62 (t, J=10.0 Hz, 1H), 4.54 (d, J=3.5 Hz, 1H), 4.37 (d, J=12.5 Hz, 1H), 4.18 (dd, J=12.5, 1.5 Hz, 1H), 4.06 (d, J=9.5 Hz, 1H), 3.89 (s, 1H).

Synthesis of C2-Methoxy Carboxylic Acid Intermediate:

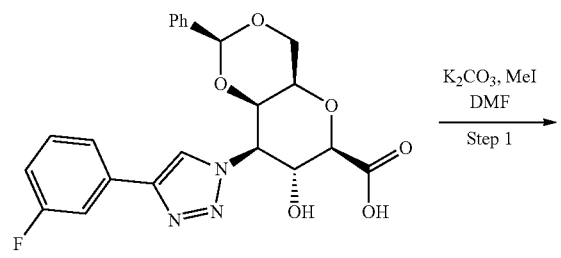

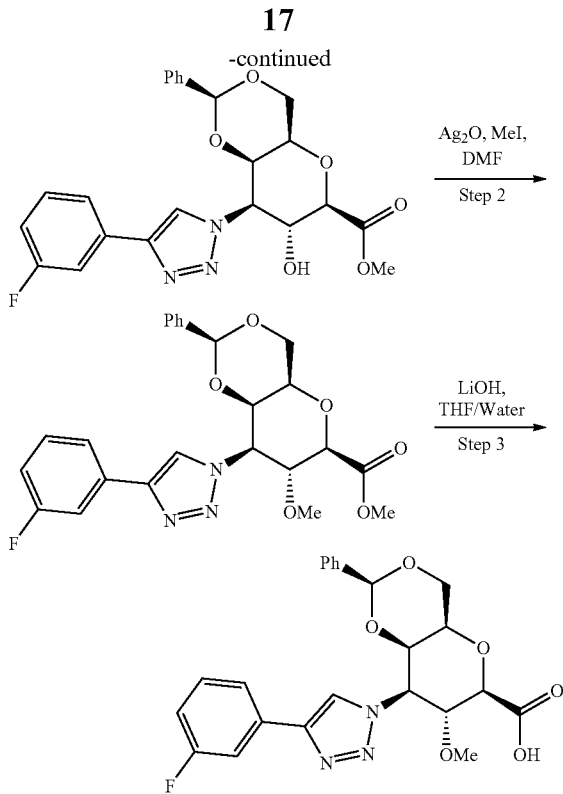

Step-1: Synthesis of (4aR,6R,7R,8R,8aR)-methyl 8-(4-(3-fluorophenyl)-1H-1,2,3-triazol-1-yl)-7-hydroxy-2-phenylhexahydropyrano[3,2-d][1,3]dioxine-6-carboxylate: To a stirred solution of (4aR,6R,7R,8R,8aR)-8-(4-(3-fluorophenyl)-1H-1,2,3-triazol-1-yl)-7-hydroxy-2-phenylhexahydropyrano[3,2-d][1,3]dioxine-6-carboxylic acid (1.55 g, 3.51 mmol) in DMF (10 mL), was added K$_2$CO$_3$ (4.85 g, 35.1 mmol) followed by MeI (1.976 mL, 31.6 mmol) and stirred at rt for 16 h. After confirmation of completion of reaction by LCMS, the reaction mass was quenched into ice water (100 mL) and stirred for 10 minutes. The solid was filtered and washed with water and dried under reduced pressure to yield the title compound as an off white solid (1.45 g, 91%). LC-MS, [M+H]$^+$=456.2, {Method F: t$_R$=1.95 min}. $^1$H NMR (400 MHz, MEOH-d$_4$) δ ppm 8.41 (s, 1H), 7.58 (d, J=8.0 Hz, 1H), 7.55-7.50 (m, 1H), 7.47-7.40 (m, 3H), 7.37-7.32 (m, 3H), 7.07 (td, J=8.3, 2.5 Hz, 1H), 5.56 (s, 1H), 5.11 (dd, J=11.0, 3.5 Hz, 1H), 4.68-4.61 (m, 1H), 4.53 (d, J=2.5 Hz, 1H), 4.32-4.26 (m, 1H), 4.20-4.13 (m, 2H), 3.89 (s, 1H), 3.82 (s, 3H).

Step-2: Synthesis of (4aR,6R,7R,8R,8aR)-methyl 8-(4-(3-fluorophenyl)-1H-1,2,3-triazol-1-yl)-7-methoxy-2-phenylhexahydropyrano[3,2-d][1,3]dioxine-6-carboxylate: To a stirred solution of (4aR,6R,7R,8R,8aR)-methyl 8-(4-(3-fluorophenyl)-1H-1,2,3-triazol-1-yl)-7-hydroxy-2-phenyl-hexahydropyrano[3,2-d][1,3]dioxine carboxylate (1.45 g, 3.18 mmol) in DMF (20 mL), was added 4 A MS (1 g) and stirred for 10 minutes at rt. Then, silver oxide (3.69 g, 15.92 mmol) and MeI (0.1 mL, 15.92 mmol) were added sequentially and stirred at rt for 16 h. Reaction mass was filtered through a celite pad, washed with excess DCM (20 mL) and filtrate was concentrated under reduced pressure to afford (4aR,6R,7R,8R,8aR)-methyl 8-(4-(3-fluorophenyl)-1H-1,2,3-triazol-1-yl)-7-methoxy-2-phenylhexahydropyrano[3,2-d][1,3]dioxine-6-carboxylate as an off white solid (1.3 g, 87%) which was as such taken for next step without further purification. LC-MS, [M+H]$^+$=470.2, {Method F: t$_R$=2.15 min}. $^1$H NMR (400 MHz, MEOH-d$_4$) δ ppm 8.59 (s, 1H), 7.62-7.58 (m, 1H), 7.55 (dt, J=10.0, 2.0 Hz, 1H), 7.50-7.42 (m, 3H), 7.40-7.35 (m, 3H), 7.08 (td, J=8.4, 2.3 Hz, 1H), 5.58 (s, 1H), 5.19 (dd, J=10.5, 3.5 Hz, 1H), 4.50 (d, J=2.5 Hz, 1H), 4.47-4.43 (m, 1H), 4.29 (dd, J=12.8, 1.8 Hz, 1H), 4.19-4.13 (m, 2H), 3.87 (s, 1H), 3.84 (s, 3H), 3.12 (s, 3H).

Step-3: Synthesis of (4aR,6R,7R,8R,8aR)-8-(4-(3-fluorophenyl)-1H-1,2,3-triazol-1-yl)-7-methoxy-2-phenylhexahydropyrano[3,2-d][1,3]dioxine-6-carboxylic acid: To a stirred solution of (4aR,6R,7R,8R,8aR)-methyl 8-(4-(3-fluorophenyl)-1H-1,2,3-triazol-1-yl)-7-methoxy-2-phenylhexahydropyrano[3,2-d][1,3]dioxine-6-carboxylate (1.3 g, 2.8 mmol) in Tetrahydrofuran (50 mL) and Water (50 mL) was added lithium hydroxide (0.33 g, 13.85 mmol) and stirred at rt for 1 h. After confirmation of completion of reaction with LCMS, solvent was removed under reduced pressure. Then the residue was diluted with water (100 mL) and pH adjusted to approx 2-3 using aq. 1.5N HCl solution. The precipitated solid was filtered, washed with water and dried under reduced pressure to yield the title compound as an off white solid (1.1 g, 85%). LC-MS, [M+H]$^+$=456.2, {Method F: t$_R$=0.64 min}. 1H NMR (400 MHz, MEOH-d4) δ ppm 8.58 (s, 1H), 7.61 (d, J=6.5 Hz, 1H), 7.55 (dd, J=10.0, 2.5 Hz, 1H), 7.50-7.41 (m, 3H), 7.36 (d, J=3.5 Hz, 3H), 7.11-7.04 (m, 1H), 5.58 (s, 1H), 5.16 (dd, J=11.0, 3.5 Hz, 1H), 4.50 (d, J=3.0 Hz, 1H), 4.42-4.35 (m, 1H), 4.34-4.29 (m, 1H), 4.16 (dd, J=12.8, 1.8 Hz, 1H), 4.06 (d, J=9.0 Hz, 1H), 3.84 (s, 1H), 3.18 (s, 3H).

Synthesis of C2-Deoxy Carboxylic Acid Intermediate (e.g., (4aR,6R,8R,8aR)-8-(4-(3-fluorophenyl)-1H-1,2,3-triazol-1-yl)-2-phenylhexahydropyrano[3,2-d][1,3]dioxine-6-carboxylic acid)

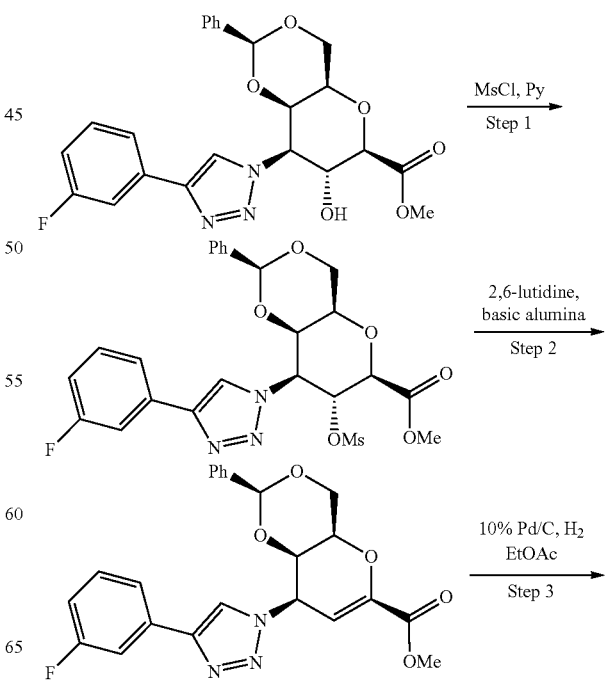

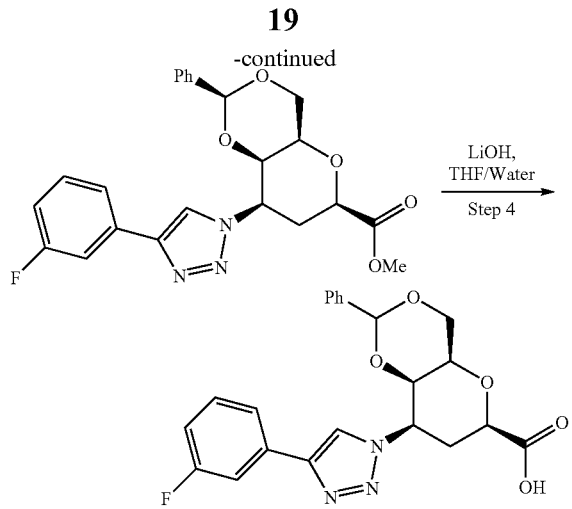

Step-1: Synthesis methyl (4aR,6R,7R,8S,8aR)-8-(4-(3-fluorophenyl)-1H-1,2,3-triazol-1-yl)-7-((methylsulfonyl)oxy)-2-phenylhexahydropyrano[3,2-d][1,3]dioxine-6-carboxylate: To a stirred solution of (4aR,6R,7R,8R,8aR)-methyl 8-(4-(3-fluorophenyl)-1H-1,2,3-triazol-1-yl)-7-hydroxy-2-phenylhexahydropyrano[3,2-d][1,3]dioxine-6-carboxylate (300 mg, 0.66 mmol) in Pyridine (4 mL) was added Mesyl-Cl (0.13 mL, 1.71 mmol) at 0° C. and the reaction mixture was stirred for 6 h. The reaction mixture was quenched with ice water and stirred for 5 minutes. The obtained solid was filtered, washed with excess water and dried to afford the title compound as an off-white solid (0.26 g, 72%). LC-MS, [M+H]$^+$=534.2, {Method C: $t_R$=1.990 min}.

Step-2: Synthesis of methyl (4aR,8R,8aR)-8-(4-(3-fluorophenyl)-1H-1,2,3-triazol-1-yl)-2-phenyl-4,4a,8,8a-tetrahydropyrano[3,2-d][1,3]dioxine-6-carboxylate: To a solution of (4aR,6R,7R,8S,8aR)-methyl 8-(4-(3-fluorophenyl)-1H-1,2,3-triazol-1-yl)-7-((methylsulfonyl)oxy)-2-phenylhexahydropyrano[3,2-d][1,3]dioxine-6-carboxylate (260 mg, 0.487 mmol) in 2,6-Lutidine (25 mL) was added aluminum oxide (Basic) (2.5 g, 24.37 mmol) at rt and the reaction mixture was heated at 50° C. for 16 h. The solvent was removed under reduced pressure and crude residue was purified via chromatography in silica gel (2-3% MeOH in DCM) to yield the title compound (0.19 g, 83%) as a pale yellow solid. LC-MS, [M+1]$^+$=438.2, {Method C: $t_R$=1.966 min}. 1H NMR (400 MHz, CHLOROFORM-d) δ ppm 7.93 (s, 1H), 7.50-7.56 (m, 2H), 7.28-7.41 (m, 6H), 7.00-7.05 (m, 1H), 6.00-6.04 (m, 1H), 5.96-5.99 (m, 1H), 5.57 (s, 1H), 4.64 (dd, J=12.8, 1.8 Hz, 1H), 4.50-4.54 (m, 1H), 4.29-4.34 (m, 1H), 4.12-4.20 (m, 1H), 3.85 (s, 3H).

Step-3: Synthesis of methyl (4aR,6R,8R,8aR)-8-(4-(3-fluorophenyl)-1H-1,2,3-triazol-1-yl)-2-phenylhexahydropyrano[3,2-d][1,3]dioxine-6-carboxylate: To a degassed solution (4aR,8R,8aR)-methyl 8-(4-(3-fluorophenyl)-1H-1,2,3-triazol-1-yl)-2-phenyl-4,4a,8,8atetrahydropyrano[3,2-d][1,3]dioxine-6-carboxylate (0.22 g, 0.503 mmol) in EtOAc (8 mL), was added palladium on carbon (10% w/w, 50% wet) (54 mg, 0.05 mmol) and stirred the mixture at rt under hydrogen pressure (~1 atm) for 12 h. The reaction mixture was filtered through Celite pad, washed with excess EtOAc/MeOH (1:1, 30 mL) and filtrate was concentrated under reduced pressure to give the title compound (0.2 g, 90%) as an off-white solid. LC/MS [M+H]$^+$=440.2, {Method B: $t_R$=1.25 min}. 1H NMR (400 MHz, CHLOROFORM-d) δ ppm 7.94 (s, 1H), 7.48-7.56 (m, 2H), 7.34-7.44 (m, 6H), 6.96-7.11 (m, 1H), 5.54 (s, 1H), 5.13-5.26 (m, 1H), 4.50 (dd, J=12.5, 1.5 Hz, 1H), 4.27-4.42 (m, 2H), 4.03-4.20 (m, 1H), 3.82 (s, 3H), 3.70 (d, J=1.5 Hz, 1H), 2.58-2.69 (m, 1H), 2.34-2.42 (m, 1H).

Step-4: Synthesis of (4aR,6R,8R,8aR)-8-(4-(3-fluorophenyl)-1H-1,2,3-triazol-1-yl)-2-phenylhexahydropyrano[3,2-d][1,3]dioxine-6-carboxylic acid: To a stirred solution of (4aR,6R,8R,8aR)-methyl8-(4-(3-fluorophenyl)-1H-1,2,3-triazol-1-yl)-2-phenylhexahydropyrano[3,2-d][1,3]dioxine-6-carboxylate (0.2 g, 0.455 mmol) in THF (8 mL), Water (2.0 mL), LiOH (0.044 g, 1.821 mmol) was added at rt and the stirring continued for 2 h. After confirmation of completion of reaction with LCMS, tetrahydrofuran was removed under reduced pressure. The residue was diluted with water (100 mL) and pH adjusted to approx 2-3 using 1.5N HCl solution. The precipitated solid was filtered and washed with water and dried under reduced pressure to yield the title compound (0.17 g, 88%) as an off-white solid. LC/MS [M+H]$^+$=426.2, {Method A: $t_R$=0.79 min}.

EXAMPLE 1a AND 1b

Synthesis of (2R, 3R, 4S, 5R, 6R)-4-(4-(3-fluorophenyl)-1H-1,2,3-triazol-1-yl)-N-((1S,2R,3R)-3-(4-(3-fluorophenyl)-1H-1,2,3-triazol-1-yl)-2-hydroxycyclohexyl)-5-hydroxy-6-(hydroxymethyl)-3-methoxytetrahydro-2H-pyran-2-carboxamide
(Isomer 1 and Isomer 2)

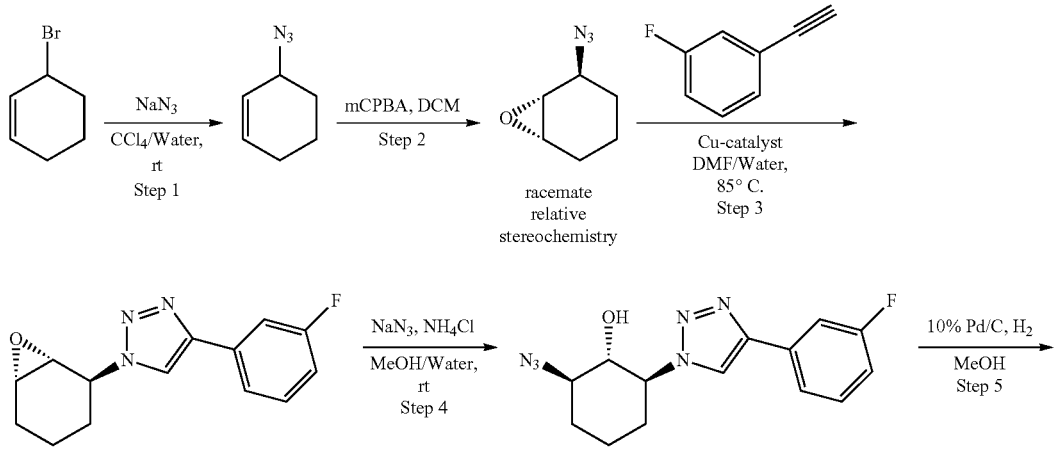

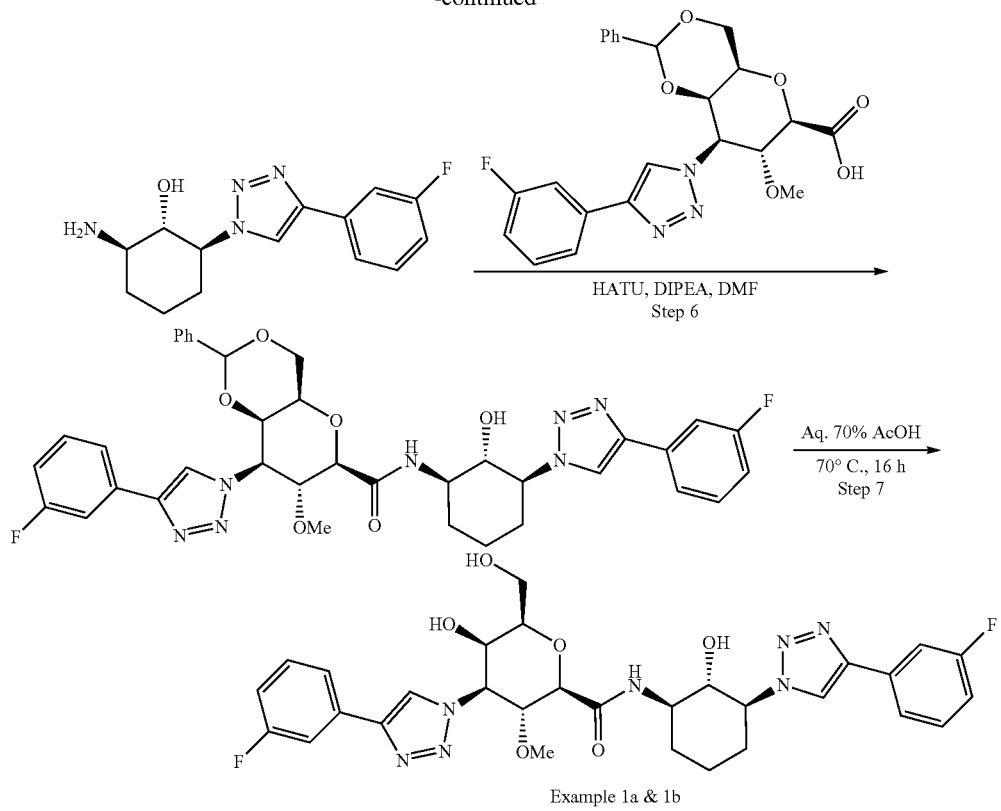

Example 1a & 1b

Step-1: Synthesis of 3-azidocyclohex-1-ene: To a stirred solution of 3-bromocyclohex-1-ene (7.1 mL, 62.1 mmol) in mixture of $CCl_4$ (100 mL)/water (100 mL) was added sodium azide (14.1 g, 217 mmol) at rt and stirred for 48 h. Aq. layer was separated and extracted with DCM (2×50 mL). The combined organic extracts were washed with water, brine, dried over sodium sulphate and concentrated to give 3-azidocyclohex-1-ene (6.6 g, 86%) as pale yellow liquid. $^1$H NMR (400 MHz, CHLOROFORM-d) δ ppm 5.94-6.07 (m, 1H), 5.66-5.75 (m, 1H), 3.83-3.92 (m, 1H), 1.96-2.17 (m, 2H), 1.84-1.94 (m, 1H), 1.69-1.80 (m, 2H), 1.57-1.68 (m, 1H).

Step-2: Synthesis of (1R,2R,6S)-2-azido-7-oxabicyclo[4.1.0]heptane (racemate): To a solution of 3-azidocyclohex-1-ene (5.5 g, 44.7 mmol) in dichloromethane (200 mL) was added mCPBA (15.4 g, 67.0 mmol) (dissolved in 20 mL DCM) at 0° C. The reaction mixture was allowed to reach rt and stirred for 16 h. The reaction mixture was cooled to 0° C., precipitated solid was filtered and washed with DCM (50 mL). The filtrate was washed with sat. $Na_2SO_3$ solution, aq. 10% $NaHCO_3$ solution, brine solution, dried over sodium sulphate and concentrated to give crude product. The crude residue was purified by flash chromatography (0-2% EtOAc in n-hexane) to afford (1R,2R,6S)-2-azido-7-oxabicyclo[4.1.0]heptane (1.9 g, 30%, cis-isomer) and (1S,2R,6R)-2-azido-7-oxabicyclo[4.1.0]heptane (2.9 g, 46%, trans isomer).

Cis-isomer: $^1$H NMR (400 MHz, CHLOROFORM-d) δ ppm 3.50-3.66 (m, 1H), 3.32 (dd, J=4.0, 2.0 Hz, 1H), 3.25-3.28 (m, 1H), 1.77-1.97 (m, 2H), 1.58-1.74 (m, 3H), 1.19-1.38 (m, 1H).

Trans-isomer: $^1$H NMR (400 MHz, CHLOROFORM-d) δ ppm 3.83 (t, J=6.8 Hz, 1H), 3.19-3.28 (m, 1H), 3.09 (d, J=3.5 Hz, 1H), 1.97-2.08 (m, 1H), 1.76-1.93 (m, 2H), 1.45-1.53 (m, 1H), 1.28-1.40 (m, 2H).

Step-3: Synthesis of 1-((1S,2R,6R)-7-oxabicyclo[4.1.0]heptan-2-yl)-4-(3-fluorophenyl)-1H-1,2,3-triazole (racemate): To a solution of (1S,2R,6R)-2-azido-7-oxabicyclo[4.1.0]heptane (0.5 g, 3.59 mmol) in DMF (5 mL) and water (1.5 mL) was added sodium ascorbate (0.71 g, 3.59 mmol), copper(II) sulfate pentahydrate (0.81 g, 3.23 mmol) and 3-fluorophenylacetylene (1.7 mL, 14.37 mmol) at rt. The reaction mixture was heated at 85° C. for 30 min. The reaction mixture was cooled to rt, diluted with 1:1 DCM (50 mL) and water (50 mL) and stirred at rt for 15 min. The reaction mixture was filtered through Celite pad and washed with DCM (20 mL). From the filtrate, organic layer was separated and aqueous layer re-extracted with DCM (2×20 mL). The combined organic extracts were washed with water, brine, dried over sodium sulphate and concentrated to give crude residue. The crude residue was purified by flash chromatography (40-50% EtOAc in n-hexane) to afford 1-((1S,2R,6R)-7-oxabicyclo[4.1.0]heptan-2-yl)-4-(3-fluorophenyl)-1H-1,2,3-triazole (0.53 g, 57%) as pale yellow solid. LC/MS $[M+H]^+$=260.2, $t_R$=2.266 min (Method C).

Step-4: Synthesis of (1R,2R,6S)-2-azido-6-(4-(3-fluorophenyl)-1H-1,2,3-triazol-1-yl)cyclohexanol (racemate): To a solution of 1-((1R,2S,6S)-7-oxabicyclo[4.1.0]heptan-2-yl)-4-(3-fluorophenyl)-1H-1,2,3-triazole (200 mg, 0.771 mmol) in MeOH (16 mL) and water (4.00 mL) was added ammonium chloride (103 mg, 1.928 mmol) and sodium azide (251 mg, 3.86 mmol) at rt. The reaction mixture was heated at 75° C. for 16 h. The reaction mixture was cooled to rt, MeOH was removed under reduced pressure and extracted with EtOAc (3×25 mL). The combined organic extracts were washed with water, brine, dried over sodium sulphate and concentrated under reduced pressure to give crude residue. The crude residue was purified by flash chromatography (20-25% EtOAc in n-hexane) to afford (1R,2R,6S)-2-azido-6-(4-(3-fluorophenyl)-1H-1,2,3-triazol-1-yl)cyclohexanol (0.22 g, 98%) as an off-white solid. LC/MS [M+H]$^+$=303.2, $t_R$=1.699 min (Method F).

Step-5: Synthesis of (1S,2R,6S)-2-amino-6-(4-(3-fluorophenyl)-1H-1,2,3-triazol-1-yl)cyclohexanol (racemate): To a degassed solution of (1R,2R,6S)-2-azido-6-(4-(3-fluorophenyl)-1H-1,2,3-triazol-1-yl)cyclohexanol (210 mg, 0.695 mmol) in MeOH (20 mL) was added palladium on carbon (10% w/w, 50% wet) (74 mg, 0.069 mmol) and stirred the mixture at rt under hydrogen pressure (~1 atm) for 2 h. The reaction mixture was filtered through Celite pad, washed with excess MeOH (10 mL) and filtrate was concentrated under reduced pressure to give (1S,2R,6S)-2-amino-6-(4-(3-fluorophenyl)-1H-1,2,3-triazol-1-yl)cyclohexanol (170 mg, 71%). LC/MS [M+H]$^+$=277.0, $t_R$=1.255 min (Method F).

Step-6: Synthesis of ((2R,3R,4S,5R,6R)-4-(4-(3-fluorophenyl)-1H-1,2,3-triazol-1-yl)-N-((1R,2S,3S)-3-(4-(3-fluorophenyl)-1H-1,2,3-triazol-1-yl)-2-hydroxycyclohexyl)-5-hydroxy-6-(hydroxymethyl)-3-methoxytetrahydro-2H-pyran-2-carboxamide: To a solution of (2S,4aR,6R,7R,8R,8aR)-8-(4-(3-fluorophenyl)-1H-1,2,3-triazol-1-yl)-7-methoxy-2-phenylhexahydropyrano[3,2-d][1,3]dioxine-6-carboxylic acid (50 mg, 0.110 mmol) (50 mg, 0.110 mmol) in DMF (2 mL) was added DIPEA (0.06 mL, 0.329 mmol) and HATU (62.6 mg, 0.165 mmol) at rt and stirred for 15 min. Then (1S,2R,6S)-2-amino-6-(4-(3-fluorophenyl)-1H-1,2,3-triazol-1-yl)cyclohexanol (36.4 mg, 0.132 mmol) was added and stirred the mixture at rt for 1 h. The reaction mixture was quenched with ice cold water (10 mL) and stirred for 15 min. The resultant solid was filtered, washed with excess water and residue was dried to afford diastereomeric mixture of crude residue. The crude residue was further purified by prep-HPLC [Method F] to obtain two isomers: Isomer 1: 20 mg, 21% yield; LC/MS [M+H]$^+$=714.2, $t_R$=2.897 min (Method C). Isomer 2: 15 mg, 19% yield; LC/MS [M+H]$^+$=714.2, $t_R$=2.878 min (Method C).

Step-7: A solution of ((4aR,6R,7R,8R,8aR)-8-(4-(3-fluorophenyl)-1H-1,2,3-triazol-1-yl)-N-((1S,2R,3R)-3-(4-(3-fluorophenyl)-1H-1,2,3-triazol-1-yl)-2-hydroxycyclohexyl)-7-methoxy-2-phenylhexahydropyrano[3,2-d][1,3]dioxine-6-carboxamide (20 mg, 0.028 mmol, isomer 1) in 70% aqueous acetic acid (5 mL) was stirred overnight at 70° C. The reaction mixture was cooled to rt and solvent was removed under reduced pressure to give crude residue. The crude product was purified by preparative LCMS (Method A) to yield Example 1a as a white solid (4.5 mg, 25% yield). LC-MS, [M+H]$^+$=626.2, [$t_R$=1.688 min, Method A] and & [$t_R$=1.710 min, Method B]. 1H NMR (400 MHz, MEOH-d4) δ ppm 8.59 (s, 1H), 8.39 (s, 1H), 7.66 (dd, J=7.8, 4.2 Hz, 2H), 7.62-7.56 (m, 2H), 7.49-7.41 (m, 2H), 7.08 (m, 2H), 4.91 (dd, J=10.8, 2.7 Hz, 1H), 4.57-4.44 (m, 1H), 4.28-4.21 (m, 1H), 4.11 (d, J=2.7 Hz, 1H), 4.03-3.89 (m, 3H), 3.82-3.77 (m, 2H), 3.75-3.69 (m, 1H), 3.19-3.12 (m, 3H), 2.24-2.12 (m, 2H), 2.05 (d, J=11.7 Hz, 1H), 1.95 (d, J=13.2 Hz, 1H), 1.68-1.54 (m, 2H). hGal3 IC$_{50}$ (ELISA)=0.7 µM; hGal3 IC$_{50}$ (HTRF)=0.29 µM.

EXAMPLE 1b

A solution of ((4aR,6R,7R,8R,8aR)-8-(4-(3-fluorophenyl)-1H-1,2,3-triazol-1-yl)-N-((1S,2R,3R)-3-(4-(3-fluorophenyl)-1H-1,2,3-triazol-1-yl)-2-hydroxycyclohexyl)-7-methoxy-2-phenylhexahydropyrano[3,2-d][1,3]dioxine-6-carboxamide (15 mg, 0.021 mmol, isomer 2) in 70% aqueous acetic acid (5 mL) was stirred overnight at 70° C. The reaction mixture was cooled to rt and solvent was removed under reduced pressure to give crude residue. The crude product was purified by preparative LCMS (Method A) to yield Example 1b as a white solid (1.1 mg, 8% yield). LC-MS, [M+H]$^+$=626.2, [$t_R$=1.690 min, Method A] and & [$t_R$=1.688 min, Method B]. 1H NMR (400 MHz, MEOH-d4) δ ppm 8.63 (s, 1H), 8.40 (s, 1H), 7.72-7.57 (m, 4H), 7.51-7.42 (m, 2H), 7.13-7.05 (m, 2H), 4.93 (dd, J=10.8, 2.7 Hz, 1H), 4.58-4.45 (m, 1H), 4.27 (t, J=9.9 Hz, 1H), 4.12 (d, J=2.4 Hz, 1H), 4.02-3.89 (m, 3H), 3.85-3.79 (m, 2H), 3.77-3.71 (m, 1H), 3.20 (s, 3H), 2.26-2.14 (m, 2H), 2.12 (br. s., 1H), 1.98 (d, J=11.5 Hz, 1H), 1.71-1.59 (m, 2H). hGal3 IC$_{50}$ (ELISA)=16 µM.

The Examples in Table 1 were prepared in an analogous fashion to Examples 1a and 1b, substituting 1-fluoro-3-ethynylbenzene with the appropriate acetylenes in the synthetic sequence

TABLE 1

| EX # | Structure (Synthetic Method A) | LCMS/$t_R$ (min); 1H NMR (400 MHz, methanol-d$_4$) | hGal-3 IC$_{50}$ (µM) |
|---|---|---|---|
| 2a | [Structure] | (M + H)$^+$ = 546.1/1.311; δ ppm 8.60 (s, 1H), 7.71 (d, J = 0.7 Hz, 1H), 7.67 (m, 1H), 7.63-7.58 (m, 1H), 7.46 (m, 1H), 7.08 (m, 1H), 4.90 (dd, J = 10.6, 2.8 Hz, 1H), 4.37 (ddd, J = 11.9, 9.9, 4.6 Hz, 1H), 4.24 (dd, J = 10.6, 9.4 Hz, 1H), 4.11 (d, J = 2.9 Hz, 1H), 3.99-3.89 (m, 2H), 3.89-3.67 (m, 4H), 3.16 (s, 2H), 2.32 (d, J = 0.5 Hz, 3H), 2.16-1.98 (m, 4H), 1.95-1.87 (m, 1H), 1.65-1.49 (m, 2H). | 0.68 |
| 2b | [Structure] | (M + H)$^+$ = 546.1/1.290; δ ppm 8.64 (s, 1H), 7.73-7.68 (m, 2H), 7.64 (d, J = 10.3 Hz, 1H), 7.52-7.44 (m, 1H), 7.14-7.07 (m, 1H), 4.94 (d, J = 2.7 Hz, 1H), 4.43-4.33 (m, 1H), 4.30-4.23 (m, 1H), 4.12 (d, J = 2.7 Hz, 2H), 3.94 (d, J = 9.3 Hz, 1H), 3.89-3.69 (m, 4H), 3.22-3.18 (m, 3H), 2.33 (s, 3H), 2.18-2.03 (m, 3H), 1.93 (d, J = 13.0 Hz, 1H), 1.66-1.54 (m, 2H). | 14.5 |

TABLE 1-continued

| EX # | Structure (Synthetic Method A) | LCMS/$t_R$ (min); $^1$H NMR (400 MHz, methanol-$d_4$) | hGal-3 IC$_{50}$ (μM) |
|---|---|---|---|
| 3a | | (M + H)$^+$ = 626.1/1.669; δ ppm 8.60 (s, 1H), 8.32 (s, 1H), 7.84 (dd, J = 8.7, 5.3 Hz, 2H), 7.66 (d, J = 8.1 Hz, 1H), 7.60 (d, J = 9.8 Hz, 1H), 7.45 (d, J = 5.9 Hz, 1H), 7.18 (t, J = 8.8 Hz, 2H), 7.08 (s, 1H), 4.60 (s, 1H), 4.53-4.42 (m, 1H), 4.29-4.18 (m, 1H), 4.10 (d, J = 2.9 Hz, 1H), 3.93 (d, J = 9.0 Hz, 2H), 3.79 (d, J = 5.6 Hz, 2H), 3.74-3.67 (m, 1H), 3.49-3.45 (m, 1H), 3.15 (s, 3H), 2.24-2.11 (m, 2H), 2.07-2.01 (m, 1H), 1.98-1.90 (m, 1H), 1.70-1.50 (m, 2H). | 0.44 |
| 3b | | (M + H)$^+$ = 626.1/1.654; δ ppm 8.62 (s, 1H), 8.32 (s, 1H), 7.84 (dd, J = 8.8, 5.1 Hz, 2H), 7.68 (d, J = 7.8 Hz, 1H), 7.61 (s, 1H), 7.46 (d, J = 5.9 Hz, 1H), 7.17 (t, J = 8.8 Hz, 2H), 7.09 (d, J = 2.4 Hz, 1H), 4.99-4.90 (m, 1H), 4.52-4.41 (m, 1H), 4.32-4.21 (m, 1H), 4.10 (d, J = 2.4 Hz, 1H), 3.98-3.86 (m, 3H), 3.81 (t, J = 3.4 Hz, 2H), 3.71 (d, J = 6.4 Hz, 1H), 3.18 (s, 3H), 2.25-2.05 (m, 3H), 1.96-1.92 (m, 1H), 1.62 (d, J = 12.0 Hz, 2H). | >100 |
| 4a | | (M + H)$^+$ = 608.1/1.624; δ ppm 8.59 (s, 1H), 8.33 (s, 1H), 7.92-7.76 (m, 2H), 7.70-7.54 (m, 2H), 7.51-7.30 (m, 3H), 7.38-7.34 (m, 1H), 7.16-7.00 (m, 1H), 4.93-4.88 (m, 1H), 4.53-4.43 (m, 1H), 4.29-4.18 (m, 1H), 4.13-4.08 (m, 1H), 4.04-3.88 (m, 3H), 3.85-3.77 (m, 2H), 3.76-3.68 (m, 1H), 3.20 (s, 3H), 2.27-1.89 (m, 4H), 1.74-1.53 (m, 2H). | 0.45 |
| 4b | | (M + H)$^+$ = 608.1/1.606; δ ppm 8.61 (s, 1H), 8.33 (s, 1H), 7.86-7.77 (m, 2H), 7.72-7.58 (m, 2H), 7.52-7.40 (m, 3H), 7.38-7.35 (m, 1H), 7.23-6.98 (m, 1H), 4.95-4.87 (m, 1H), 4.53-4.42 (m, 1H), 4.30-4.22 (m, 1H), 4.12-4.08 (m, 1H), 4.02-3.87 (m, 3H), 3.85-3.77 (m, 2H), 3.75-3.68 (m, 1H), 3.18 (s, 3H), 2.28-1.90 (m, 4H), 1.70-1.55 (m, 2H). | 3.30 |
| 5a | | (M + H)$^+$ = 638.2/1.660; δ ppm 8.60 (s, 1H), 8.34 (s, 1H), 7.69-7.58 (m, 2H), 7.51-7.31 (m, 4H), 7.12-7.02 (m, 1H), 6.92 (d, J = 7.3 Hz, 1H), 4.91 (d, J = 10.5 Hz, 1H), 4.62-4.44 (m, 2H), 4.28-4.21 (m, 1H), 4.13-3.63 (m, 10 H), 3.17 (s, 3H), 2.31-1.90 (m, 4H), 1.72-1.54 (m, 1H). | 0.40 |
| 5b | | (M + H)$^+$ = 638.2/1.647; δ ppm 8.61 (s, 1H), 8.33 (s, 1H), 7.71-7.59 (m, 2H), 7.50-7.30 (m, 4H), 7.13-7.05 (m, 1H), 6.91 (d, J = 8.1 Hz, 1H), 4.95-4.90 (m, 1H), 4.53-4.43 (m, 1H), 4.26 (t, J = 9.9 Hz, 1H), 4.11 (d, J = 2.9 Hz, 1H), 4.01-3.91 (m, 3H), 3.85 (s, 3H), 3.83-3.66 (m, 3H), 3.18 (s, 3H), 2.24-2.06 (m, 3H), 1.96-1.94 (m, 1H), 1.73-1.55 (m, 2H). | 3.03 |

EXAMPLE 6a AND 6b

Synthesis of (2R,3R,4S,5R,6R)-4-(4-(3-fluorophenyl)-1H-1,2,3-triazol-1-yl)-N-((1R,2S,3S)-3-(5-(3-fluorophenyl)-1H-1,2,3-triazol-1-yl)-2-hydroxycyclohexyl)-hydroxy-6-(hydroxymethyl)-3-methoxytetrahydro-2H-pyran-2-carboxamide (Isomer 1 and Isomer 2)

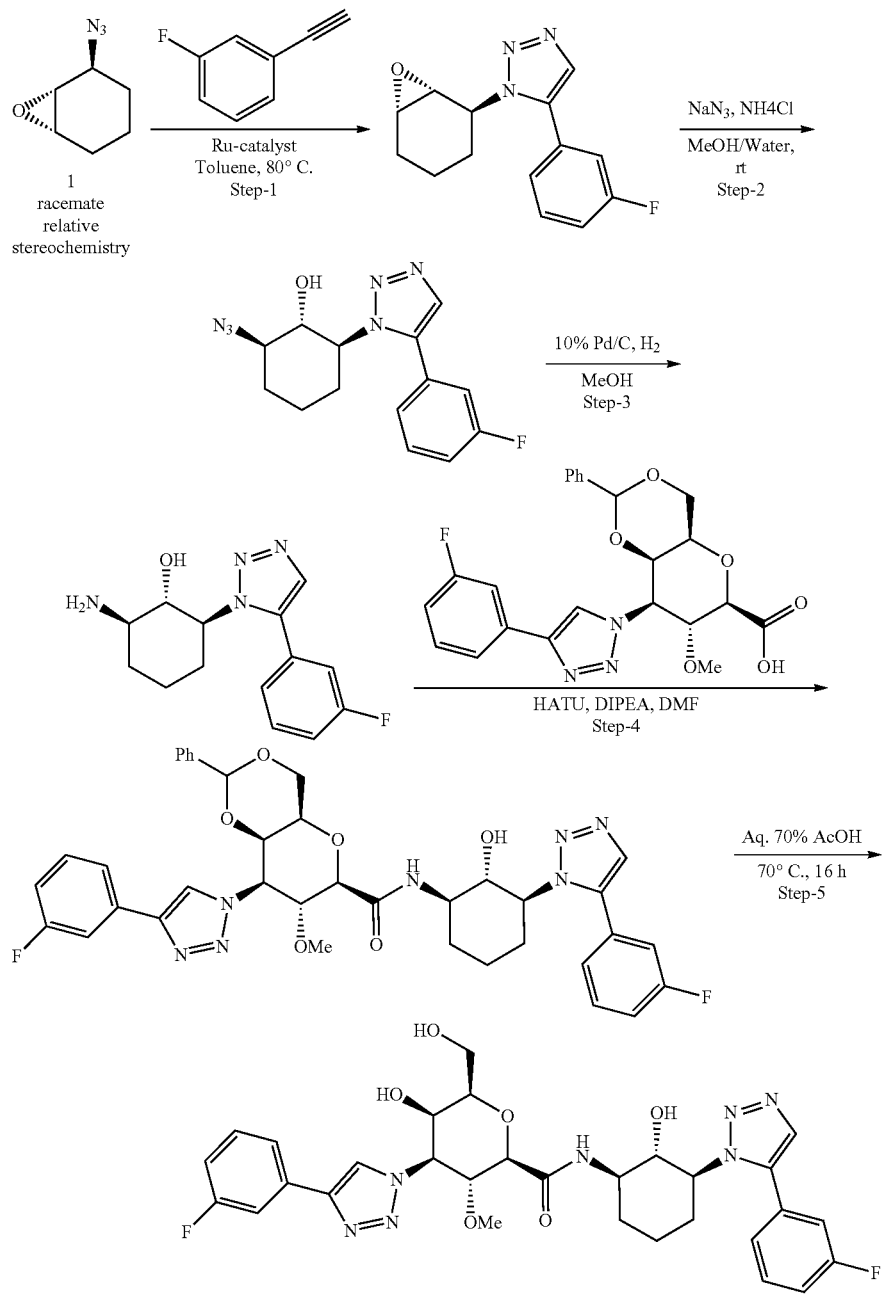

Example 6a & 6b

Step-1: Synthesis of 1-((1R,2S,6S)-7-oxabicyclo[4.1.0]heptan-2-yl)-5-(3-fluorophenyl)-1H-1,2,3-triazole (racemate): To a stirred solution of (1R,2S,6S)-2-azido-7-oxabicyclo[4.1.0]heptane (100 mg, 0.719 mmol) and 3-fluorophenylacetylene (0.34 mL, 2.87 mmol) in toluene (3 mL) was added chloro(1,5-cyclooctadiene)(pentamethylcyclopentadienyl)ruthenium (8.19 mg, 0.022 mmol). The reaction mixture was heated at 85° C. for 4 h. The reaction mixture was cooled to rt and solvent was removed under reduced pressure to give crude residue. The crude residue was purified by flash chromatography (40-50% EtOAc in n-hexane) to afford the title compound (175 mg, 92%) as an off-white solid. LC/MS [M+H]$^+$=260.2, $t_R$=2.12 min (Method C).

Step-2: Synthesis of (1R,2R,6S)-2-azido-6-(5-(3-fluorophenyl)-1H-1,2,3-triazol-1-yl)cyclohexanol (racemate): To a solution of 1-((1R,2S,6S)-7-oxabicyclo[4.1.0]heptan-2-yl)-5-(3-fluorophenyl)-1H-1,2,3-triazole (170 mg, 0.656 mmol) in MeOH (8 mL) and water (2 mL) was added ammonium chloride (88 mg, 1.639 mmol) and sodium azide (213 mg, 3.28 mmol) at rt. The reaction mixture was heated at 75° C. for 16 h. The reaction mixture was cooled to rt, MeOH was removed under reduced pressure and extracted with EtOAc (3×25 mL). The combined organic extracts were washed with water, brine, dried over sodium sulphate and concentrated under reduced pressure to give crude residue. The crude residue was purified by flash chromatography (20-25% EtOAc in n-hexane) to afford the title compound (0.15 g, 72%) as a brown solid. LC/MS [M+H]$^+$=303.5, $t_R$=1.10 min (Method E).

Step-3: Synthesis of (1S,2R,6S)-2-amino-6-(5-(3-fluorophenyl)-1H-1,2,3-triazol-1-yl)cyclohexanol (racemate): To a degassed solution of (1R,2R,6S)-2-azido-6-(5-(3-fluorophenyl)-1H-1,2,3-triazol-1-yl)cyclohexanol (150 mg, 0.496 mmol) in MeOH (10 mL) was added palladium on carbon (10% w/w, 50% wet) (53 mg, 0.050 mmol) and stirred the reaction mixture at rt under hydrogen pressure (~1 atm) for 2 h. The reaction mixture was filtered through Celite pad, washed with excess MeOH (10 mL) and filtrate was concentrated under reduced pressure to give the title compound (68 mg, 40%). LC/MS [M+H]$^+$=277.2, $t_R$=1.18 min (Method F).

Step-4: Synthesis of (4aR,6R,7R,8R,8aR)-8-(4-(3-fluorophenyl)-1H-1,2,3-triazol-1-yl)-N-((1R,2S,3S)-3-(5-(3-fluorophenyl)-1H-1,2,3-triazol-1-yl)-2-hydroxycyclohexyl)-7-methoxy-2-phenylhexahydropyrano[3,2-d][1,3]dioxine-6-carboxamide: To a solution of ((4aR,6R,7R,8R,8aR)-8-(4-(3-fluorophenyl)-1H-1,2,3-triazol-1-yl)-7-methoxy-2-phenylhexahydropyrano[3,2-d][1,3]dioxine-6-carboxylic acid (50 mg, 0.110 mmol) in DMF (2 mL) was added DIPEA (0.06 mL, 0.329 mmol) and HATU (62.6 mg, 0.165 mmol) at rt and stirred for 15 min. Then (1S,2R,6S)-2-amino-6-(5-(3-fluorophenyl)-1H-1,2,3-triazol-1-yl)cyclohexanol (36.4 mg, 0.132 mmol) was added and stirred the mixture at rt for 1 h. The reaction mixture was quenched with ice cold water (10 mL) and stirred for 15 min. The resultant solid was filtered, washed with excess water and the residue was dried to afford diastereomeric mixture of crude residue. The crude residue was further purified by prep-HPLC [Method E] to obtain isomer 1 and isomer 2.

Isomer 1: 10 mg, 13% yield; LC/MS [M+H]$^+$=714.2, $t_R$=2.461 min (Method F).

Isomer 2: 15 mg, 17% yield; LC/MS [M+H]$^+$=714.2, $t_R$=2.457 min (Method F).

Step-5: ((4aR,6R,7R,8R,8aR)-8-(4-(3-fluorophenyl)-1H-1,2,3-triazol-1-yl)-N-((1R,2S,3S)-3-(5-(3-fluorophenyl)-1H-1,2,3-triazol-1-yl)-2-hydroxycyclohexyl)-7-methoxy-2-phenylhexahydropyrano[3,2-d][1,3]dioxine-6-carboxamide (Isomer 1) (10 mg, 0.014 mmol) was suspended in aq. 70% acetic acid (3 mL, 52.4 mmol) and heated at 70° C. for 16 h. The reaction mixture was cooled to rt and concentrated under reduced pressure to give crude residue. The crude residue was purified by prep-HPLC [Method A] to afford Example 6a (2R,3R,4S,5R,6R)-4-(4-(3-fluorophenyl)-1H-1,2,3-triazol-1-yl)-N-((1R,2S,3S)-3-(5-(3-fluorophenyl)-1H-1,2,3-triazol-1-yl)-2-hydroxycyclohexyl)-5-hydroxy-6-(hydroxymethyl)-3-methoxytetrahydro-2H-pyran-2-carboxamide Isomer 1 (2.9 mg, 33%). LC/MS [M+H]$^+$=626.1, $t_R$=1.667 min (Method A); 1H NMR (400 MHz, MEOH-d4) δ ppm 8.63 (s, 1H), 7.80 (s, 1H), 7.70 (d, J=7.8 Hz, 1H), 7.66-7.54 (m, 2H), 7.51-7.38 (m, 3H), 7.29 (td, J=8.6, 2.4 Hz, 1H), 7.10 (td, J=8.6, 2.4 Hz, 1H), 4.93 (dd, J=10.6, 2.8 Hz, 1H), 4.38-4.30 (m, 1H), 4.29-4.16 (m, 2H), 4.12 (d, J=2.7 Hz, 1H), 3.94 (d, J=9.3 Hz, 1H), 3.92-3.79 (m, 3H), 3.77-3.69 (m, 1H), 3.19 (s, 3H), 2.28-2.16 (m, 1H), 2.06 (d, J=10.8 Hz, 2H), 1.89 (d, J=13.7 Hz, 1H), 1.67-1.44 (m, 2H). hGal3 IC50=27 μM.

EXAMPLE 6b (2S,4aR,6R,7R,8R,8aR)-8-(4-(3-fluorophenyl)-1H-1,2,3-triazol-1-yl)-N-((1R,2S,3S)-3-(5-(3-fluorophenyl)-1H-1,2,3-triazol-1-yl)-2-hydroxycyclohexyl)-7-methoxy-2-phenylhexahydropyrano[3,2-d][1,3]dioxine-6-carboxamide (Isomer 2) (15 mg, 0.021 mmol) was suspended in 70% Aq. acetic acid (5 mL, 87 mmol) and heated at 70° C. for 16 h. The reaction mixture was cooled to rt and concentrated under reduced pressure to give crude residue. The crude residue was purified by prep-HPLC [Method A] to afford (2R,3R,4S,5R,6R)-4-(4-(3-fluorophenyl)-1H-1,2,3-triazol-1-yl)-N-((1R,2S,3S)-3-(5-(3-fluorophenyl)-1H-1,2,3-triazol-1-yl)-2-hydroxycyclohexyl)-5-hydroxy-6-(hydroxymethyl)-3-methoxytetrahydro-2H-pyran-2-carboxamide Isomer 2 (5.5 mg, 42%). LC/MS [M+H]$^+$=626.1, $t_R$=1.683 min (Method A); $^1$H NMR (400 MHz, MEOH-d4) δ ppm 8.61 (s, 1H), 7.81 (s, 1H), 7.68 (d, J=8.1 Hz, 1H), 7.65-7.55 (m, 2H), 7.51-7.40 (m, 3H), 7.32-7.26 (m, 1H), 7.14-7.07 (m, 1H), 4.92 (dd, J=10.9, 3.1 Hz, 1H), 4.39-4.31 (m, 1H), 4.29-4.16 (m, 2H), 4.12 (d, J=2.7 Hz, 1H), 3.94 (d, J=9.3 Hz, 1H), 3.90 (br. s., 1H), 3.85-3.79 (m, 2H), 3.77-3.72 (m, 1H), 3.17 (s, 3H), 2.28-2.16 (m, 1H), 2.11-1.98 (m, 2H), 1.88 (d, J=13.7 Hz, 1H), 1.63-1.47 (m, 2H). hGal3 IC$_{50}$=0.90 μM.

Synthetic Scheme for Indazole Derivatives:

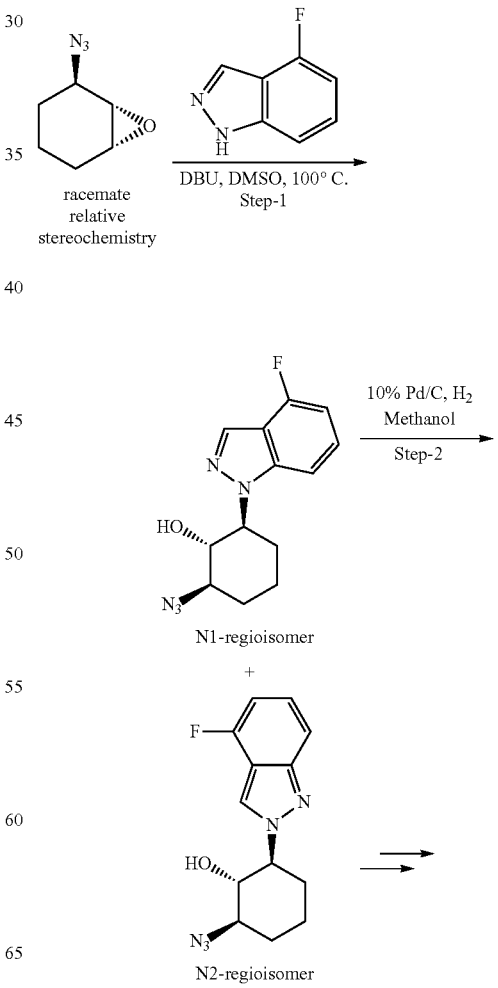

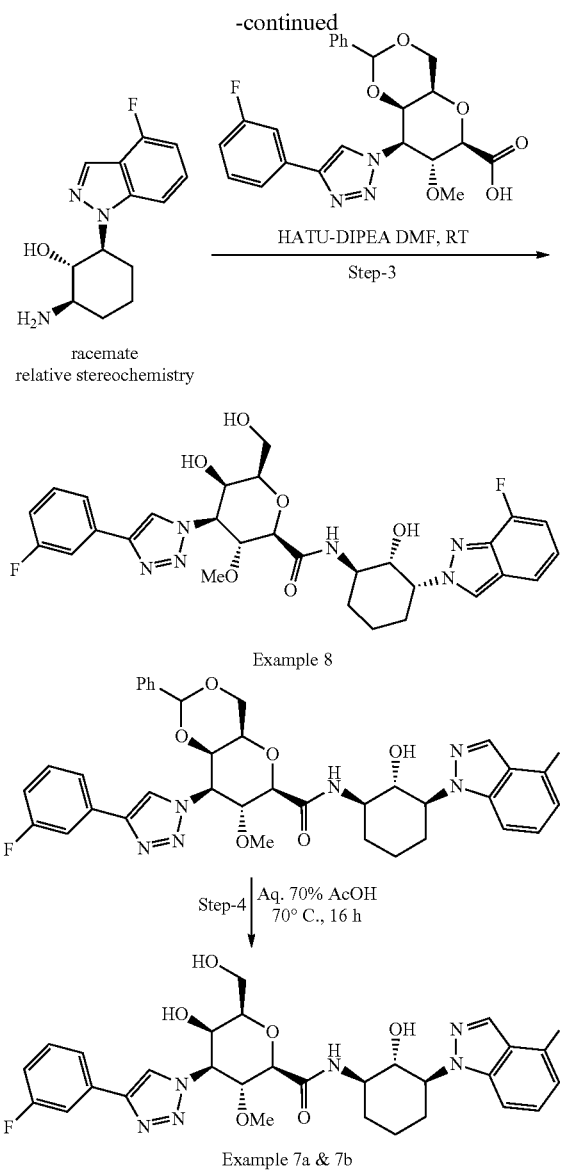

Example 8

Example 7a & 7b

Step-1: Synthesis of (1R,2R,6S)-2-azido-6-(4-fluoro-1H-indazol-1-yl)cyclohexanol and (1R,2R,6S)-2-azido-6-(4-fluoro-2H-indazol-2-yl)cyclohexanol (racemate): To a solution of (1S,2R,6R)-2-azido-7-oxabicyclo[4.1.0]heptane (300 mg, 2.156 mmol) and 4-fluoro-1H-indazole (308 mg, 2.264 mmol) in DMSO (3 mL) was added DBU (0.975 mL, 6.47 mmol) at rt. The reaction mixture was heated at 100° C. for 16 h. The reaction mixture was cooled to rt, extracted with EtOAc (3×30 mL), washed with water, brine, dried over sodium sulphate and concentrated under reduced pressure to give crude product. The crude residue was purified by prep-HPLC (Method B) to afford N1-regioisomer (1R,2R, 6S)-2-azido-6-(4-fluoro-1H-indazol-1-yl)cyclohexanol (120 mg, 20%) and N2-regioisomer (1R,2R,6S)-2-azido-6-(4-fluoro-2H-indazol-2-yl)cyclohexanol (150 mg, 20%).

N1-regioisomer: $^1$H NMR (400 MHz, CHLOROFORM-d) δ ppm 8.12 (d, J=0.8 Hz, 1H), 7.16-7.39 (m, 2H), 6.76-6.83 (m, 1H), 4.29-4.38 (m, 1H), 4.15-4.23 (m, 1H), 3.48-3.57 (m, 1H), 2.39 (d, J=3.5 Hz, 1H), 2.13-2.20 (m, 1H), 2.04-2.11 (m, 1H), 1.94-2.00 (m, 1H), 1.43-1.68 (m, 3H). LC/MS [M+H]$^+$=276.2, $t_R$=1.98 min (Method F).

N2-regioisomer: $^1$H NMR (400 MHz, CHLOROFORM-d) δ ppm 8.06 (d, J=0.8 Hz, 1H), 7.43 (s, 1H), 7.11-7.25 (m, 1H), 6.66-6.73 (m, 1H), 4.19-4.36 (m, 1H), 4.06 (t, J=9.6 Hz, 1H), 3.46-3.57 (m, 1H), 2.20-2.26 (m, 1H), 2.09-2.17 (m, 2H), 1.96-2.02 (m, 1H), 1.50-1.59 (m, 2H). LC/MS [M+H]$^+$=276.2, $t_R$=2.12 min (Method C).

Step-2: Synthesis of (1S,2R,6S)-2-amino-6-(4-fluoro-1H-indazol-1-yl)cyclohexanol (racemate): To a degassed solution of (1R,2R,6S)-2-azido-6-(4-fluoro-1H-indazol-1-yl)cyclohexanol (100 mg, 0.363 mmol) in MeOH (5 mL) was added palladium on carbon (10% w/w) (39 mg, 0.036 mmol) and stirred the reaction mixture at rt under hydrogen pressure (~1 atm) for 2 h. The reaction mixture was filtered through Celite pad, washed with excess MeOH (10 mL) and filtrate was concentrated under reduced pressure to give (1S,2R,6S)-2-amino-6-(4-fluoro-1H-indazol-1-yl)cyclohexanol (65 mg, 62%). LC/MS [M+H]$^+$=250.0, $t_R$=1.26 min (Method F).

Step-3: Synthesis of (4aR,6R,7R,8R,8aR)-N-((1R,2S,3S)-3-(4-fluoro-1H-indazol-1-yl)-2-hydroxycyclohexyl)-8-(4-(3-fluorophenyl)-1H-1,2,3-triazol-1-yl)-7-methoxy-2-phenylhexahydropyrano[3,2-d][1,3]dioxine-6-carboxamide: To a solution of (4aR,6R,7R,8R,8aR)-8-(4-(3-fluorophenyl)-1H-1,2,3-triazol-1-yl)-7-methoxy-2-phenylhexahydropyrano[3,2-d][1,3]dioxine-6-carboxylic acid (50 mg, 0.110 mmol) in DMF (5 mL) was added DIPEA (0.19 mL, 1.098 mmol) and HATU (83 mg, 0.220 mmol) at rt and stirred for 15 min. Then (1S,2R,6S)-2-amino-6-(4-fluoro-1H-indazol-1-yl)cyclohexanol (racemate) (28 mg, 0.110 mmol) was added and stirred the mixture at rt for 1 h. The reaction mixture was quenched with ice cold water (10 mL) and stirred for 15 min. The resultant solid was filtered, washed with excess water and residue was dried to afford diastereomeric mixture of crude residue. The crude residue was purified by prep-HPLC [Method E] to obtain Isomer 1 and Isomer 2.

Isomer 1: 21 mg, 27% yield; LC/MS [M+H]$^+$=687.2, $t_R$=2.54 min (Method F).

Isomer 2: 20 mg, 26% yield; LC/MS [M+H]$^+$=6872, $t_R$=2.55 min (Method F).

Step-4: Synthesis of (2R,3R,4S,5R,6R)-N-((1R,2S,3S)-3-(4-fluoro-1H-indazol-1-yl)-2-hydroxycyclohexyl)-4-(4-(3-fluorophenyl)-1H-1,2,3-triazol-1-yl)-5-hydroxy-6-(hydroxymethyl)-3-methoxytetrahydro-2H-pyran-2-carboxamide (Isomer 1 and 2): (4aR,6R,7R,8R,8aR)-N-((1R,2S,3S)-3-(4-fluoro-1H-indazol-1-yl)-2-hydroxycyclohexyl)-8-(4-(3-fluorophenyl)-1H-1,2,3-triazol-1-yl)-7-methoxy-2-phenylhexahydropyrano[3,2-d][1,3]dioxine-6-carboxamide (Isomer-1) (20 mg, 0.029 mmol) was suspended in aq. 70% acetic acid (5 mL) and heated at 70° C. for 16 h. The reaction mixture was cooled to rt and concentrated under reduced pressure to give crude residue. The crude residue was purified by prep-HPLC [Method A] to afford Example 7a, (2R,3R,4S,5R,6R)-N-((1R,2S,3S)-3-(4-fluoro-1H-indazol-1-yl)-2-hydroxycyclohexyl)-4-(4-(3-fluorophenyl)-1H-1,2,3-triazol-1-yl)-5-hydroxy-6-(hydroxymethyl)-3-methoxytetrahydro-2H-pyran-2-carboxamide Isomer 1 (7.8 mg, 45%). LC/MS [M+H]$^+$=599.1, $t_R$=1.77 min (Method A); 1H NMR (400 MHz, MEOH-d4) δ=8.60 (s, 1H), 8.14 (s, 1H), 7.68 (d, J=8.1 Hz, 1H), 7.62 (d, J=10.3 Hz, 1H), 7.49-7.43 (m, 2H), 7.39-7.34 (m, 1H), 7.12-7.07 (m, 1H), 6.83-6.81 (m, 1H), 4.93 (dd, J=10.9, 2.8 Hz, 1H), 4.57 (br. s, 1H), 4.27-4.12 (m, 1H), 4.13-4.05 (m, 3H), 4.03 (d, J=9.3 Hz, 1H), 3.93-3.73 (m, 3H), 3.16 (s, 3H), 2.16-1.92 (m, 4H), 1.71-1.52 (m, 2H). hGal3 IC50=0.64 μM.

EXAMPLE 7b

Prepared in a similar fashion as described for Example 7a, Isomer 1 using (4aR,6R,7R,8R,8aR)-N-((1R,2S,3S)-3-(4-fluoro-1H-indazol-1-yl)-2-hydroxycyclohexyl)-8-(4-(3-fluorophenyl)-1H-1,2,3-triazol-1-yl)-7-methoxy-2-phenylhexahydropyrano[3,2-d][1,3]dioxine-6-carboxamide (Isomer 2) (20 mg, 0.029 mmol). The crude residue was purified by prep-HPLC [Method A] to afford (2R,3R,4S,5R,6R)-N-((1R,2S,3S)-3-(4-fluoro-1H-indazol-1-yl)-2-hydroxycyclohexyl)-4-(4-(3-fluorophenyl)-1H-1,2,3-triazol-1-yl)-5-hydroxy-6-(hydroxymethyl)-3-methoxytetrahydro-2H-pyran-2-carboxamide Isomer 2 (8.1 mg, 46%). LC/MS [M+H]$^+$=599.1, $t_R$=1.747 min (Method A); $^1$H NMR (400 MHz, MEOH-d4) δ ppm 8.63 (s, 1H), 8.13 (s, 1H), 7.70 (d, J=7.8 Hz, 1H), 7.64 (d, J=10.3 Hz, 1H), 7.50-7.43 (m, 2H), 7.38-7.33 (m, 1H), 7.12-7.07 (m, 1H), 6.82-6.80 (m, 1H), 4.93 (dd, J=10.6, 2.8 Hz, 1H), 4.60-4.47 (m, 1H), 4.28 (t, J=10.0 Hz, 1H), 4.15-3.98 (m, 3H), 3.94 (d, J=9.3 Hz, 1H), 3.87-3.76 (m, 2H), 3.76-3.67 (m, 1H), 3.18 (s, 3H), 2.22-1.89 (m, 4H), 1.77-1.56 (m, 2H). hGal3 IC$_{50}$=23 μM.

EXAMPLE 8

Synthesis of (2R,3R,4S,5R,6R)-N-((1R,2S,3S)-3-(4-fluoro-2H-indazol-2-yl)-2-hydroxycyclohexyl)-4-(4-(3-fluorophenyl)-1H-1,2,3-triazol-1-yl)-5-hydroxy-6-(hydroxymethyl)-3-methoxytetrahydro-2H-pyran-2-carboxamide Step 1: Synthesis of (1S,2R,6S)-2-amino-6-(4-fluoro-2H-indazol-2-yl)cyclohexanol (racemate): To a degassed solution of (1R,2R,6S)-2-azido-6-(4-fluoro-2H-indazol-2-yl)cyclohexanol (150 mg, 0.545 mmol)) in MeOH (10 mL) was added palladium on carbon (10% w/w) (58 mg, 0.054 mmol) and stirred the reaction mixture at rt under hydrogen pressure (~1 atm) for 2 h. The reaction mixture was filtered through Celite pad, washed with excess MeOH (10 mL) and filtrate was concentrated under reduced pressure to give the title compound (80 mg, 45%) as an off white solid. LC/MS [M+H]$^+$=250.2, $t_R$=0.74 min (Method C).

Step-2: Synthesis of (4aR,6R,7R,8R,8aR)-N-((1R,2S,3S)-3-(4-fluoro-2H-indazol-2-yl)-2-hydroxycyclohexyl)-8-(4-(3-fluorophenyl)-1H-1,2,3-triazol-1-yl)-7-methoxy-2-phenylhexahydropyrano[3,2-d][1,3]dioxine-6-carboxamide: To a solution of (4aR,6R,7R,8R,8aR)-8-(4-(3-fluorophenyl)-1H-1,2,3-triazol-1-yl)-7-methoxy-2-phenylhexahydropyrano[3,2-d][1,3]dioxine-6-carboxylic acid (50 mg, 0.110 mmol) in DMF (5 mL) was added DIPEA (0.19 mL, 1.098 mmol) and HATU (83 mg, 0.220 mmol) at rt and stirred for 15 min. Then (1S,2R,6S)-2-amino-6-(4-fluoro-2H-indazol-2-yl)cyclohexanol (racemate) (27.4 mg, 0.110 mmol) was added at rt and stirred for 1 h. The reaction mixture was quenched with ice cold water (10 mL) and stirred for 15 min. The resultant solid was filtered, washed with excess water and residue was dried to afford diastereomeric mixture of crude residue. The crude residue was further purified by prep-HPLC [Method E] to obtain Isomer 1 and Isomer 2.

Isomer 1: 10 mg, 13% yield; LC/MS [M+H]$^+$=687.0, $t_R$=2.318 min (Method F).

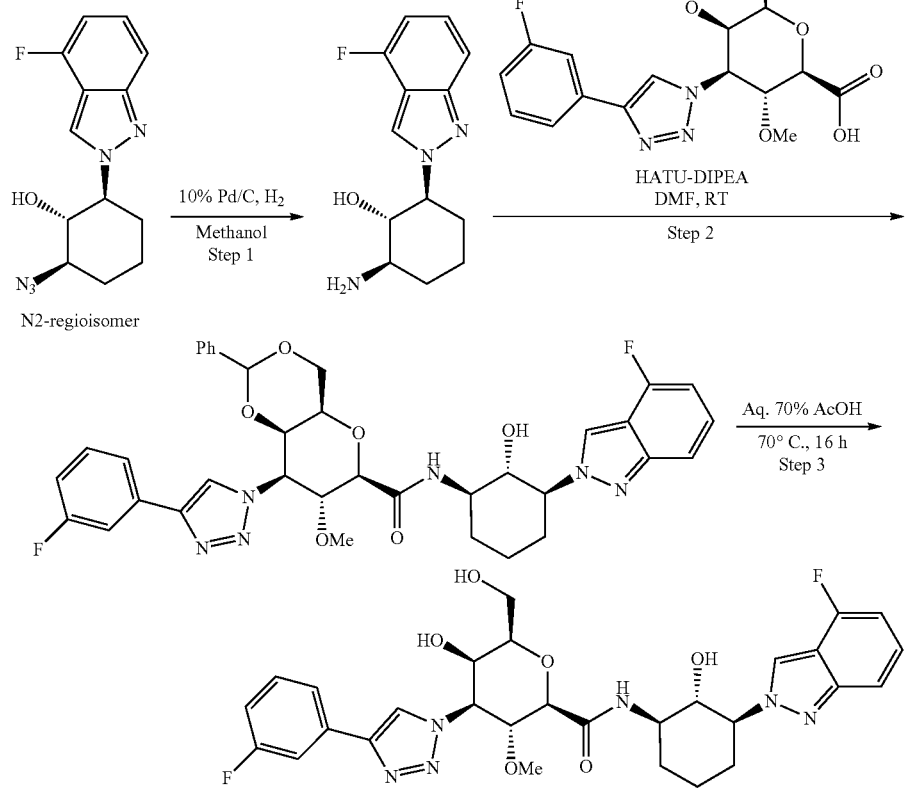

Example 8

Isomer 2: 12 mg, 15% yield; LC/MS [M+H]+=687.2, $t_R$=2.328 min (Method F).

Step-3: (4aR,6R,7R,8R,8aR)-N-((1R,2S,3S)-3-(4-fluoro-2H-indazol-2-yl)-2-hydroxycyclohexyl)-8-(4-(3-fluorophenyl)-1H-1,2,3-triazol-1-yl)-7-methoxy-2-phenylhexahydropyrano[3,2-d][1,3]dioxine-6-carboxamide (Isomer 1) (10 mg, 0.015 mmol) was suspended in aq. 70% acetic acid (5 mL) and heated at 70° C. for 16 h. The reaction mixture was cooled to rt and concentrated under reduced pressure to give crude residue. The crude residue was purified by prep-HPLC [Method A] to afford Example 8 (2R,3R,4S,5R,6R)-N-((1R,2S,3S)-3-(4-fluoro-2H-indazol-2-yl)-2-hydroxycyclohexyl)-4-(4-(3-fluorophenyl)-1H-1,2,3-triazol-1-yl)-5-hydroxy-6-(hydroxymethyl)-3-methoxytetrahydro-2H-pyran-2-carboxamide (1.6 mg, 18%). LC/MS [M+H]+=599.1, $t_R$=1.685 min (Method A); 1H NMR (400 MHz, MEOH-$d_4$) δ=8.60 (s, 1H), 8.37 (s, 1H), 7.67 (d, J=7.6 Hz, 1H), 7.61 (d, J=10.0 Hz, 1H), 7.50-7.41 (m, 2H), 7.29-7.21 (m, 1H), 7.09 (t, J=8.4 Hz, 1H), 6.72 (dd, J=10.5, 7.6 Hz, 1H), 4.92 (dd, J=10.8, 2.4 Hz, 1H), 4.46 (br. s., 1H), 4.25 (t, J=9.9 Hz, 1H), 4.12 (d, J=2.2 Hz, 1H), 4.07-3.91 (m, 3H), 3.86-3.67 (m, 3H), 3.17 (s, 3H), 2.31-2.13 (m, 2H), 2.10-1.90 (m, 2H), 1.72-1.55 (m, 2H). hGal3 IC50=0.57 μM.

EXAMPLE 9a AND 9b

Synthesis of (2R,3R,4S,5R,6R)-4-(4-(3-fluorophenyl)-1H-1,2,3-triazol-1-yl)-N-((1S,2R,3R)-3-(3-(3-fluorophenyl)-1H-1,2,4-triazol-1-yl)-2-hydroxycyclohexyl)-5-hydroxy-6-(hydroxymethyl)-3-methoxytetrahydro-2H-pyran-2-carboxamide Isomers 1 and 2

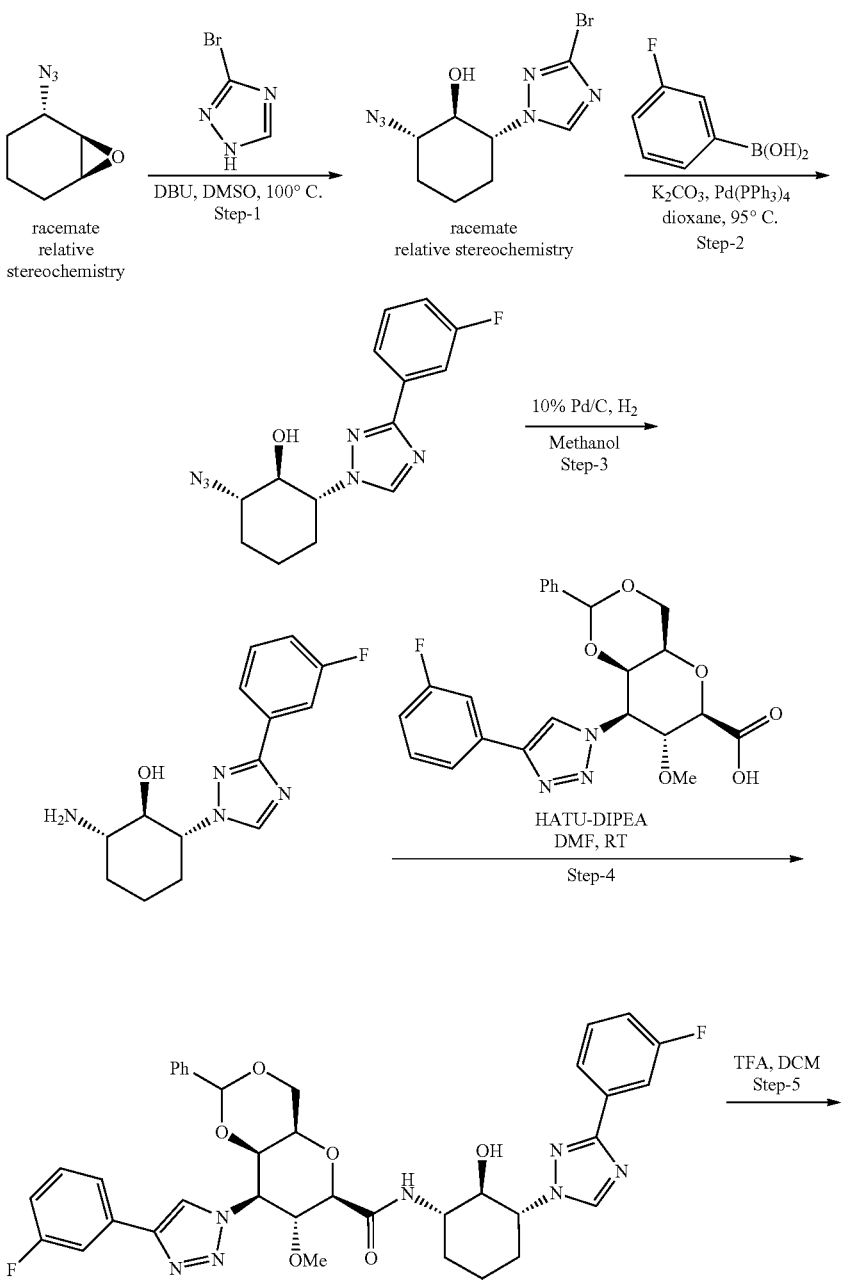

-continued

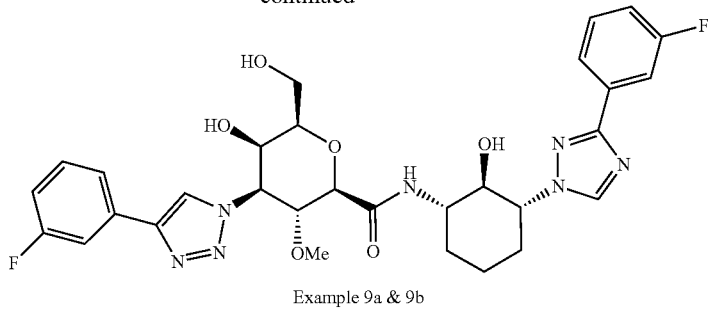

Example 9a & 9b

Step-1: Synthesis of (1R,2R,6S)-2-azido-6-(3-bromo-1H-1,2,4-triazol-1-yl)cyclohexanol (racemate): To a solution of (1S,2R,6R)-2-azido-7-oxabicyclo [4.1.0]heptane (200 mg, 1.437 mmol) and 3-bromo-1H-1,2,4-triazole (213 mg, 1.437 mmol) in DMSO (2 mL) was added DBU (0.650 mL, 4.31 mmol) and heated at 100° C. for 16 h. After confirmation of completion of reaction by LCMS, the reaction mass was diluted with EtOAc (20 mL) and Water (20 mL). The organic layer was separated and aqueous layer was re-extracted with EtAOc (2×10 mL). Combined organic extracts were washed with brine (20 mL) and dried over $Na_2SO_4$. The solvent was removed under reduced pressure and the crude was purified by flash chromatography (60-120 mesh silica column, 50-60% ethyl acetate in pet ether). The concentrate after purification yielded (1R,2R,6S)-2-azido-6-(3-bromo-1H-1,2,4-triazol-1-yl)cyclohexanol (143 mg, 0.5 mmol, 35%) as an off-white solid. LC-MS, $[M+2]^+$=289.0, {Method F, tR:1.030 min, ELSD detector}.

Step-2: Synthesis of (1R,2R,6S)-2-azido-6-(3-(3-fluorophenyl)-1H-1,2,4-triazol-1-yl)cyclohexanol (racemate): To a solution of (1R,2R,6S)-2-azido-6-(3-bromo-1H-1,2,4-triazol-1-yl)cyclohexanol (110 mg, 0.383 mmol), (3-fluorophenyl)boronic acid (64.3 mg, 0.460 mmol) in 1,4-Dioxane (3 mL) and Water (0.450 mL) was added $K_2CO_3$ (116 mg, 0.843 mmol). The reaction mixture was degassed with $N_2$ and added $Pd(Ph_3P)_4$ (22.14 mg, 0.019 mmol) under $N_2$. The vial was sealed and heated at 95° C. for 16 h. The reaction mixture was cooled to rt and solvent was removed under reduced pressure to get the crude residue which was purified by flash chromatography (60-120 silicagel, 80-90% ethyl acetate in pet ether) to afford (1R,2R,6S)-2-azido-6-(3-(3-fluorophenyl)-1H-1,2,4-triazol-1-yl)cyclohexanol (58 mg, 47%) as an off-white solid. LC-MS, $[M+H]^+$=303.2, $t_R$:2.256 min {Method C}.

Step-3: Synthesis of (1S,2R,6S)-2-amino-6-(3-(3-fluorophenyl)-1H-1,2,4-triazol-1-yl)cyclohexanol (racemate): Prepared in a similar fashion as described in Example 1a, Step-5 using (1R,2R,6S)-2-azido-6-(3-(3-fluorophenyl)-1H-1,2,4-triazol-1-yl)cyclohexanol to afford (1S,2R,6S)-2-amino-6-(3-(3-fluorophenyl)-1H-1,2,4-triazol-1-yl)cyclohexanol (0.048 g, 87% yield) as an off-white solid. LC-MS, $[M+H]^+$=277.2 {$t_R$:0.730 min, Method E}.

Step-4: Synthesis of (4aR,6R,7R,8R,8aR)-8-(4-(3-fluorophenyl)-1H-1,2,3-triazol-1-yl)-N-((1R,2S,3S)-3-(3-(3-fluorophenyl)-1H-1,2,4-triazol-1-yl)-2-hydroxycyclohexyl)-7-methoxy-2-phenylhexahydropyrano[3,2-d][1,3]dioxine-6-carboxamide: Prepared in a similar fashion as described in Example 1a, Step-6 using (1S,2R,6S)-2-amino-6-(3-(3-fluorophenyl)-1H-1,2,4-triazol-1-yl)cyclohexanol (33.4 mg, 0.121 mmol) and (4aR,6R,7R,8R,8aR)-8-(4-(3-fluorophenyl)-1H-1,2,3-triazol-1-yl)-7-methoxy-2-phenylhexahydropyrano[3,2-d][1,3]dioxine-6-carboxylic acid (0.05 g, 0.110 mmol). The crude was purified by flash chromatography (60-120 silicagel, 6-10% MeOH in $CHCl_3$) to afford (4aR,6R,7R,8R,8aR)-8-(4-(3-fluorophenyl)-1H-1,2,3-triazol-1-yl)-N-((1R,2S,3S)-3-(3-(3-fluorophenyl)-1H-1,2,4-triazol-1-yl)-2-hydroxycyclohexyl)-7-methoxy-2-phenylhexahydropyrano[3,2-d][1,3]dioxine-6-carboxamide (Isomer 1) (0.020 g, 24% yield) and (4aR,6R,7R,8R,8aR)-8-(4-(3-fluorophenyl)-1H-1,2,3-triazol-1-yl)-N-((1R,2S,3S)-3-(3-(3-fluorophenyl)-1H-1,2,4-triazol-1-yl)-2-hydroxycyclohexyl)-7-methoxy-2-phenylhexahydropyrano[3,2-d][1,3]dioxine-6-carboxamide (Isomer 2) (0.024 g, 22% yield). LC-MS, $[M+H]^+$=714.2 {Method F, $t_R$:2.375-Isomer-1/2.350 for Isomer-2}.

Step-5: To a stirred solution of (4aR,6R,7R,8R,8aR)-8-(4-(3-fluorophenyl)-1H-1,2,3-triazol-1-yl)-N-((1R,2S,3S)-3-(3-(3-fluorophenyl)-1H-1,2,4-triazol-1-yl)-2-hydroxycyclohexyl)-7-methoxy-2-phenylhexahydropyrano[3,2-d][1,3]dioxine-6-carboxamide (Isomer 1) (20 mg, 0.028 mmol) in dichloromethane (1 mL) was added trifluoroacetic acid (0.15 mL, 1.947 mmol) and stirred the reaction mixture at rt for 2 h. Then the solvent was removed under reduced pressure and crude was purified through Prep HPLC {Method A}. Desired fractions were concentrated under reduced pressure to afford Example 9a: (2R,3R,4S,5R,6R)-4-(4-(3-fluorophenyl)-1H-1,2,3-triazol-1-yl)-N-((1S,2R,3R)-3-(3-(3-fluorophenyl)-1H-1,2,4-triazol-1-yl)-2-hydroxycyclohexyl)-5-hydroxy-6-(hydroxymethyl)-3-methoxytetrahydro-2H-pyran-2-carboxamide (Isomer 1) (4.8 mg, 27.4% yield) as an off-white solid. LC-MS, $[M+H]^+$=626.1, [$t_R$=1.682 min, Method A] and & [$t_R$=1.691 min, Method B]. $^1$H NMR (400 MHz, MEOH-$d_4$) δ ppm 8.61 (s, 1H), 8.50 (s, 1H), 7.88 (d, J=7.8 Hz, 1H), 7.76 (d, J=10.3 Hz, 1H), 7.67 (d, J=7.8 Hz, 1H), 7.62 (d, J=10.0 Hz, 1H), 7.53-7.42 (m, 2H), 7.17 (td, J=8.4, 2.3 Hz, 1H), 7.13-7.06 (m, 1H), 4.92 (dd, J=10.8, 2.9 Hz, 1H), 4.36-4.22 (m, 2H), 4.12 (d, J=2.9 Hz, 1H), 4.02-3.88 (m, 3H), 3.85-3.78 (m, 2H), 3.76-3.70 (m, 1H), 3.18 (s, 3H), 2.22-2.12 (m, 2H), 2.08-2.02 (m, 1H), 1.98-1.92 (m, 1H), 1.68-1.52 (m, 2H). hGal3 $IC_{50=0.5}$ µM.

EXAMPLE 9b

Prepared in a similar fashion as described in Example 9a using (4aR,6R,7R,8R,8aR)-8-(4-(3-fluorophenyl)-1H-1,2,3-triazol-1-yl)-N-((1R,2S,3S)-3-(3-(3-fluorophenyl)-1H-1,2,4-triazol-1-yl)-2-hydroxycyclohexyl)-7-methoxy-2-phenylhexahydropyrano[3,2-d][1,3]dioxine-6-carboxamide (Isomer 2) in step 5 (0.024 g, 0.034 mmol). The crude was purified through Prep HPLC {Method A}. Desired fractions were concentrated under reduced pressure to afford (2R,3R,4S,5R,6R)-4-(4-(3-fluorophenyl)-1H-1,2,3-triazol-1-yl)-N-((1S,2R,3R)-3-(3-(3-fluorophenyl)-1H-1,2,4-triazol-1-yl)-2-hydroxycyclohexyl)-5-hydroxy-6-(hydroxymethyl)-3- methoxytetrahydro-2H-pyran-2-carboxamide (Isomer 2) (1.01 mg, 4.5% yield) as an off-white solid. LC-MS, [M+H]⁺=626.1, [$t_R$=1.661 min, Method A] and & [$t_R$=1.668 min, Method B]. ¹H NMR (400 MHz, MEOH-$d_4$) δ ppm 8.63 (s, 1H), 8.49 (s, 1H), 7.87 (d, J=7.6 Hz, 1H), 7.75 (d, J=10.3 Hz, 1H), 7.70 (d, J=7.3 Hz, 1H), 7.63 (d, J=11.0 Hz, 1H), 7.51-7.44 (m, 2H), 7.20-7.07 (m, 2H), 4.94-4.90 (m, 1H), 4.35-4.24 (m, 2H), 4.12 (d, J=3.4 Hz, 1H), 3.97-3.86 (m, 3H), 3.84-3.79 (m, 2H), 3.76-3.70 (m, 1H), 3.20 (s, 3H), 2.22-2.06 (m, 4H), 1.94 (br. s., 1H), 1.65-1.57 (m, 1H). hGal3 IC$_{50}$=>100 μM.

Cyclohexyl_N_Methyl_Analogs:

separated and aqueous layer re-extracted with DCM (2×20 mL). The combined organic extracts were washed with water, brine, dried over sodium sulphate and concentrated to give crude residue. The crude residue was purified by flash chromatography (40-50% EtOAc in n-hexane) to afford 1-((1S,2R,6R)-7-oxabicyclo[4.1.0]heptan-2-yl)-4-(3-fluorophenyl)-1H-1,2,3-triazole (0.53 g, 57%) as pale yellow solid. LC/MS [M+H]⁺=260.2, $t_R$=2.266 min (Method C).

Step-2: Synthesis of (1R,2R,6S)-2-(4-(3-fluorophenyl)-1H-1,2,3-triazol-1-yl)-6-(methylamino)cyclohexanol (racemate): In sealed tube 1-((1S,2R,6R)-7-oxabicyclo[4.1.0]heptan-2-yl)-4-(3-fluorophenyl)-1H-1,2,3-triazole (110 mg,

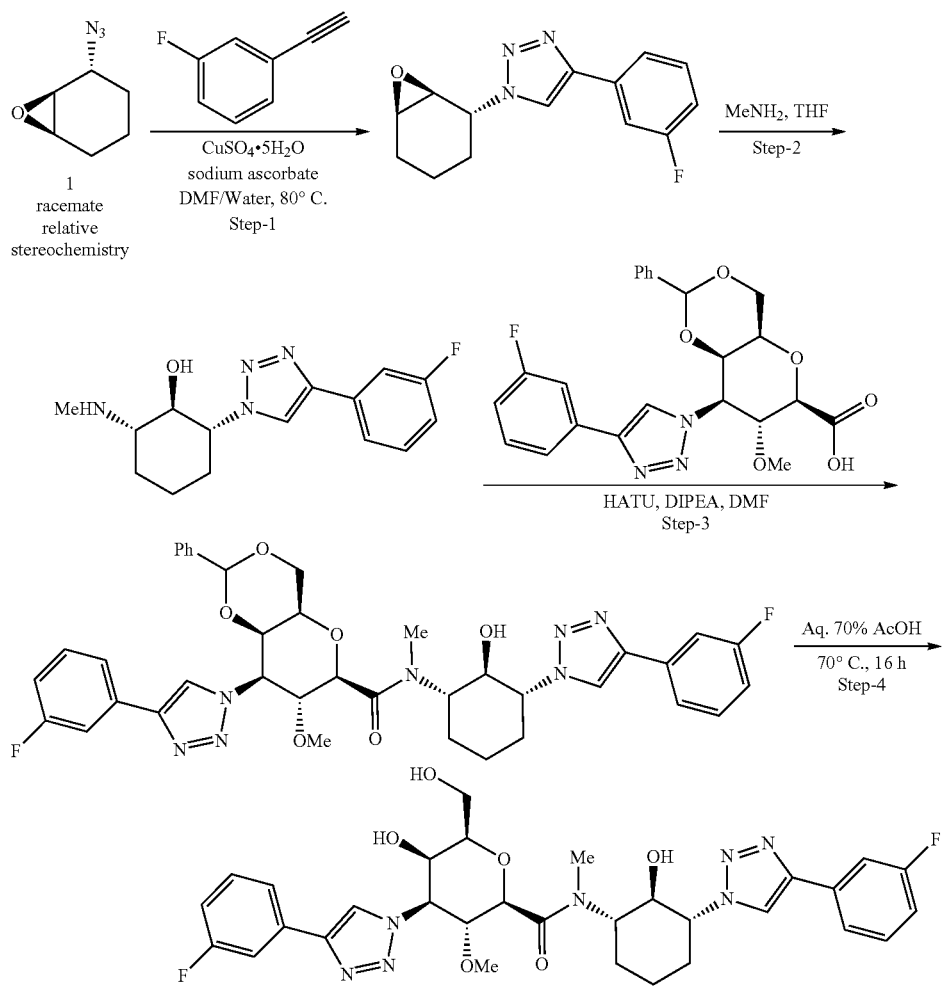

Example 10a & 10b

Step-1: Synthesis of 1-((1S,2R,6R)-7-oxabicyclo[4.1.0]heptan-2-yl)-4-(3-fluorophenyl)-1H-1,2,3-triazole (racemate): To a solution of (1S,2R,6R)-2-azido-7-oxabicyclo[4.1.0]heptane (0.5 g, 3.59 mmol) in DMF (5 mL) and water (1.5 mL) was added sodium ascorbate (0.71 g, 3.59 mmol), copper(II) sulfate pentahydrate (0.81 g, 3.23 mmol) and 3-fluorophenylacetylene (1.7 mL, 14.37 mmol) at rt. The reaction mixture was heated at 85° C. for 30 min. The reaction mixture was cooled to rt, diluted with 1:1 DCM (50 mL) and water (50 mL) and stirred at rt for 15 min. The reaction mixture was filtered through Celite pad and washed with DCM (20 mL). From the filtrate, organic layer was 0.424 mmol) and methanamine (33% solution in ethanol) (5 mL, 0.424 mmol) was heated to 65° C. for 16 h. The reaction mixture was cooled to rt and solvent was removed under reduced pressure to give crude residue. The crude residue was triturated with n-pentane and dried to afford (1R,2R,6S)-2-(4-(3-fluorophenyl)-1H-1,2,3-triazol-1-yl)-6-(methylamino)cyclohexanol (109 mg, 88%). LC/MS [M+H]⁺=291.0, $t_R$=1.372 min (Method F).

Step-3: Synthesis of (4aR,6R,7R,8R,8aR)-8-(4-(3-fluorophenyl)-1H-1,2,3-triazol-1-yl)-N-((1S,2R,3R)-3-(4-(3-fluorophenyl)-1H-1,2,3-triazol-1-yl)-2-hydroxycyclohexyl)-7-methoxy-N-methyl-2-phenylhexahydropyrano[3,2-d][1,3]

dioxine-6-carboxamide: To a solution of ((2S,4aR,6R,7R,8R,8aR)-8-(4-(3-fluorophenyl)-1H-1,2,3-triazol-1-yl)-7-methoxy-2-phenylhexahydropyrano[3,2-d][1,3]dioxine-6-carboxylic acid (50 mg, 0.11 mmol) in DMF (2 mL) was added DIPEA (0.06 mL, 0.33 mmol) and HATU (63 mg, 0.16 mmol) at rt and stirred for 15 min. Then (1R,2R,6S)-2-(4-(3-fluorophenyl)-1H-1,2,3-triazol-1-yl)-6-(methylamino)cyclohexanol (35.1 mg, 0.121 mmol) was added and stirred the mixture at rt for 1 h. The reaction mixture was quenched with ice cold water (10 mL) and stirred for 15 min. The resultant solid was filtered, washed with excess water and residue was dried to afford diastereomeric mixture of crude residue. The crude residue was further purified by prep-SFC to obtain Isomer 1 and Isomer 2.
Preparative SFC Conditions
  Column/dimensions: Chiralcel OD-H(250×21)mm, 5 u
  % CO2: 60%
  % Co solvent: 40% of 0.2% DEA in MEOH
  Total Flow: 80.0 g/min
  Back Pressure: 100 bar
  Temperature: 25° C.
  UV: 242 nm
  Isomer 1: 35 mg, 37% yield; LC/MS [M+H]$^+$=728.2, $t_R$=3.178 min (Method C).
  Isomer 2: 25 mg, 31% yield; LC/MS [M+H]$^+$=728.0, $t_R$=2.635 min (Method F).

EXAMPLE 10a (2S,4aR,6R,7R,8R,8aR)-8-(4-(3-fluorophenyl)-1H-1,2,3-triazol-1-yl)-N-((1S,2R,3R)-3-(4-(3-fluorophenyl)-1H-1,2,3-triazol-1-yl)-2-hydroxycyclohexyl)-7-methoxy-N-methyl-2-phenylhexahydropyrano[3,2-d][1,3]dioxine-6-carboxamide (Isomer 1) (35 mg, 0.048 mmol) was suspended in aq. 70% acetic acid (5 mL) and heated at 70° C. for 16 h. The reaction mixture was cooled to rt and concentrated under reduced pressure to give crude residue. The crude residue was purified by prep-HPLC [Method A] to afford ((2R,3R,4S,5R,6R)-4-(4-(3-fluorophenyl)-1H-1,2,3-triazol-1-yl)-N-((1S,2R,3R)-3-(4-(3-fluorophenyl)-1H-1,2,3-triazol-1-yl)-2-hydroxycyclohexyl)-5-hydroxy-6-(hydroxymethyl)-3-methoxy-N-methyltetrahydro-2H-pyran-2-carboxamide Isomer 1(9.3 mg, 30%) as an off-white solid. LC/MS [M+H]$^+$=640.2, $t_R$=1.788 min (Method A); $^1$H NMR (400 MHz, MEOH-d4) δ ppm 8.71, 8.70 (two singlets, 1H), 8.53, 8.42 (two singlets, 1H), 7.76-7.57 (m, 4H), 7.53-7.42 (m, 2H), 7.15-7.05 (m, 2H), 5.03-4.96 (m, 1H), 4.76-4.66 (m, 1H), 4.58 (m, 1H), 4.55-4.35 (m, 3H), 4.34-4.04 (m, 4H), 3.21, 3.00 (two singlets, 3H), 3.13, 3.11 (two singlets, 3H), 2.27-2.09 (m, 2H), 2.04-1.90 (m, 2H), 1.85 (m, 2H) {Rotameric mixture}. hGal3 IC$_{50}$=5.5 µM.

EXAMPLE 10b ((2S,4aR,6R,7R,8R,8aR)-8-(4-(3-fluorophenyl)-1H-1,2,3-triazol-1-yl)-N-((1S,2R,3R)-3-(4-(3-fluorophenyl)-1H-1,2,3-triazol-1-yl)-2-hydroxycyclohexyl)-7-methoxy-N-methyl-2-phenylhexahydropyrano[3,2-d][1,3]dioxine-6-carboxamide (Isomer 2) (25 mg, 0.034 mmol) was suspended in 70% Aq. acetic acid (5 mL, 87 mmol) and heated at 70° C. for 16 h. The reaction mixture was cooled to rt and concentrated under reduced pressure to give crude residue. The crude residue was purified by prep-HPLC [Method A] to afford ((2R,3R,4S,5R,6R)-4-(4-(3-fluorophenyl)-1H-1,2,3-triazol-1-yl)-N-((1S,2R,3R)-3-(4-(3-fluorophenyl)-1H-1,2,3-triazol-1-yl)-2-hydroxycyclohexyl)-5-hydroxy-6-(hydroxymethyl)-3-methoxy-N-methyltetrahydro-2H-pyran-2-carboxamide Isomer 2 (2.2 mg, 10%). LC/MS [M+H]$^+$=640.2, $t_R$=1.78 min (Method A); $^1$H NMR (400 MHz, MEOH-d4) δ ppm 8.72, 8.71 (two singlets, 1H), 8.47, 8.45 (two singlets, 1H), 7.75-7.57 (m, 4H), 7.53-7.43 (m, 2H), 7.10 (t, J=8.4 Hz, 2H), 5.03-4.95 (m, 1H), 4.65-4.49 (m, 3H), 4.47-4.40 (m, 1H), 4.21-4.00 (m, 2H), 3.94-3.84 (m, 1H), 3.83-3.64 (m, 2H), 3.21, 2.98 (two singlets, 3H), 3.14, 3.11(two singlets, 3H), 2.28-2.11 (m, 2H), 2.10-1.95 (m, 2H), 1.94-1.64 (m, 2H). [Rotameric mixture]; hGal$_3$ IC$_{50}$=0.091 µM.

The Examples in the table 2 were prepared in an analogous fashion to Example 10a and 10b, substituting methyl amine with the appropriate alkyl amines in the synthetic sequence.

TABLE 2

| EX # | Structure (Synthetic Method A) | LCMS/$t_R$ (min); $^1$H NMR (400 MHz, methanol-d$_4$) | hGal-3 IC$_{50}$ (µM) |
|---|---|---|---|
| 11a | | (M + H)$^+$ = 670.1/1.699; δ ppm 8.70, 8.69 (two singlets, 1H), 8.44, 8.42 (two singlets, 1H), 7.72-7.55 (m, 4H), 7.50-7.40 (m, 2H), 7.12-7.05 (m, 2H), 4.99-4.92 (m, 1H), 4.57-4.47 (m, 5H), 4.13-4.00 (m, 2H), 3.93-3.79 (m, 2H), 3.78-3.63 (m, 3H), 3.59-3.47 (m, 1H), 3.11, 3.09 (two singlets, 3H), 2.16-2.32 (m, 2H), 2.08-1.90 (m, 2H), 1.88-1.66 (m, 2H). | 0.36 |
| 11b | | (M + H)$^+$ = 670.1/1.741; δ ppm 8.70, 8.76 (two singlets, 1H), 8.43, 8.42 (two singlets, 1H), 7.74-7.56 (m, 4H), 7.46 (m, 2H), 7.09 (t, J = 8.0 Hz, 2H), 4.96 (dd, J = 10.5, 2.5 Hz, 1H), 4.80-4.63 (m, 1H), 4.59-4.43 (m, 1H), 4.37 (d, J = 9.5 Hz, 1H), 4.17-4.06 (m, 2H), 3.96-3.79 (m, 4H), 3.77-3.45 (m, 4H), 3.11, 3.10 (two singlets, 3H), 2.26-2.09 (m, 2H), 1.99-1.72 (m, 4H). | 18.0 |

TABLE 2-continued

| EX # | Structure (Synthetic Method A) | LCMS/$t_R$ (min); $^1$H NMR (400 MHz, methanol-$d_4$) | hGal-3 IC$_{50}$ (µM) |
|---|---|---|---|
| 12a | | (M + H)$^+$ = 666.6/1.66; δ ppm 8.68 (s, 1H), 8.43 (s, 1H), 7.72-7.55 (m, 4H), 7.50-7.40 (m, 2H), 7.13-7.03 (m, 2H), 4.99 (dd, J = 10.8, 2.9 Hz, 2H), 4.61-4.35 (m, 3H), 4.08 (d, J = 2.9 Hz, 1H), 3.87-3.63 (m, 3H), 3.15-3.06 (m, 4H), 2.16-2.14 (m, 3H), 2.03-1.78 (m, 2H), 1.60-1.58 (m, 1H), 1.3-1.28 (m, 1H), 1.18-0.81 (m, 3H), (1H might be obscured with solvent peak). | 0.17 |
| 12b | | (M + H)$^+$ = 666.6/2.27; δ ppm 8.60-8.78 (m, 1 H), 8.34-8.48 (m, 1 H), 7.52-7.76 (m, 4 H), 7.38-7.52 (m, 2 H), 6.99-7.18 (m, 2 H), 4.91-5.01 (m, 2 H), 4.37-4.59 (m, 3 H), 4.05-4.15 (m, 1 H), 3.64-3.93 (m, 3 H), 3.13 (s, 3 H), 3.01 (br s, 1 H), 1.99-2.37 (m, 3 H), 1.80-1.99 (m, 2 H), 1.50-1.67 (m, 1 H), 0.86-1.35 (m, 4 H), (1H might be obscured with solvent/moisture peak). | 4.02 |
| 13a | | (M + H)$^+$ = 654.2/1.9; δ ppm 8.73-8.64 (m, 1H), 8.46-8.39 (m, 1H), 7.75-7.54 (m, 4H), 7.50-7.40 (m, 2H), 7.1-7.09 (m, 2H), 5.02-4.93 (m, 1H), 4.78-4.57 (m, 1H), 4.50-4.36 (m, 3H), 4.15-4.05 (m, 2H), 3.94-3.35 (m, 5H), 3.15-3.09 (m, 3H), 2.24-2.09 (m, 2H), 2.05-1.58 (m, 4H), 1.40-1.18 (m, 3H). | 1.56 |
| 13b | | (M + H)$^+$ = 654.1/1.87; δ ppm 8.71-8.66 (m, 1H), 8.47-8.42 (m, 1H), 7.73-7.56 (m, 4H), 7.51-7.41 (m, 2H), 7.13-7.04 (m, 2H), 5.02-4.94 (m, 1H), 4.62-4.32 (m, 3H), 4.13-4.00 (m, 3H), 3.92-3.47 (m, 5H), 3.15-3.08 (m, 3H), 2.26-2.06 (m, 3H), 2.05-1.61 (m, 3H), 1.42-1.19 (m, 3H). | 0.14 |
| 14a | | (M + H)$^+$ = 668.2/2.03; δ ppm 8.72-8.68 (m, 1H), 8.46-8.41 (m, 1H), 7.74-7.56 (m, 4H), 7.51-7.42 (m, 2H), 7.13-7.04 (m, 2H), 5.13-4.91 (m, 1H), 4.68-4.36 (m, 3H), 4.30-4.08 (m, 2H), 3.93-3.65 (m, 4H), 3.16-3.12 (m, 3H), 2.24-1.66 (m, 6H), 1.52-1.25 (m, 6H), (1H might be obscured with solvent/moisture peak). | 12.0 |
| 14b | | (M + H)$^+$ = 668.5/1.95; δ ppm 8.68 (d, J = 3.4 Hz, 1H), 8.49-8.38 (m, 1H), 7.74-7.54 (m, 4H), 7.53-7.38 (m, 2H), 7.13-7.00 (m, 2H), 5.05-4.92 (m, 1H), 4.55-4.38 (m, 3H), 4.30-3.95 (m, 2H), 3.92-3.59 (m, 4H), 3.15-3.09 (m, 3H), 2.24-1.70 (m, 6H), 1.53-1.26 (m, 6H), (1H might be obscured with solvent/moisture peak). | 1.38 |

TABLE 2-continued

| EX # | Structure (Synthetic Method A) | LCMS/$t_R$ (min); $^1$H NMR (400 MHz, methanol-$d_4$) | hGal-3 IC$_{50}$ (μM) |
|---|---|---|---|
| 15a | | (M + H)$^+$ = 690.1/2.00; δ ppm 8.73-8.66 (m, 1H), 8.45-8.41 (m, 1H), 7.75-7.56 (m, 4H), 7.52-7.41 (m, 2H), 7.1-7.09 (m, 2H), 6.35-6.00 (m, 1H), 4.98 (dd, J = 10.5, 2.9 Hz, 1H), 4.79-4.61 (m, 2H), 4.56-4.43 (m, 3H), 4.15-3.99 (m, 2H), 3.95-3.55 (m, 4H), 3.15-3.08 (m, 3H), 2.26-2.08 (m, 2H), 2.05-1.66 (m, 4H). | 8.78 |
| 15b | | (M + H)$^+$ = 690.1/1.95; δ ppm 8.72-8.68 (m, 1H), 8.46-8.41 (m, 1H), 7.73-7.55 (m, 4H), 7.51-7.41 (m, 2H), 7.1-7.08 (m, 2H), 6.35-5.98 (m, 1H), 4.97 (dd, J = 10.1, 2.8 Hz, 1H), 4.63-4.43 (m, 3H), 4.15-4.05 (m, 2H), 4.04-3.95 (m, 1H), 3.94-3.52 (m, 5H), 3.10 (s, 3H), 2.18-2.16 (m, 2H), 2.12-1.61 (m, 4H). | 0.04 |

EXAMPLE 16a AND 16b

Synthesis of (2R,3R,4S,5R,6R)-4-(4-(3-fluorophenyl)-1H-1,2,3-triazol-1-yl)-N-((3R,4S,5S)-5-(4-(3-fluorophenyl)-1H-1,2,3-triazol-1-yl)-4-hydroxypiperidin-3-yl)-5-hydroxy-6-(hydroxymethyl)-3-methoxy-N-methyltetrahydro-2H-pyran-2-carboxamide (Isomer 1 and 2)

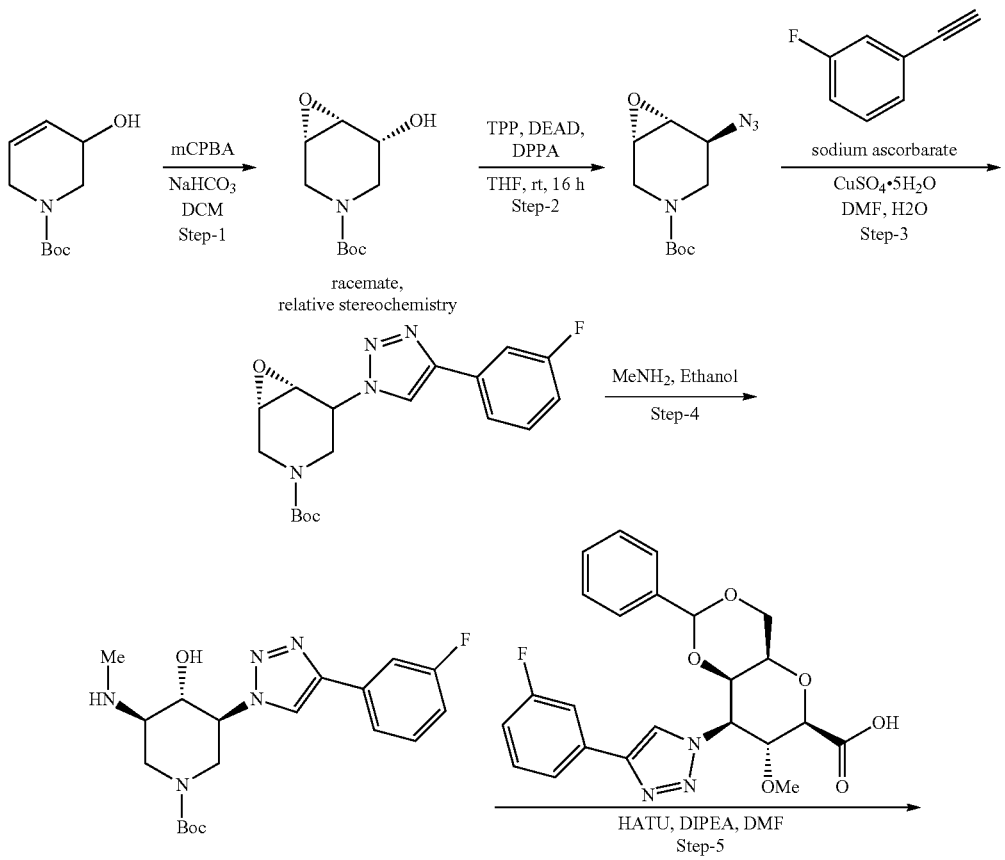

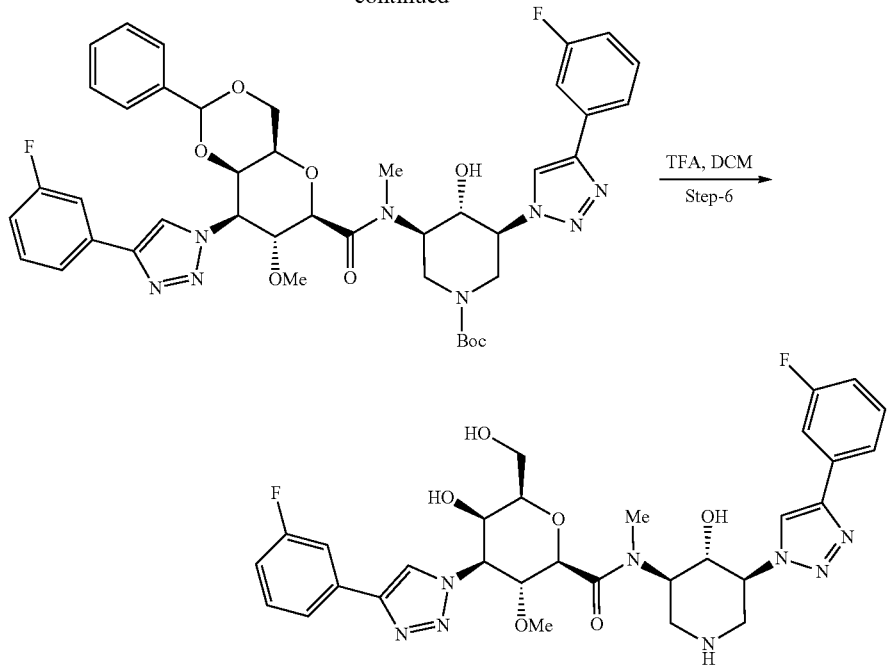

Example 16a & 16b

Step-1: Synthesis of tert-butyl (1S,5R,6R)-5-hydroxy-7-oxa-3-azabicyclo[4.1.0]heptane-3-carboxylate (racemate): To a solution of N-Boc-3-hydroxy-1,2,3,6-tetrahydropyridine (500 mg, 2.51 mmol) in DCM (25 mL) was added sodium bicarbonate (211 mg, 2.51 mmol) followed by mCPBA (928 mg, 3.76 mmol) in DCM (3 mL) at 0° C. under $N_2$. The reaction mixture was allowed to warm to rt and was stirred for 24 h. The reaction mixture was diluted with DCM (100 mL), filtered through a Celite pad and the filtrate was washed with saturated $Na_2SO_3$ (2×50 mL), saturated $NaHCO_3$ (2×50 mL) and saturated NaCl (25 mL). The organic layer was dried over $Na_2SO_4$, filtered, and concentrated and the crude residue was purified by silica gel chromatography (40%→50% ethyl acetate in hexanes) to yield the title compound (430 mg, 80% yield) as a white solid. 1H NMR (400 MHz, CHLOROFORM-d) δ 4.01 (br. s, 1H), 3.92-3.44 (m, 5H), 3.10 (dd, J=12.8, 7.2 Hz, 1H), 1.29 (s, 9H) (Rotameric mixture).

Step-2: Synthesis of tert-butyl (1S,5S,6R)-5-azido-7-oxa-3-azabicyclo[4.1.0] heptane-3-carboxylate (racemate): To a stirred solution of (1S,5R,6R)-tert-butyl 5-hydroxy-7-oxa-3-azabicyclo[4.1.0]heptane-3-carboxylate (325 mg, 1.510 mmol) in THF (50 mL) was added triphenylphosphine (792 mg, 3.02 mmol). The reaction mixture was cooled 0° C. DEAD (0.478 mL, 3.02 mmol) and DPPA (0.651 mL, 3.02 mmol) were added sequentially under $N_2$. The reaction mixture was allowed to warm to rt and was stirred for 16 h. The solvent was removed under reduced pressure and the crude residue was purified by silica gel chromatography (10%→15% ethyl acetate in hexanes) to yield the title compound (230 mg, 64% yield) as pale a yellow oil. 1H NMR (400 MHz, DMSO-d6) δ 4.09-3.82 (m, 2H), 3.62-3.38 (m, 4H), 3.17 (dd, J=13.1, 3.3 Hz, 1H), 1.40 (s, 9H) (Rotameric mixture).

Step-3: Synthesis of tert-butyl (1S,5S,6R)-5-(4-(3-fluorophenyl)-1H-1,2,3-triazol-1-yl)-7-oxa-3-azabicyclo[4.1.0] heptane-3-carboxylate (racemate): To a solution of (1R,5R,6S)-tert-butyl 5-azido-7-oxa-3-azabicyclo[4.1.0]heptane-3-carboxylate (1.6 g, 6.66 mmol) in DMF (30 mL) and water (7.50 mL), was added sodium ascorbate (1.319 g, 6.66 mmol), copper(II) sulfate pentahydrate (1.496 g, 5.99 mmol) and 3-fluorophenylacetylene (3.08 mL, 26.6 mmol) sequentially at rt. The reaction mixture was degassed with $N_2$ for 5 min and heated to 85° C. for 30 min. The mixture was cooled to rt, diluted with ice cold water (100 mL) and stirred for 15 min to get a solid. The solid was filtered, suspended in DCM (100 mL), filtered through celite pad and washed with excess DCM. The filtrate was dried over sodium sulfate and concentrated. The residue was purified by silica gel (40%→80% ethyl acetate in hexanes) to afford the title compound (1.1 g, 46% yield) as a white solid. $^1$H NMR (400 MHz, CHLOROFORM-d) δ 7.83 (br. s, 1H), 7.59-7.55 (m, 2H), 7.42-7.38 (m, 1H), 7.10-7.07 (m, 1H), 5.18-5.06 (m, 1H), 4.34-4.29 (m, 1H), 3.93-3.45 (m, 5H), 1.47-1.11 (m, 9H) (rotameric mixture); LC/MS, [M+H]$^+$=361.0, $t_R$=2.01 min (Method E).

Step-4: Synthesis of (3S,4S,5R)-tert-butyl 3-(4-(3-fluorophenyl)-1H-1,2,3-triazol-1-yl)-4-hydroxy-5-(methylamino) piperidine-1-carboxylate (racemate): (1S,5S,6R)-tert-butyl5-(4-(3-fluorophenyl)-1H-1,2,3-triazol-1-yl)-7-oxa-3-azabicyclo[4.1.0]heptane-3-carboxylate (100 mg, 0.277 mmol) in methanamine (33% solution in Ethanol) (5 mL, 0.277 mmol) was heated in a sealed tube at 65° C. for 16 h. Reaction mixture was cooled to rt and solvent was removed under reduced pressure to give crude residue. The crude residue was triturated with pentane and dried under reduced pressure to give (3S,4S,5R)-tert-butyl 3-(4-(3-fluorophenyl)-1H-1,2,3-triazol-1-yl)-4-hydroxy-5-(methylamino)piperidine-1-carboxylate (105 mg, 94%). LC-MS, [M+H]$^+$=392.2, {Method C: $t_R$=1.855 min}.

Step-5: To a stirred solution of (4aR,6R,7R,8R,8aR)-8-(4-(3-fluorophenyl)-1H-1,2,3-triazol-1-yl)-7-methoxy-2-phenylhexahydropyrano[3,2-d][1,3]dioxine-6-carboxylic acid (50 mg, 0.110 mmol) in DMF (2 mL), DIPEA (0.058 mL, 0.329 mmol) and HATU (62.6 mg, 0.165 mmol) were added sequentially at rt and stirred for 15 min. Then (3S,4S,5R)-tert-butyl 3-(4-(3-fluorophenyl)-1H-1,2,3-triazol-1-yl)-4-hydroxy-5-(methylamino)piperidine-1-carboxylate (47.3 mg, 0.121 mmol) was added and stirred the reaction mixture at rt for 1 h. The reaction mixture was quenched with ice water and stirred for 15 minutes. The resultant solid was filtered and dried to afford crude residue. The crude residue was purified by silica gel (5-10% MeOH in chloroform) to afford tert-butyl (3S,4S,5R)-3-(4-(3-fluorophenyl)-1H-1,2,3-triazol-1-yl)-5-((4aR,6R,7R,8R,8aR)-8-(4-(3-fluorophenyl)-1H-1,2,3-triazol-1-yl)-7-methoxy-N-methyl-2-phenylhexahydropyrano[3,2-d][1,3]dioxine-6-carboxamido)-4-hydroxypiperidine-1-carboxylate as the diastereomeric mixture which was further purified by chiral SFC to afford the two isomers:

Prep SFC Method Info:
  Column/dimensions: Chiralcel OJ-H(250×21)mm, 5 u
  % CO2: 70%
  % Co solvent: 30% of IPA+ACN
  Total Flow: 70.0 g/min
  Back Pressure: 100 bar
  Temperature: 25° C.
  UV: 244 nm Analytical Chiral SFC Conditions:
  Analytical Column: ChiralCel OJH (250×4.6)mm, 5 u
  BPR pressure: 100 bars
  Temperature: 22.3° C.
  Flow rate: 2.8 g/min
  Mobile Phase: $CO_2$/IPA+ACN (70/30)
  Detector Wavelength: UV 200-400 nm
  Isomer 1: (30 mg, 31% yield); chiral SFC $t_R$=1.8 min; LC-MS, [M+H]$^+$=829.0, {Method F: $t_R$=2.855 min};
  Isomer 2: (28 mg, 31% yield); chiral SFC $t_R$=5.15 min; LC-MS, [M+H]$^+$=829.0, {Method F: $t_R$=3.0 min};

Step-6: To a solution of (3S,4S,5R)-tert-butyl 3-(4-(3-fluorophenyl)-1H-1,2,3-triazol-1-yl)-5-((4aR,6R,7R,8R,8aR)-8-(4-(3-fluorophenyl)-1H-1,2,3-triazol-1-yl)-7-methoxy-N-methyl-2-phenylhexahydropyrano[3,2-d][1,3]dioxine-6-carboxamido)-4-hydroxypiperidine-1-carboxylate Isomer 1 (30 mg, 0.036 mmol) in dichloromethane (1 mL), trifluoroacetic acid (0.15 mL, 1.947 mmol) was added and stirred the mixture at rt for 2 h. Then, the solvent was removed under reduced pressure to get crude residue. The crude material was purified via preparative HPLC Method A to afford Example 16a: (2R,3R,4S,5R,6R)-4-(4-(3-fluorophenyl)-1H-1,2,3-triazol-1-yl)-N-((3R,4S,5S)-5-(4-(3-fluorophenyl)-1H-1,2,3-triazol-1-yl)-4-hydroxypiperidin-3-yl)-5-hydroxy-6-(hydroxymethyl)-3-methoxy-N-methyltetrahydro-2H-pyran-2-carboxamide Isomer 1 (10.6 mg, 47% yield) as an off-white solid. LC-MS, [M+H]$^+$=641.3, {Method A: $t_R$=1.520}. 1H NMR (400 MHz, MEOH-d4) δ ppm 8.72, 8.68 (two singlets, 1H), 8.45 (m, 1H), 7.74-7.55 (m, 4H), 7.51-7.41 (m, 2H), 7.14-7.04 (m, 2H), 4.97 (dd, J=10.6, 2.8 Hz, 1H), 4.67-4.49 (m, 2H), 4.48-4.24 (m, 3H), 4.10 (dd, J=7.9, 2.6 Hz, 1H), 3.95 (dd, J=8.4, 3.8 Hz, 1H), 3.89-3.76 (m, 2H), 3.74-3.68 (m, 1H), 3.43-3.35 (m, 1H), 3.23, 3.00 (two singlets, 3H), 3.22-3.16 (m, 1H), 3.14-3.10 (m, 3H), 3.09-3.01 (m, 1H) [*rotameric mixture]; hGal3 IC$_{50}$=3.5 µM.

EXAMPLE 16b

To a solution of (3S,4S,5R)-tert-butyl 3-(4-(3-fluorophenyl)-1H-1,2,3-triazol-1-yl)-5-((4aR,6R,7R,8R,8aR)-8-(4-(3-fluorophenyl)-1H-1,2,3-triazol-1-yl)-7-methoxy-N-methyl-2-phenylhexahydropyrano[3,2-d][1,3]dioxine-6-carboxamido)-4-hydroxypiperidine-1-carboxylate Isomer 2 (28 mg, 0.034 mmol) in dichloromethane (1 mL), trifluoroacetic acid (0.15 mL, 1.947 mmol) was added at rt and stirred for 2 h. Then, the solvent was removed under reduced pressure to get crude residue. The crude material was purified via preparative LC/MS Method A to afford (2R,3R,4S,5R,6R)-4-(4-(3-fluorophenyl)-1H-1,2,3-triazol-1-yl)-N-((3R,4S,5S)-5-(4-(3-fluorophenyl)-1H-1,2,3-triazol-1-yl)-4-hydroxypiperidin-3-yl)-5-hydroxy-6-(hydroxymethyl)-3-methoxy-N-methyltetrahydro-2H-pyran-2-carboxamide Isomer 2 (12.4 mg, 0.019 mmol, 57%) as an off-white solid. LC-MS, [M+H]$^+$=641.1, {Method A: $t_R$=1.517}. 1H NMR (400 MHz, MEOH-d4) δ ppm 8.71, 8.68 (two singlets, 1H), 8.53, 8.51 (two singlets, 1H), 7.73-7.57 (m, 4H), 7.51-7.42 (m, 2H), 7.14-7.05 (m, 2H), 4.97 (dt, J=10.3, 3.4 Hz, 1H), 4.57-4.37 (m, 2H), 4.30-4.21 (m, 1H), 4.08 (dd, J=7.5, 2.3 Hz, 1H), 4.01-3.96 (m, 1H), 3.90-3.67 (m, 5H), 3.50-3.41 (m, 2H), 3.27, 3.00 (two singlets, 3H), 3.13-3.10 (m, 3H), 3.04 (m, 1H) {Rotameric Mixture}. hGal3 IC$_{50}$=0.044 µM.

EXAMPLE 17a AND 17b

Synthesis of (2R,4R,5R,6R)-4-(4-(3-fluorophenyl)-1H-1,2,3-triazol-1-yl)-N-((3R,4S,5S)-5-(4-(3-fluorophenyl)-1H-1,2,3-triazol-1-yl)-4-hydroxypiperidin-3-yl)-5-hydroxy-6-(hydroxymethyl)-N-methyltetrahydro-2H-pyran-2-carboxamide (Isomer 1 and 2)

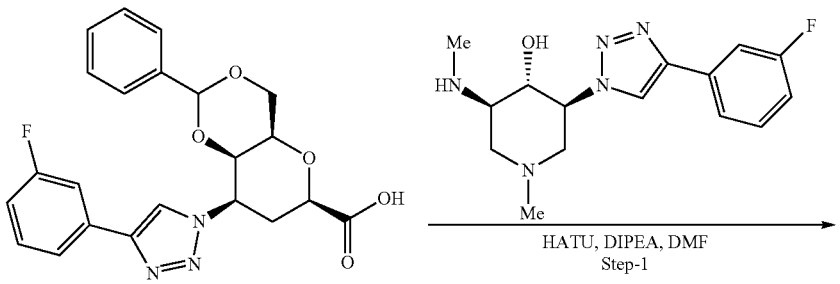

-continued

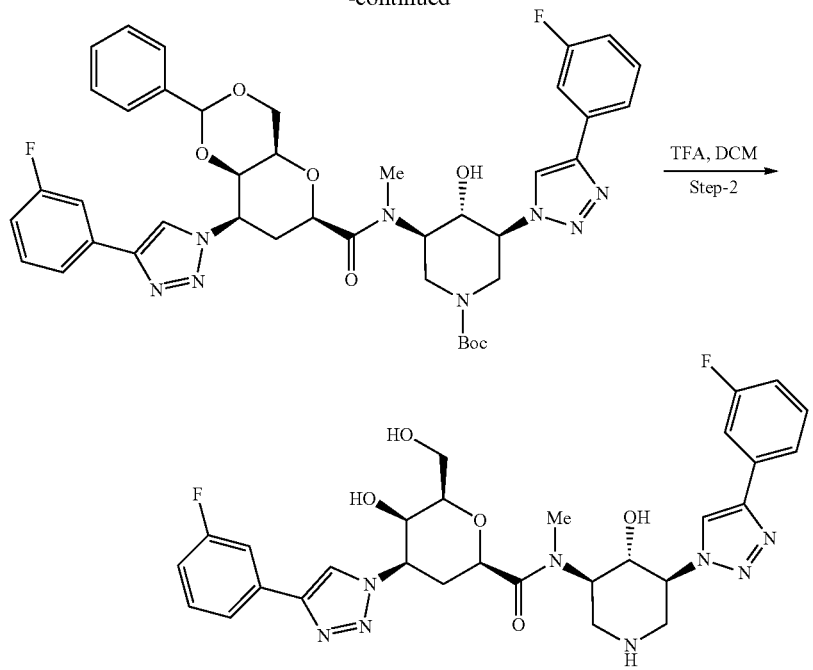

Example 17a & 17b

Step-1: Synthesis of tert-butyl (3S,4S,5R)-3-(4-(3-fluorophenyl)-1H-1,2,3-triazol-1-yl)-5-((4aR,6R,8R,8aR)-8-(4-(3-fluorophenyl)-1H-1,2,3-triazol-1-yl)-N-methyl-2-phenylhexahydropyrano[3,2-d][1,3]dioxine-6-carboxamido)-4-hydroxypiperidine-1-carboxylate: To a stirred solution of (4aR,6R,8R,8aR)-8-(4-(3-fluorophenyl)-1H-1,2,3-triazol-1-yl)-2-phenylhexahydropyrano[3,2-d][1,3]dioxine-6-carboxylic acid (50 mg, 0.118 mmol) in DMF (2 mL), DIPEA (0.062 mL, 0.353 mmol) and HATU (67.0 mg, 0.176 mmol) were added sequentially at rt and stirred for 15 min. Then (3S,4S,5R)-tert-butyl 3-(4-(3-fluorophenyl)-1H-1,2,3-triazol-1-yl)-4-hydroxy-5-(methylamino)piperidine-1-carboxylate (50.6 mg, 0.129 mmol) was added and stirred the reaction mixture at rt for 1 h. The reaction mixture was quenched with ice water and stirred for 15 minutes. The resultant solid was filtered and dried to afford crude residue. The crude residue was purified by silica gel (5-10% MeOH in chloroform) to afford (3S,4S,5R)-tert-butyl 3-(4-(3-fluorophenyl)-1H-1,2,3-triazol-1-yl)-5-((4aR,6R,8R,8aR)-8-(4-(3-fluorophenyl)-1H-1,2,3-triazol-1-yl)-N-methyl-2-phenylhexahydropyrano[3,2-d][1,3]dioxine-6-carboxamido)-4-hydroxypiperidine-1-carboxylate as the diastereomeric mixture which was further purified by chiral SFC to afford the two isomers:

Prep SFC Method Info:
 Column/dimensions: Chiralcel OJ-H(250×21)mm, 5 u
 % CO2: 80%
 % Co solvent: 20% of IPA+ACN
 Total Flow: 70.0 g/min
 Back Pressure: 100 bar
 Temperature: 25° C.
 UV: 244 nm
Analytical Chiral SFC Conditions:
 Analytical Column: ChiralCel OJH (250×4.6)mm, 5 u
 BPR pressure: 100 bars
 Temperature: 22.3° C.
 Flow rate: 3 g/min
 Mobile Phase: CO$_2$/IPA+ACN (75/25)
 Detector Wavelength: UV 200-400 nm
 Isomer 1: (28 mg, 0.035 mmol, 30%); chiral SFC $t_R$=3.74 min; LC-MS, [M+H]$^+$=799.1, {Method F: $t_R$=3.888 min};
 Isomer 2: (29 mg, 0.034 mmol, 29%); chiral SFC $t_R$=5.91 min; LC-MS, [M+H]$^+$=799.2, {Method F: $t_R$=3.505 min};

Step-2: To a solution of (3S,4S,5R)-tert-butyl 3-(4-(3-fluorophenyl)-1H-1,2,3-triazol-1-yl)-5-((4aR,6R,8R,8aR)-8-(4-(3-fluorophenyl)-1H-1,2,3-triazol-1-yl)-N-methyl-2-phenylhexahydropyrano[3,2-d][1,3]dioxine-6-carboxamido)-4-hydroxypiperidine-1-carboxylate (Isomer 1) (28 mg, 0.035 mmol) in DCM (1 mL), trifluoroacetic acid (0.15 mL, 1.947 mmol) was added and stirred for 2 h. Then, the solvent was removed under reduced pressure to get crude residue. The crude material was purified via preparative HPLC Method A to afford Example 17a: (2R,4R,5R,6R)-4-(4-(3-fluorophenyl)-1H-1,2,3-triazol-1-yl)-N-((3R,4S,5S)-5-(4-(3-fluorophenyl)-1H-1,2,3-triazol-1-yl)-4-hydroxypiperidin-3-yl)-5-hydroxy-6-(hydroxymethyl)-N-methyltetrahydro-2H-pyran-2-carboxamide Isomer 1 (10.9 mg, 50%) as an off-white solid. LC-MS, [M+H]$^+$=611.3, {Method A: $t_R$=1.257}. 1H NMR (400 MHz, MEOH-d4) δ ppm 8.53-8.46 (m, 2H), 7.71-7.59 (m, 4H), 7.52-7.42 (m, 2H), 7.15-7.06 (m, 2H), 5.13 (d, J=12.5 Hz, 1H), 4.81-4.74 (m, 1H), 4.68 (dd, J=9.2, 6.5 Hz, 1H), 4.56-4.35 (m, 2H), 4.14 (s, 1H), 4.01-3.56 (m, 5H), 3.48-3.36 (m, 1H), 3.25, 3.00 (two singlets, 3H), 3.06 (q, J=7.3 Hz, 1H), 2.91-2.79 (m, 1H), 2.25-2.14 (m, 1H) {Rotameric Mixture}; hGal3 IC50=5.2 µM.

EXAMPLE 17b

To a solution of (3S,4S,5R)-tert-butyl 3-(4-(3-fluorophenyl)-1H-1,2,3-triazol-1-yl)-5-((4aR,6R,8R,8aR)-8-(4-(3-fluorophenyl)-1H-1,2,3-triazol-1-yl)-N-methyl-2-phenylhexahydropyrano[3,2-d][1,3]dioxine-6-carboxamido)-4-hydroxypiperidine-1-carboxylate Isomer 2 (29 mg, 0.036 mmol) in DCM (1 mL), trifluoroacetic acid (0.15 mL, 1.947 mmol) was added at rt and stirred for 2 h. Then, the solvent was removed under reduced pressure to get crude residue. The crude material was purified via preparative LC/MS Method A to afford ((2R,4R,5R,6R)-4-(4-(3-fluorophenyl)-1H-1,2,3-triazol-1-yl)-N-((3R,4S,5S)-5-(4-(3-fluorophenyl)-1H-1,2,3-triazol-1-yl)-4-hydroxypiperidin-3-yl)-5-hydroxy-6-(hydroxymethyl)-N-methyltetrahydro-2H-pyran-2-carboxamide Isomer 2 (6.7 mg, 0.011 mmol, 30%) as an off-white solid. LC-MS, [M+H]$^+$=611.3, {Method A: $t_R$=1.255}. 1H NMR (400 MHz, MEOH-d4) δ ppm 8.54-8.46 (m, 2H), 7.70-7.57 (m, 4H), 7.51-7.41 (m, 2H), 7.14-7.05 (m, 2H), 5.15-5.06 (m, 1H), 4.95-4.86 (m, 1H), 4.74-4.61 (m, 1H), 4.48-4.41 (m, 1H), 4.32 (td, J=10.9, 4.3 Hz, 1H), 4.10 (s, 1H), 4.01-3.70 (m, 5H), 3.57-3.43 (m, 1H), 3.24, 2.99 (two singlets, 3H), 3.05 (q, J=7.4 Hz, 1H), 2.85-2.69 (m, 1H), 2.32-2.15 (m, 1H) {Rotameric Mixture}. hGal3 IC50=0.13 μM.

EXAMPLE 18a AND 18b

Synthesis of (2R,3R,4S,5R,6R)-4-(4-(3-fluorophenyl)-1H-1,2,3-triazol-1-yl)-N-((3S,4R,5R)-5-(4-(3-fluorophenyl)-1H-1,2,3-triazol-1-yl)-4-hydroxypiperidin-3-yl)-3,5-dihydroxy-6-(hydroxymethyl)-N-methyltetrahydro-2H-pyran-2-carboxamide (Isomer 1 and 2)

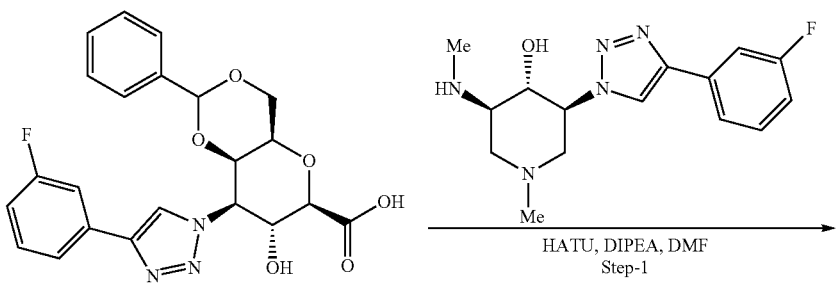

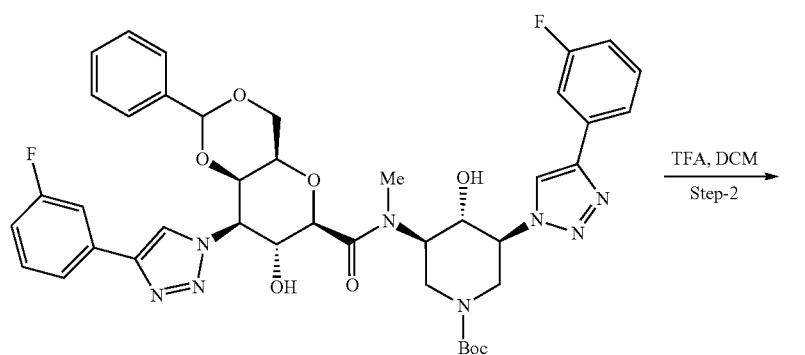

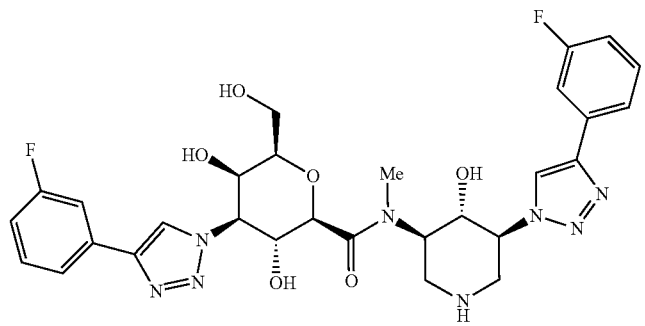

Example 18a & 18b

Step-1: To a stirred solution of (4aR,6R,7R,8R,8aR)-8-(4-(3-fluorophenyl)-1H-1,2,3-triazol-1-yl)-7-hydroxy-2-phenylhexahydropyrano[3,2-d][1,3]dioxine-6-carboxylic acid (50 mg, 0.113 mmol) in DMF (2 mL), DIPEA (0.059 mL, 0.340 mmol) and HATU to (64.6 mg, 0.170 mmol) were added sequentially at rt and stirred for 15 min. Then (3S,4S,5R)-tert-butyl 3-(4-(3-fluorophenyl)-1H-1,2,3-triazol-1-yl)-4-hydroxy-5-(methylamino)piperidine-1-carboxylate (48.8 mg, 0.125 mmol) was added and stirred the reaction mixture at rt for 1 h. The reaction mixture was quenched with ice water and stirred for 15 minutes. The resultant solid was filtered and dried to afford crude residue. The crude residue was purified by silica gel (5-10% MeOH in Chloroform) to afford (3S,4S,5R)-tert-butyl 3-(4-(3-fluorophenyl)-1H-1,2,3-triazol-1-yl)-5-((4aR,6R,7R,8R,8aR)-8-(4-(3-fluorophenyl)-1H-1,2,3-triazol-1-yl)-7-hydroxy-N-methyl-2-phenylhexahydropyrano[3,2-d][1,3]dioxine-6-carboxamido)-4-hydroxypiperidine-1-carboxylate as the diastereomeric mixture which was further purified by prep-HPLC Method C to afford the two isomers:
Analytical HPLC Conditions:
  Analytical Column: Symmetry C9 (250×4.6)mm, 5 u
  Mobile Phase A: 0.1% TFA in Water
  Mobile Phase B: ACN
  Flow rate: 1 mL/min
  Gradient: 20-100% B over 20 minutes, then a 10-minute hold at 100% B
  Detector Wavelength: UV 200-400 nm
  Isomer 1: (25 mg, 0.030 mmol, 27%); HPLC $t_R$=16.083 min; LC-MS, [M+H]$^+$=815.0, {Method F: $t_R$=2.683 min}.
  Isomer 2: (21 mg, 0.025 mmol, 22%); HPLC $t_R$=16.700 min; LC-MS, [M+H]$^+$=815.2, {Method F: $t_R$=3.98 min}.
Step-2: To a solution of (3S,4S,5R)-tert-butyl 3-(4-(3-fluorophenyl)-1H-1,2,3-triazol-1-yl)-5-((4aR,6R,7R,8R,8aR)-8-(4-(3-fluorophenyl)-1H-1,2,3-triazol-1-yl)-7-hydroxy-N-methyl-2-phenylhexahydropyrano[3,2-d][1,3]dioxine-6-carboxamido)-4-hydroxypiperidine-1-carboxylate Isomer 1(25 mg, 0.031 mmol) in DCM (1 mL), trifluoroacetic acid (0.15 mL, 1.947 mmol) was added at rt and stirred for 2 h. Then, the solvent was removed under reduced pressure to get crude residue. The crude material was purified via preparative HPLC Method D to afford Example 18a: (2R,3R,4S,5R,6R)-4-(4-(3-fluorophenyl)-1H-1,2,3-triazol-1-yl)-N-((3R,4S,5S)-5-(4-(3-fluorophenyl)-1H-1,2,3-triazol-1-yl)-4-hydroxypiperidin-3-yl)-3,5-dihydroxy-6-(hydroxymethyl)-N-methyltetrahydro-2H-pyran-2-carboxamide Isomer 1 (8 mg, 41% yield) as an off-white solid. LC-MS, [M+H]$^+$=627.2, {Method C: $t_R$=1.500}. 1H NMR (400 MHz, MEOH-d4) δ ppm 8.44, 8.43 (two singlets, 1H), 8.36, 8.34 (two singlets, 1H), 7.70-7.56 (m, 4H), 7.50-7.41 (m, 2H), 7.13-7.04 (m, 2H), 4.98-4.90 (m, 1H), 4.80-4.75 (m, 1H), 4.65-4.50 (m, 2H), 4.44 (d, J=9.0 Hz, 1H), 4.37-4.28 (m, 1H), 4.23 (td, J=10.7, 4.8 Hz, 1H), 4.14 (d, J=2.5 Hz, 1H), 4.01 (dd, J=8.3, 3.8 Hz, 1H), 3.93-3.77 (m, 2H), 3.75-3.69 (m, 2H), 3.43-3.34 (m, 1H), 3.24 (s, 1H), 3.22-3.12 (m, 2H) [*rotameric mixture]; hGal3 IC50=1.8 µM.

EXAMPLE 18b

To a solution of (3S,4S,5R)-tert-butyl 3-(4-(3-fluorophenyl)-1H-1,2,3-triazol-1-yl)-5-((4aR,6R,7R,8R,8aR)-8-(4-(3-fluorophenyl)-1H-1,2,3-triazol-1-yl)-7-hydroxy-N-methyl-2-phenylhexahydropyrano[3,2-d][1,3]dioxine-6-carboxamido)-4-hydroxypiperidine-1-carboxylate Isomer 2(16 mg, 0.020 mmol) in DCM (1 mL), trifluoroacetic acid (0.15 mL, 1.947 mmol) was added at rt and stirred for 2 h. Then, the solvent was removed under reduced pressure to get crude residue. The crude material was purified via preparative LC/MS Method A to afford (2R,3R,4S,5R,6R)-4-(4-(3-fluorophenyl)-1H-1,2,3-triazol-1-yl)-N-((3R,4S,5S)-5-(4-(3-fluorophenyl)-1H-1,2,3-triazol-1-yl)-4-hydroxypiperidin-3-yl)-3,5-dihydroxy-6-(hydroxymethyl)-N-methyltetrahydro-2H-pyran-2-carboxamide Isomer 2 (2.8 mg, 22%) as an off-white solid. LC-MS, [M+H]$^+$=627.1, {Method A: $t_R$=1.517}. 1H NMR (400 MHz, MEOH-d4) δ ppm 8.55 (d, J=2.9 Hz, 1H), 8.53 (d, J=2.4 Hz, 1H), 7.72-7.66 (m, 2H), 7.64 (d, J=7.6 Hz, 2H), 7.53-7.44 (m, 2H), 7.16-7.07 (m, 2H), 4.97 (dd, J=10.6, 2.8 Hz, 1H), 4.80-4.73 (m, 1H), 4.48-4.39 (m, 2H), 4.16 (d, J=3.4 Hz, 1H), 4.05 (d, J=5.4 Hz, 1H), 3.94-3.70 (m, 6H), 3.55-3.46 (m, 1H), 3.29, 3.02 (two singlets, 3H), 3.06 (d, J=7.8 Hz, 1H), {Rotameric mixture}. hGal3 IC50=0.05 µM.

EXAMPLE 19

Synthesis of (2R,3R,4S,5R,6R)-4-(4-(3-fluorophenyl)-1H-1,2,3-triazol-1-yl)-N-((3S,4R,5R)-5-(4-(3-fluorophenyl)-1H-1,2,3-triazol-1-yl)-4-hydroxy-1-methylpiperidin-3-yl)-5-hydroxy-6-(hydroxymethyl)-3-methoxy-N-methyltetrahydro-2H-pyran-2-carboxamide

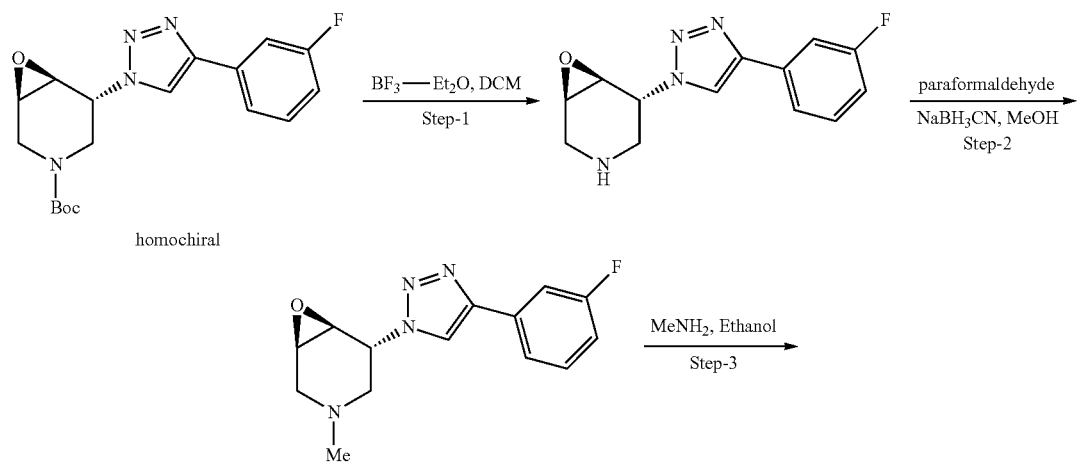

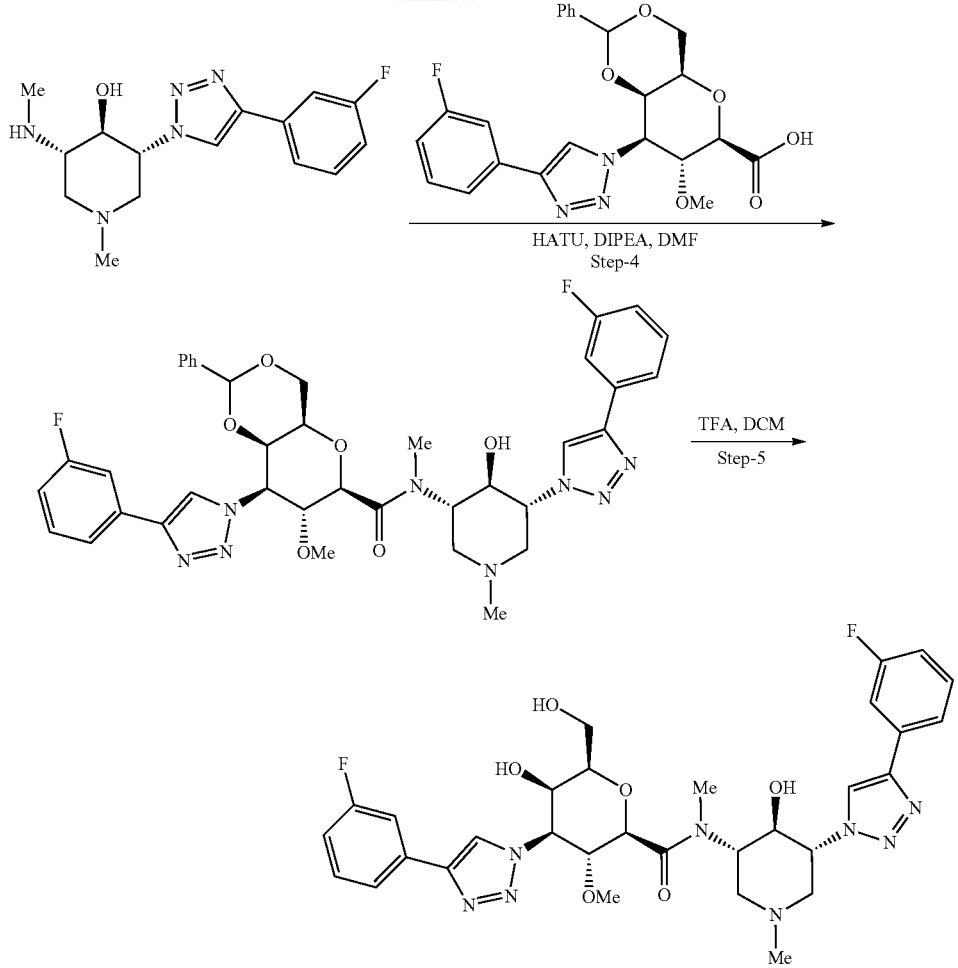

Example 19

Step-1: Synthesis of (1R,5R,6S)-5-(4-(3-fluorophenyl)-1H-1,2,3-triazol-1-yl)-7-oxa-3-azabicyclo[4.1.0]heptane (homochiral): To a stirred solution of tert-butyl (1R,5R,6S)-5-(4-(3-fluorophenyl)-1H-1,2,3-triazol-1-yl)-7-oxa-3-azabicyclo[4.1.0]heptane-3-carboxylate (100 mg, 0.277 mmol) in dichloromethane (5 mL), 100 mg of 4 A molecular sieves and BF$_3$·OEt$_2$ (0.105 mL, 0.832 mmol) were added sequentially at rt and stirred for 30 min. The reaction mixture was filtered through a Celite pad, washed with excess DCM (20 mL) and the filtrate was concentrated under reduced pressure to give (1R,5R,6S)-5-(4-(3-fluorophenyl)-1H-1,2,3-triazol-1-yl)-7-oxa-3-azabicyclo[4.1.0]heptane (70 mg, 83% yield) as a pale yellow oil; LC-MS, [M+H]$^+$=261.4, {Method E: t$_R$=0.90 min}.

Step-2: Synthesis of (1R,5R,6S)-5-(4-(3-fluorophenyl)-1H-1,2,3-triazol-1-yl)-3-methyl-7-oxa-3-azabicyclo[4.1.0]heptane: To a stirred solution of (1R,5R,6S)-5-(4-(3-fluorophenyl)-1H-1,2,3-triazol-1-yl)-7-oxa-3-azabicyclo[4.1.0]heptane (70 mg, 0.269 mmol) in MeOH (5 mL), paraformaldehyde (40.4 mg, 1.345 mmol) and 0.1 mL of AcOH was added and stirred for 10 min at rt. Then sodium cyanoborohydride (16.90 mg, 0.269 mmol) was added and stirred at rt for 16 h. MeOH was removed under reduced pressure and the crude residue was extracted with 10% MeOH in DCM (2×30 mL) washed with water, brine, dried over sodium sulphate and concentrated. The residue was purified via silica gel chromatography (20-50% EtOAc in n-hexane) to yield (1R,5R,6S)-5-(4-(3-fluorophenyl)-1H-1,2,3-triazol-1-yl)-3-methyl-7-oxa-3-azabicyclo[4.1.0]heptane (70 mg, 92% yield) as an off-white solid. LC-MS, [M+H]$^+$=275.2, {Method C: t$_R$=1.828 min}.

Step-3: Synthesis of (3R,4R,5S)-3-(4-(3-fluorophenyl)-1H-1,2,3-triazol-1-yl)-1-methyl-5-(methylamino)piperidin-4-ol: (1R,5R,6S)-5-(4-(3-fluorophenyl)-1H-1,2,3-triazol-1-yl)-3-methyl-7-oxa-3-azabicyclo[4.1.0]heptane (70 mg, 0.255 mmol) in methanamine (33% solution in Ethanol) (5 mL, 0.255 mmol) was heated in a sealed tube at 65° C. for 16 h. Reaction mixture was cooled to rt and solvent was removed under reduced pressure to give the title compound (65 mg, 81% yield) as brown solid. LC-MS, [M+H]$^+$=306.2, {Method C: t$_R$=0.833 min}.

Step-4: Synthesis of (4aR,6R,7R,8R,8aR)-8-(4-(3-fluorophenyl)-1H-1,2,3-triazol-1-yl)-N-((3S,4R,5R)-5-(4-(3-fluorophenyl)-1H-1,2,3-triazol-1-yl)-4-hydroxy-1-methylpiperidin-3-yl)-7-methoxy-N-methyl-2-phenylhexahydropyrano[3,2-d][1,3]dioxine-6-carboxamide: To a stirred solution of (4aR,6R,7R,8R,8aR)-8-(4-(3-fluorophenyl)-1H-1,2,3-triazol-1-yl)-7-methoxy-2-phenylhexahydropyrano[3,2-d][1,3]dioxine-6-carboxylic acid (30 mg, 0.066 mmol) in DMF (2 mL), DIPEA (0.035 mL, 0.198 mmol) and HATU (37.6 mg, 0.099 mmol) were added sequentially at rt and stirred for 15 min. Then (3R,4R,5S)-3-(4-(3-fluorophenyl)-1H-1,2,3-triazol-1-yl)-1-methyl-5-(methylamino)piperidin-4-ol (24.14 mg, 0.079 mmol) was added and stirred the reaction mixture at rt for 1 h. The reaction mixture was quenched with ice water and stirred for 15 minutes. The resultant solid was filtered and dried to afford the title compound (35 mg, 55% yield) as brown solid. LC-MS, [M+H]$^+$=743.2, {Method C: $t_R$=2.88 min}.

Step-5: To a solution of (4aR,6R,7R,8R,8aR)-8-(4-(3-fluorophenyl)-1H-1,2,3-triazol-1-yl)-N-((3S,4R,5R)-5-(4-(3-fluorophenyl)-1H-1,2,3-triazol-1-yl)-4-hydroxy-1-methylpiperidin-3-yl)-7-methoxy-N-methyl-2-phenylhexahydropyrano[3,2-d][1,3]dioxine-6-carboxamide (30 mg, 0.040 mmol) in dichloromethane (3 mL), trifluoroacetic acid (0.5 mL, 6.49 mmol) was added at rt and stirred for 2 h. Then, the solvent was removed under reduced pressure to get crude residue. The crude material was purified via prep-HPLC Method D to afford Example 19: (2R,3R,4S,5R,6R)-4-(4-(3-fluorophenyl)-1H-1,2,3-triazol-1-yl)-N-((3S,4R,5R)-5-(4-(3-fluorophenyl)-1H-1,2,3-triazol-1-yl)-4-hydroxy-1-methylpiperidin-3-yl)-5-hydroxy-6-(hydroxymethyl)-3-methoxy-N-methyltetrahydro-2H-pyran-2-carboxamide (18.7 mg, 0.029 mmol, 71%) as an off-white solid. LC-MS, [M+H]$^+$=655.1, {Method A: $t_R$=1.685 min}. $^1$H NMR (400 MHz, MEOH-d$_4$) δ ppm 8.62, 8.59 (two singlets, 1H), 8.41, 8.38 (two singlets, 1H), 7.63-7.48 (m, 4H), 7.42-7.33 (m, 2H), 7.05-6.96 (m, 2H), 4.88 (dd, J=10.1, 3.1 Hz, 1H), 4.54-4.47 (m, 1H), 4.41-4.23 (m, 3H), 4.01 (d, J=2.9 Hz, 1H), 3.89 (d, J=3.2 Hz, 1H), 3.81-3.74 (m, 2H), 3.71-3.59 (m, 4H), 3.17-3.15 (m, 3H), 3.05-2.86 (m, 6H), 2.75 (s, 1H) {Rotameric mixture}. hGal3 IC50=0.02 µM.

EXAMPLE 20a AND 20b

Synthesis of (2R,3R,4S,5R,6R)-4-(4-(3-fluorophenyl)-1H-1,2,3-triazol-1-yl)-N-((3R,4S,5S)-5-(4-(3-fluorophenyl)-1H-1,2,3-triazol-1-yl)-4-hydroxytetrahydro-2H-pyran-3-yl)-5-hydroxy-6-(hydroxymethyl)-3-methoxytetrahydro-2H-pyran-2-carboxamide (Isomer 1 and 2)

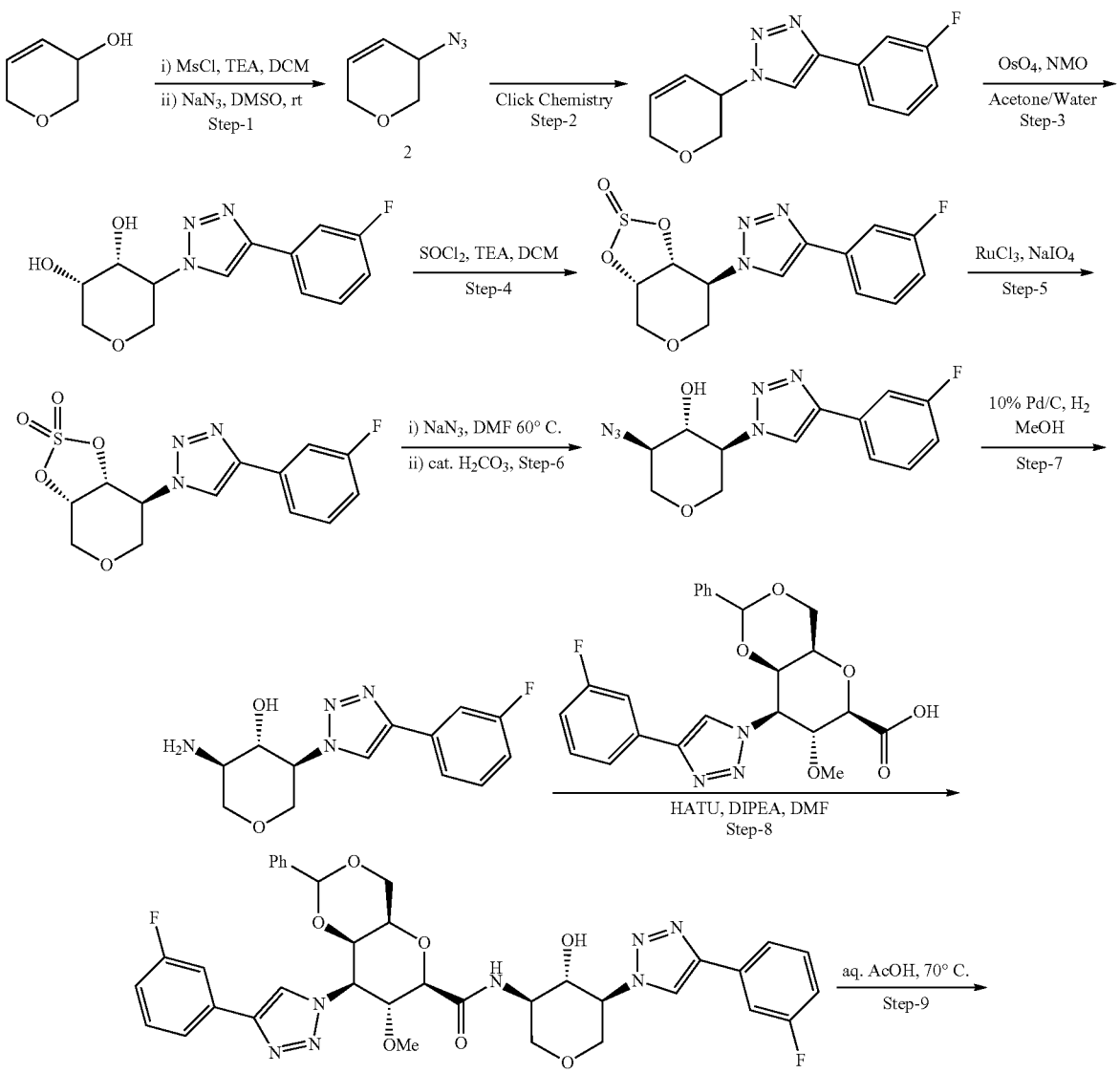

-continued

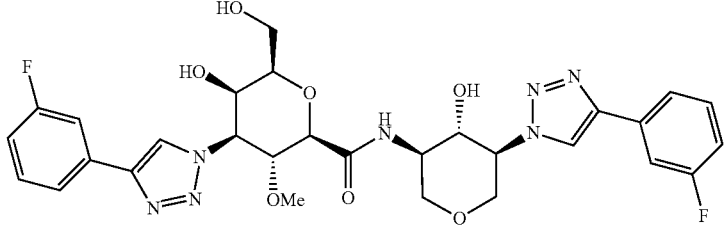

Example 20a & 20b

Step-1: Synthesis of 3-azido-3,6-dihydro-2H-pyran: To a stirred solution of 3,6-dihydro-2H-pyran-3-ol (1 g, 9.99 mmol) in DCM (50 mL), triethylamine (2.78 mL, 19.98 mmol) and mesyl-Cl (0.934 mL, 11.99 mmol) were added sequentially at 0° C. under $N_2$ and stirred for 30 min. Then the reaction mixture was extracted with DCM (100 mL), washed with water, brine, dried over sodium sulphate and concentrated. The crude mesylate was dissolved in DMSO (10 mL), sodium azide (2.74 g, 42.1 mmol) was added and stirred at rt for 16 h. The reaction mixture was extracted with EtOAc (3×50 mL), washed with water, brine and dried over sodium sulphate. Solvent was removed under reduced pressure to get crude residue which was purified by flash chromatography (15-20% EtOAc in n-hexane) to afford 3-azido-3,6-dihydro-2H-pyran (0.75 g, 5.95 mmol, 71%). $^1$H NMR (400 MHz, CHLOROFORM-d) δ ppm 6.07-6.22 (m, 1H), 5.84-5.97 (m, 1H), 4.18-4.25 (m, 1H), 4.07-4.15 (m, 1H), 3.96 (ddd, J=12.0, 3.0, 1.0 Hz, 1H), 3.81-3.86 (m, 1H), 3.55 (br. s, 1H).

Step-2: Synthesis of 1-(3,6-dihydro-2H-pyran-3-yl)-4-(3-fluorophenyl)-1H-1,2,3-triazole: To a solution of 3-azido-3,6-dihydro-2H-pyran (0.74 g, 5.91 mmol) in DMF (10 mL) and water (3 mL) was added sodium ascorbate (1.172 g, 5.91 mmol), copper(II) sulfate pentahydrate (1.329 g, 5.32 mmol) and 3-fluorophenylacetylene (2.73 mL, 23.66 mmol). The reaction mixture was degassed $N_2$ for 10 min and heated at 85° C. for 15 min. Then the reaction mixture was cooled to rt, diluted with DCM (50 mL)/water (50 mL) and stirred for 30 minutes. The organic layer was separated and aqueous layer was re-extracted with DCM (2×30 mL). Combined organic extracts were washed with water, brine, dried over sodium sulphate and concentrated. The crude residue was purified by flash chromatography (35-50% EtOAc in n-hexane) to afford the title compound (1.36 g, 5.45 mmol, 92%) as pale yellow solid. LC-MS, [M+H]$^+$=246.2, {Method C: $t_R$=2.006 min}.

Step-3: Synthesis of (3S,4R,5S)-5-(4-(3-fluorophenyl)-1H-1,2,3-triazol-1-yl)tetrahydro-2H-pyran-3,4-diol (racemate):To a stirred solution of 1-(3,6-dihydro-2H-pyran-3-yl)-4-(3-fluorophenyl)-1H-1,2,3-triazole (0.4 g, 1.631 mmol) in acetone (4 mL) and water (1 mL), was added 4-methylmorpholine-N-oxide (0.287 g, 2.446 mmol) and osmium tetroxide (2.048 mL, 0.163 mmol, 2.5% w/v in t-butanol) at rt and stirred for 14 h. The reaction mixture was quenched with sat.Na$_2$SO$_3$ solution and acetone was removed under reduced pressure to give crude residue. The crude residue was extracted with EtOAc (2×100 mL), washed with water, brine, dried over sodium sulphate and concentrated. The crude residue was purified by flash chromatography (80-100% EtOAc in n-hexane) to afford the title compound (0.25 g, 0.895 mmol, 55%). LC-MS, [M+H]$^+$=280.2, {Method C: $t_R$=1.025 min}.

Step-4: Synthesis of (3aS,7S,7aR)-7-(4-(3-fluorophenyl)-1H-1,2,3-triazol-1-yl)tetrahydro-3aH-[1,3,2]dioxathiolo[4,5-c]pyran 2,2-dioxide (racemate): To a stirred solution of (3S,4R,5S)-5-(4-(3-fluorophenyl)-1H-1,2,3-triazol-1-yl)tetrahydro-2H-pyran-3,4-diol (0.25 g, 0.895 mmol) in DCM (10 mL) was added TEA (0.250 mL, 1.790 mmol) at rt and stirred for 5 min. Then the reaction mixture was cooled 0° C. and SOCl$_2$ (0.131 mL, 1.790 mmol) was added under N$_2$. Reaction mixture was allowed to reach rt and stirred at rt for 1 h. Solvent was removed under reduced pressure, crude was extracted with EtOAc (2×50 mL), washed with water, brine and dried over sodium sulphate. The solvent was removed under reduced pressure and crude residue was purified by flash chromatography (60-95% of EtOAc in n-hexane) to afford the title compound (0.23 g, 0.707 mmol, 79%). LC-MS, [M+H]$^+$=326.4, {Method E: $t_R$=1.08 min}.

Step-5: Synthesis of (3aS,7S,7aR)-7-(4-(3-fluorophenyl)-1H-1,2,3-triazol-1-yl)tetrahydro-3aH-[1,3,2]dioxathiolo[4,5-c]pyran 2,2-dioxide (racemate): To a stirred solution of (3aS,7S,7aR)-7-(4-(3-fluorophenyl)-1H-1,2,3-triazol-1-yl)tetrahydro-3aH-[1,3,2]dioxathiolo[4,5-c]pyran 2-oxide (0.2 g, 0.615 mmol) in acetonitrile (3 mL) and water (1 mL), was added sodium periodate (0.263 g, 1.230 mmol) and ruthenium(III) chloride hydrate (0.014 g, 0.061 mmol) at rt and stirred for 12 h. Solvent was removed under reduced pressure, crude was extracted with EtOAc (2×50 mL), washed with water, brine and dried over sodium sulphate. The solvent was removed under reduced pressure and crude residue was purified by flash chromatography (80-100% of EtOAc in n-hexane) to afford the title compound (160 mg, 0.469 mmol, 76%). LC-MS, [M+H]$^+$=342.2, {Method F: $t_R$=2.028 min}.

Step-6: Synthesis of (3R,4R,5S)-3-azido-5-(4-(3-fluorophenyl)-1H-1,2,3-triazol-1-yl)tetrahydro-2H-pyran-4-ol (racemate): To a stirred solution of (3aS,7S,7aR)-7-(4-(3-fluorophenyl)-1H-1,2,3-triazol-1-yl)tetrahydro-3aH-[1,3,2]dioxathiolo[4,5-c]pyran 2,2-dioxide (160 mg, 0.469 mmol) in DMF (4 mL) was added sodium azide (122 mg, 1.875 mmol) at rt. Then the reaction mixture was heated at 60° C. for 3 h. Reaction mixture was cooled to rt and solvent was removed under reduced pressure to give crude residue. The crude residue was dissolved in THF (2 mL), 1 mL of stock solution [1 mL H$_2$SO$_4$+0.4 mL of water+8.6 mL of THF] was added at 0° C. and stirred for 30 min. The reaction mixture was basified with NaHCO$_3$, filtered thorough Celite pad and washed with excess EtOAc. The filtrate was concentrated under reduced pressure to give crude residue which was purified by flash chromatography (60-95% of EtOAc in n-hexane) to afford the title compound (90 mg, 0.296 mmol, 63%). LC-MS, [M+H]$^+$=305.2, {Method C: $t_R$=1.94 min}.

Step-7: Synthesis of (3R,4S,5S)-3-amino-5-(4-(3-fluorophenyl)-1H-1,2,3-triazol-1-yl)tetrahydro-2H-pyran-4-ol (racemate): To a stirred solution of (3R,4R,5S)-3-azido-5-(4-(3-fluorophenyl)-1H-1,2,3-triazol-1-yl)tetrahydro-2H-pyran-4-ol (90 mg, 0.296 mmol) in MeOH (4 mL), was added 10% Pd/C (6.30 mg, 0.030 mmol) and stirred at rt under hydrogen atmosphere for 16 h. The reaction mixture filtered through celite, washed with excess MeOH and the filtrate was concentrated to afford the title compound (60 mg, 0.216 mmol, 73%). LC-MS, [M+H]$^+$=279.5, {Method E: $t_R$=0.72 min}

Step-8: To a stirred solution of (3R,4S,5S)-3-amino-5-(4-(3-fluorophenyl)-1H-1,2,3-triazol-1-yl)tetrahydro-2H-pyran-4-ol (45.8 mg, 0.165 mmol) in DMF (2 mL), was added DIPEA (0.192 mL, 1.098 mmol) at rt. After 5 min, (4aR,6R,7R,8R,8aR)-8-(4-(3-fluorophenyl)-1H-1,2,3-triazol-1-yl)-7-methoxy-2-phenylhexahydropyrano[3,2-d][1,3]dioxine-6-carboxylic acid (50 mg, 0.110 mmol) and HATU (104 mg, 0.274 mmol) were added and the reaction mixture was stirred at rt for 12 h. Then the reaction mixture was diluted with ice cold water and stirred for 10 min. The obtained solid was filtered and dried to afford crude residue containing (4aR,6R,7R,8R,8aR)-8-(4-(3-fluorophenyl)-1H-1,2,3-triazol-1-yl)-N-((3R,4S,5S)-5-(4-(3-fluorophenyl)-1H-1,2,3-triazol-1-yl)-4-hydroxytetrahydro-2H-pyran-3-yl)-7-methoxy-2-phenylhexahydropyrano[3,2-d][1,3]dioxine-6-carboxamide as a diasteromeric mixture. The crude residue was purified by prep-HPLC to separate the two diastereomers.

Prep HPLC Method info: Column: Lux-cellulose C4(250×21.2)mm, 5 micron;
Mobile.Phase A:-Mobile.Phase B: 0.1% DEA IN MeOH; Flow: 19 mL/min;
Time(min)/% B: 0/100, 20/100;
Isomer 1: (20 mg, 0.028 mmol, 25.5% yield) LC-MS, [M+H]$^+$=716.0, {Method F: $t_R$=2.287 min}
Isomer 2: (18 mg, 0.025 mmol, 22.91% yield). LC-MS, [M+H]$^+$=716.0, {Method F: $t_R$=2.30 min}

Step-9: (4aR,6R,7R,8R,8aR)-8-(4-(3-fluorophenyl)-1H-1,2,3-triazol-1-yl)-N-((3R,4S,5S)-5-(4-(3-fluorophenyl)-1H-1,2,3-triazol-1-yl)-4-hydroxytetrahydro-2H-pyran-3-yl)-7-methoxy-2-phenylhexahydropyrano[3,2-d][1,3]dioxine-6-carboxamide Isomer 1 (20 mg, 0.028 mmol) was suspended in 80% Aq.AcOH (1 mL) and heated at 70° C. for 14 h. Then, reaction mixture was cooled to rt and solvent was removed under reduced pressure to give crude residue. The crude material was purified via preparative HPLC [Method A] to afford Example 20a: (2R,3R,4S,5R,6R)-4-(4-(3-fluorophenyl)-1H-1,2,3-triazol-1-yl)-N-((3R,4S,5S)-5-(4-(3-fluorophenyl)-1H-1,2,3-triazol-1-yl)-4-hydroxytetrahydro-2H-pyran-3-yl)-5-hydroxy-6-(hydroxymethyl)-3-methoxytetrahydro-2H-pyran-2-carboxamide Isomer 1 (5 mg, 7.89 μmol, 28%). LC-MS, [M+H]$^+$=628.1, {Method A: $t_R$=1.618 min}; 1H NMR (400 MHz, MEOH-d4) δ=8.63 (s, 1H), 8.48 (s, 1H), 7.70 (dd, J=7.7, 3.1 Hz, 2H), 7.66-7.61 (m, 2H), 7.53-7.46 (m, 2H), 7.13 (td, J=8.1, 4.0 Hz, 2H), 4.95 (dd, J=10.6, 2.8 Hz, 1H), 4.67 (d, J=4.4 Hz, 1H), 4.35-4.25 (m, 3H), 4.21 (dd, J=10.3, 4.9 Hz, 1H), 4.15 (d, J=2.7 Hz, 1H), 4.11-4.05 (m, 1H), 4.03-3.94 (m, 2H), 3.87-3.81 (m, 2H), 3.79-3.73 (m, 1H), 3.47 (t, J=10.9 Hz, 1H), 3.20 (s, 3H). hGal3 IC$_{50}$=36 μM.

EXAMPLE 20b (2R,3R,4S,5R,6R)-4-(4-(3-fluorophenyl)-1H-1,2,3-triazol-1-yl)-N-((3R,4S,5S)-5-(4-(3-fluorophenyl)-1H-1,2,3-triazol-1-yl)-4-hydroxytetrahydro-2H-pyran-3-yl)-5-hydroxy-6-(hydroxymethyl)-3-methoxytetrahydro-2H-pyran-2-carboxamide Isomer 2 (5.5 mg, 8.76 μmol, 34.8% yield) was prepared following the same procedure used in step 9 for example 20a but using (4aR,6R,7R,8R,8aR)-8-(4-(3-fluorophenyl)-1H-1,2,3-triazol-1-yl)-N-((3R,4S,5S)-5-(4-(3-fluorophenyl)-1H-1,2,3-triazol-1-yl)-4-hydroxytetrahydro-2H-pyran-3-yl)-7-methoxy-2-phenylhexahydropyrano[3,2-d][1,3]dioxine-6-carboxamide Isomer 2 as starting material. LC-MS, [M+H]$^+$=628.1, {Method A: $t_R$=1.610 min}. $^1$H NMR (400 MHz, MEOH-d$_4$) δ=8.63 (s, 1H), 8.48 (s, 1H), 7.70 (dd, J=7.7, 3.1 Hz, 2H), 7.66-7.61 (m, 2H), 7.53-7.46 (m, 2H), 7.13 (td, J=8.1, 4.0 Hz, 2H), 4.95 (dd, J=10.6, 2.8 Hz, 1H), 4.67 (d, J=4.4 Hz, 1H), 4.35-4.25 (m, 3H), 4.21 (dd, J=10.3, 4.9 Hz, 1H), 4.15 (d, J=2.7 Hz, 1H), 4.11-4.05 (m, 1H), 4.03-3.94 (m, 2H), 3.87-3.81 (m, 2H), 3.79-3.73 (m, 1H), 3.47 (t, J=10.9 Hz, 1H), 3.20 (s, 3H). hGal3 IC$_{50}$=0.09 μM.

EXAMPLE 21

Synthesis of (2R,3R,4S,5R,6R)-4-(4-(3-fluorophenyl)-1H-1,2,3-triazol-1-yl)-N-((3R,4S,5S)-5-(4-(3-fluorophenyl)-1H-1,2,3-triazol-1-yl)-4-hydroxytetrahydro-2H-pyran-3-yl)-5-hydroxy-6-(hydroxymethyl)-3-methoxytetrahydro-2H-pyran-2-carboxamide

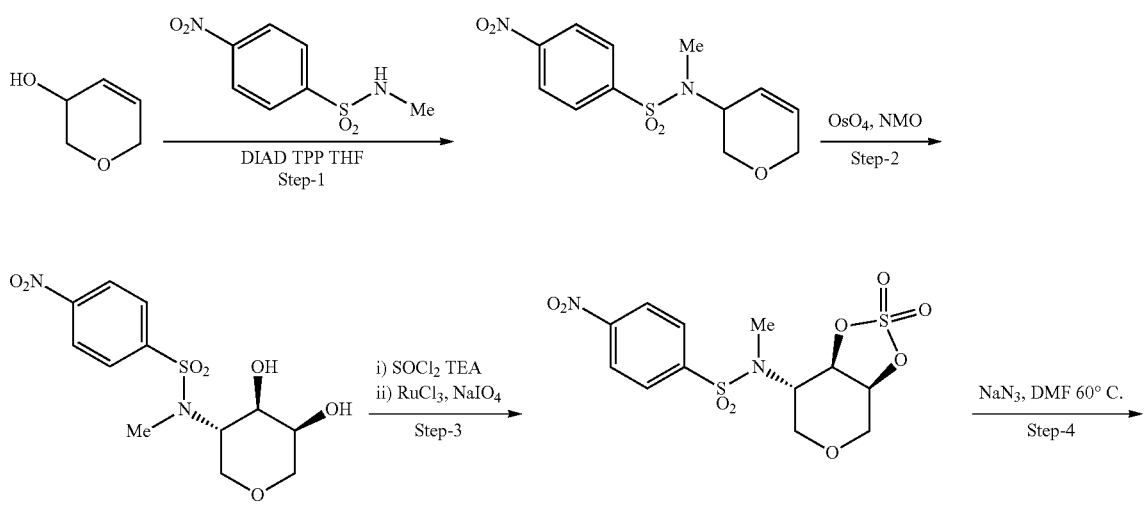

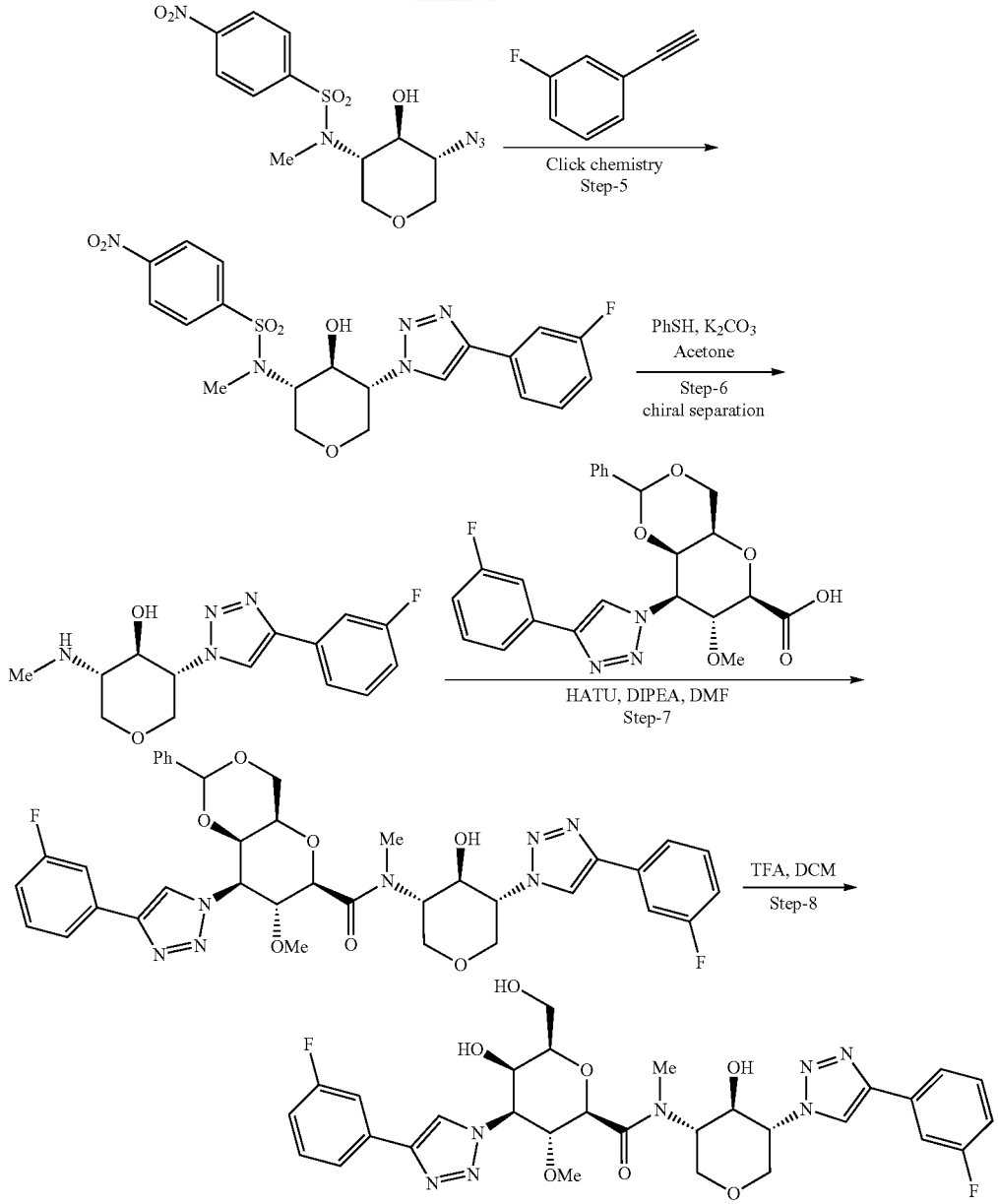

Example 21

Step-1: Synthesis of N-(3,6-dihydro-2H-pyran-3-yl)-N-methyl-4-nitrobenzenesulfonamide (racemate): To a stirred solution of 3,6-dihydro-2H-pyran-3-ol (1.667 g, 16.65 mmol), N-methyl-4-nitrobenzenesulfonamide (3.0 g, 13.88 mmol) in THF (30 mL), was added triphenylphosphine (7.28 g, 27.8 mmol) and DIAD (5.40 mL, 27.8 mmol) at 0 oC. The mixture was allowed to warm to rt and stirred for 18 h. The reaction mixture was extracted with EtOAc (3×50 mL), washed with water, brine, dried over sodium sulphate and concentrated. The crude residue was purified by flash chromatography (0-30% EtOAc in n-hexane) to afford the title compound (4 g, 13.41 mmol, 97%) as an off-white solid. 1H NMR (400 MHz, CHLOROFORM-d) δ ppm 8.34-8.41 (m, 2H), 7.97-8.08 (m, 2H), 6.02-6.09 (m, 1H), 5.36-5.42 (m, 1H), 4.37-4.43 (m, 1H), 4.08-4.15 (m, 1H), 3.96-4.04 (m, 1H), 3.76 (d, J=4.0 Hz, 2H), 2.92 (s, 3H).

Step-2: Synthesis of N-((3S,4R,5S)-4,5-dihydroxytetrahydro-2H-pyran-3-yl)-N-methyl-4-nitrobenzenesulfonamide (racemate): To a stirred solution of N-(3,6-dihydro-2H-pyran-3-yl)-N-methyl-4-nitrobenzenesulfonamide (4.0 g, 13.41 mmol) in acetone (50 mL) and water (13.33 mL) was added 4-methylmorpholine-N-oxide (2.356 g, 20.11 mmol) and osmium tetroxide (5.05 mL, 0.402 mmol, 2.5% w/v in t-butanol) at rt and stirred for 16 h. The reaction mixture was quenched with sat.Na2SO3 solution and acetone was removed under reduced pressure to give crude residue. The crude was extracted with EtOAc (2×100 mL), washed with water, brine, dried over sodium sulphate and concentrated. The residue was purified by flash chromatography (80-100% EtOAc in n-hexane) to afford the title compound (3.5 g, 10.53 mmol, 79%) as an off-white solid. $^1$H NMR (300 MHz, DMSO-d$_6$) δ ppm 8.36 (d, J=8.7 Hz, 2H), 8.06 (d, J=8.7 Hz, 2H), 4.75 (d, J=4.2 Hz, 1H), 4.53 (d, J=6.4 Hz, 1H), 3.98 (br td, J=10.6, 4.9 Hz, 1H), 3.50-3.70 (m, 4H), 3.24-3.37 (m, 2 H, merged with moisture peak), 2.79 (s, 3H).

Step-3: Synthesis of N-((3aS,7S,7aR)-2,2-dioxidotetrahydro-3aH-[1,3,2]dioxathiolo[4,5-c]pyran-7-yl)-N-methyl-4-nitrobenzenesulfonamide (racemate): To a stirred solution of N-((3S,4R,5S)-4,5-dihydroxytetrahydro-2H-pyran-3-yl)-N-methyl-4-nitrobenzenesulfonamide (3.5 g, 10.53 mmol) in DCM (30 mL), TEA (2.94 mL, 21.06 mmol) and thionyl chloride (1.537 mL, 21.06 mmol) were added sequentially at 0° C. and stirred for 1 h. Then the reaction mixture was extracted with DCM (2×75 mL), washed with water, brine and dried over sodium sulphate. Solvent was removed under reduced pressure to give a residue that was taken for the next step without further purification. To a stirred solution of N-methyl-4-nitro-N-((3aS,7S,7aR)-2-oxidotetrahydro-3aH-[1,3,2]dioxathiolo[4,5-c]pyran-7-yl)benzenesulfonamide (3.8 g, 10.04 mmol) in acetonitrile (100 mL)/water (66.7 mL), sodium periodate (4.30 g, 20.09 mmol) and ruthenium (III) chloride hydrate (0.163 g, 0.036 mmol) were added sequentially at 0° C. Then the reaction mixture was allowed to reach rt and stirred for 12 h. The solvent was removed under reduced pressure to give crude residue, crude was extracted with EtOAc (150 mL), washed with water (100 mL), sat NaHSO$_4$ solution (3×50 mL) and dried over Na$_2$SO$_4$. The solvent was removed under reduced pressure to give crude residue which was purified by flash chromatography (70-100% EtOAc in n-hexane) to afford N-((3aS,7S,7aR)-2,2-dioxidotetrahydro-3aH-[1,3,2]dioxathiolo[4,5-c]pyran-7-yl)-N-methyl-4-nitrobenzenesulfonamide (3.5 g, 8.87 mmol, 88%) as an off-white solid. $^1$H NMR (400 MHz, DMSO-d$_6$) δ ppm 8.42 (d, J=9.0 Hz, 2H), 8.06-8.10 (m, 2H), 5.55-5.61 (m, 1H), 5.38-5.42 (m, 1H), 4.23-4.32 (m, 2H), 3.76 (dd, J=14.8, 1.8 Hz, 1H), 3.62-3.68 (m, 1H), 3.48-3.55 (m, 1H), 2.89 (s, 3H).

Step-4: Synthesis of N-((3S,4S,5R)-5-azido-4-hydroxytetrahydro-2H-pyran-3-yl)-N-methyl-4-nitrobenzenesulfonamide (racemate): To a stirred solution of N-((3aS, 7S,7aR)-2,2-dioxidotetrahydro-3aH-[1,3,2]dioxathiolo[4,5-c]pyran-7-yl)-N-methyl-4-nitrobenzenesulfonamide (0.7 g, 1.775 mmol) in DMF (15 mL) was added sodium azide (0.462 g, 7.10 mmol) at rt. Then the reaction mixture was heated at 60° C. for 2 h. Reaction mixture was cooled to rt and solvent was removed under reduced pressure to give crude residue. The crude residue was dissolved in THF (8.6 mL), 0.4 mL of water and 1 mL of H$_2$SO$_4$ was added at 0° C. and stirred for 30 min. The reaction mixture was basified with solid NaHCO$_3$, filtered thorough celite pad and washed with excess EtOAc. The filtrate was concentrated under reduced pressure to give crude residue which was purified by flash chromatography (30-50% of EtOAc in n-hexane) to afford the title compound (0.5 g, 1.352 mmol, 76%). LC-MS, [M+18]$^+$=375.2, {Method C: t$_R$=1.917 min}.

Step-5: Synthesis of N-((3S,4S,5R)-5-(4-(3-fluorophenyl)-1H-1,2,3-triazol-1-yl)-4-hydroxytetrahydro-2H-pyran-3-yl)-N-methyl-4-nitrobenzenesulfonamide (racemate): To a solution of N-((3S,4S,5R)-5-azido-4-hydroxytetrahydro-2H-pyran-3-yl)-N-methyl-4-nitrobenzenesulfonamide (2.2 g, 6.16 mmol) in DMF (20 mL) and water (5.00 mL) was added sodium ascorbate (1.220 g, 6.16 mmol), copper(II) sulfate pentahydrate (1.383 g, 5.54 mmol) and 1-ethynyl-3-fluorobenzene (2.85 mL, 24.63 mmol) at rt. The reaction mixture was degassed with N$_2$ for 10 min and heated at 80° C. for 30 min. Then the reaction mixture was cooled to rt, diluted with DCM (100 mL)/water (100 mL) and stirred for 30 minutes. The organic layer was separated and aqueous layer was re-extracted with DCM (2×50 mL). Combined organic extracts were washed with water, brine, dried over sodium sulphate and concentrated. The crude residue was purified by flash chromatography (0-15% MeOH in DCM) to afford N-((3S,4S,5R)-5-(4-(3-fluorophenyl)-1H-1,2,3-triazol-1-yl)-4-hydroxytetrahydro-2H-pyran-3-yl)-N-methyl-4-nitrobenzenesulfonamide (2.1 g, 4.40 mmol, 71%) as an off-white solid. LC-MS, [M+H]$^+$=478.2, {Method C: t$_R$=2.453 min}.

Step-6: Synthesis of (3R,4R,5S)-3-(4-(3-fluorophenyl)-1H-1,2,3-triazol-1-yl)-5-(methylamino)tetrahydro-2H-pyran-4-ol: To a solution of N-((3S,4S,5R)-5-(4-(3-fluorophenyl)-1H-1,2,3-triazol-1-yl)-4-hydroxytetrahydro-2H-pyran-3-yl)-N-methyl-4-nitrobenzenesulfonamide (1 g, 2.094 mmol) in acetone (10 mL), potassium carbonate (0.868 g, 6.28 mmol) and benzenethiol (0.346 g, 3.14 mmol) were added sequentially at rt and stirred for 16 h. Then, the solvent was removed under reduced pressure to give crude residue which was purified by flash chromatography (0-20% MeOH(10% ammonia)/DCM) to afford (3R,4R,5S)-3-(4-(3-fluorophenyl)-1H-1,2,3-triazol-1-yl)-5-(methylamino)tetrahydro-2H-pyran-4-ol as a racemic mixture. The racemic mixture was further purified by SFC to separate the enantiomers.

Preparative Chiral HPLC Conditions:
 Preparative Column: Chiralpak IA (250×30)mm, 5 um
 BPR pressure: 100 bars
 Temperature: 25° C.
 Flow rate: 60 g/min
 Mobile Phase: CO$_2$/0.2% DEA in MeOH (70/30)
 Detector Wavelength: 245 nm
 Sample preparation: 10 mg/1 mL MeOH:
Analytical Chiral HPLC Conditions:
 Analytical Column: Chiralpak IA (250×30)mm, 5 um
 BPR pressure: 100 bars
 Temperature: 30° C.
 Flow rate: 3 g/min
 Mobile Phase: CO$_2$/0.2% DEA in MeOH (70/30)
 Detector Wavelength: UV 200-400 nm
 Enantiomer 1 (undesired): 0.15 g: chiral HPLC t$_R$=3.63 min; LC-MS, [M+H]$^+$=293.2, {Method C: t$_R$=0.934 min};
 Enantiomer 2 (desired): 0.18 g: chiral HPLC t$_R$=5.77 min; LC-MS, [M+H]$^+$=293.1, {Method C: t$_R$=0.941 min}.

Step-7: To a stirred solution of (4aR,6R,7R,8R,8aR)-8-(4-(3-fluorophenyl)-1H-1,2,3-triazol-1-yl)-7-methoxy-2-phenylhexahydropyrano[3,2-d][1,3]dioxine-6-carboxylic acid (200 mg, 0.439 mmol) in DMF (5 mL), HATU (334 mg, 0.878 mmol), DIPEA (0.767 mL, 4.39 mmol) and (3R,4R, 5S)-3-(4-(3-fluorophenyl)-1H-1,2,3-triazol-1-yl) (methylamino)tetrahydro-2H-pyran-4-ol Enantiomer 2 (128 mg, 0.439 mmol) were added sequentially at rt and stirred for 16 h. The reaction mixture was poured into ice cold water (100 mL) and stirred for 10 min. The obtained solid was filtered and dried to afford crude residue which was further purified by flash chromatography (0-10% MeOH in DCM) to afford (4aR,6R,7R,8R,8aR)-8-(4-(3-fluorophenyl)-1H-1,2,3-triazol-1-yl)-N-((3S,4R,5R)-5-(4-(3-fluorophenyl)-1H-1,2,3-triazol-1-yl)-4-hydroxytetrahydro-2H-pyran-3-yl)-7-methoxy-N-methyl-2-phenylhexahydropyrano[3,2-d][1,3]dioxine-6-carboxamide (0.195 g, 0.259 mmol, 59%) as an off-white solid. LC-MS, [M+H]$^+$=730.2, {Method C: t$_R$=3.051 min};

Step-8: (4aR,6R,7R,8R,8aR)-8-(4-(3-fluorophenyl)-1H-1,2,3-triazol-1-yl)-N-((3S,4R,5R)-5-(4-(3-fluorophenyl)-1H-1,2,3-triazol-1-yl)-4-hydroxytetrahydro-2H-pyran-3-yl)-7-methoxy-N-methyl-2-phenylhexahydropyrano[3,2-d]

[1,3]dioxine-6-carboxamide (195 mg, 0.267 mmol) was suspended in 70% Aqueous AcOH (10 mL) and heated at 70° C. for 16 h. Then reaction mixture was cooled to rt and solvent was removed under reduced pressure to give crude residue. The crude residue was purified by Prep-HPLC Method B to afford Example 21: (2R,3R,4S,5R,6R)-4-(4-(3-fluorophenyl)-1H-1,2,3-triazol-1-yl)-N-((3S,4R,5R)-5-(4-(3-fluorophenyl)-1H-1,2,3-triazol-1-yl)-4-hydroxytetrahydro-2H-pyran-3-yl)-5-hydroxy-6-(hydroxymethyl)-3-methoxy-N-methyltetrahydro-2H-pyran-2-carboxamide (0.095 g, 0.148 mmol, 55%) as an off-white solid. LC-MS, [M+H]$^+$=642.2, {Method C: t$_R$=1.95}. $^1$H NMR (400 MHz, MEOH-d$_4$) δ ppm 8.70 (d, J=8.5 Hz, 1H), 8.49 (d, J=8.0 Hz, 1H), 7.57-7.71 (m, 4H), 7.43-7.49 (m, 2H), 7.06-7.12 (m, 2H), 4.98 (br d, J=8.0 Hz, 1H), 4.62-4.78 (m, 1H), 4.41-4.60 (m, 3H), 4.06-4.26 (m, 3H), 3.65-4.01 (m, 6H), 2.99-3.26 (m, 6H) [*rotameric mixture]; hGal3 IC$_{50}$=0.03 μM.

EXAMPLE 22

Synthesis of (2R,3R,4S,5R,6R)-N-((3S,4R,5R)-5-(5-fluoro-1H-pyrazolo[3,4-b]pyridin-1-yl)-4-hydroxytetrahydro-2H-pyran-3-yl)-4-(4-(3-fluorophenyl)-1H-1,2,3-triazol-1-yl)-5-hydroxy-6-(hydroxymethyl)-3-methoxy-N-methyltetrahydro-2H-pyran-2-carboxamide (Isomer 1 and 2)

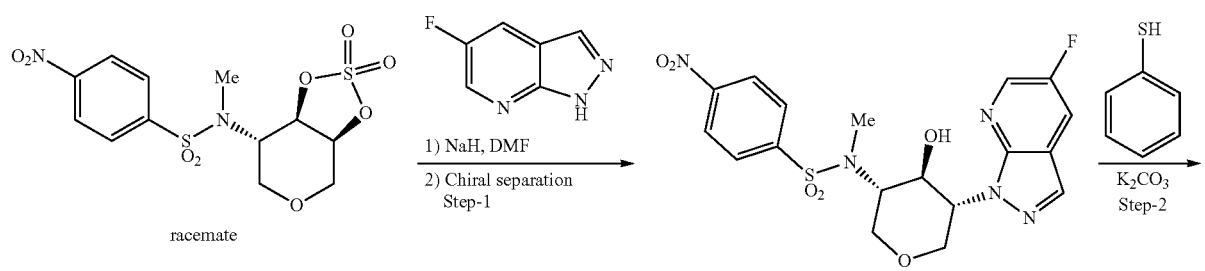

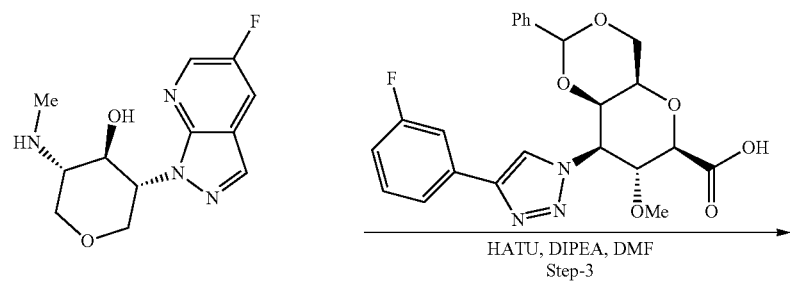

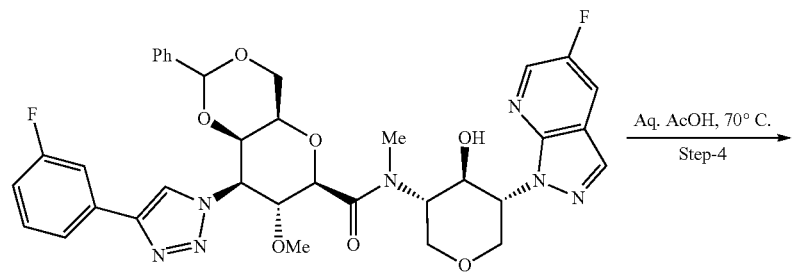

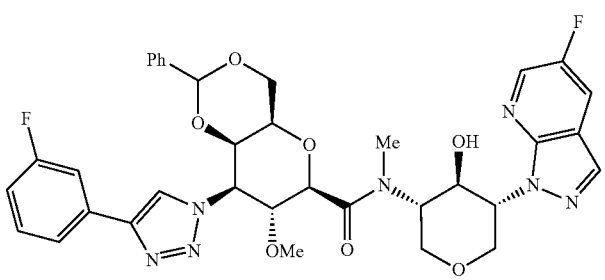

Example 22a & 22b

Step-1: To a stirred solution of 5-fluoro-1H-pyrazolo[3,4-b]pyridine (67.8 mg, 0.494 mmol) in THF (3 mL), 18-crown-6 (171 mg, 0.647 mmol) and NaH (25.9 mg, 0.647 mmol, 60% w/w) were added at rt and refluxed at 80° C. for 10 min. Then N-((3aS,7S,7aR)-2,2-dioxidotetrahydro-3aH-[1,3,2]dioxathiolo[4,5-c]pyran-7-yl)-N-methyl-4-nitrobenzenesulfonamide (150 mg, 0.380 mmol) in THF (3 mL) was added dropwise over a period of 5 min and refluxed at 80° C. for 16 h. Reaction mixture was cooled to 0° C., acidified with con.HCl (around pH=1) and further refluxed at 80° C. for 2 h. The reaction mixture was cooled to rt, neutralized with aq. 10% NaHCO3 solution and extracted with EtOAc (2×25 mL). The combined organic extracts were washed with water, brine, dried over sodium sulphate and concentrated. The crude residue was purified by flash chromatography (60-80% EtOAc in n-hexane) to afford N-((3S,4S,5R)-5-(5-fluoro-1H-pyrazolo[3,4-b]pyridin-1-yl)-4-hydroxytetrahydro-2H-pyran-3-yl)-N-methyl-4-nitrobenzenesulfonamide as a racemate. The racemate was further purified by chiral SFC to afford pure enantiomer-1 and enantiomer-2.
Preparative Chiral HPLC Conditions:
 Preparative Column: Chiralpak ADH (250×30)mm, 5 um
 BPR pressure: 100 bars
 Temperature: 25° C.
 Flow rate: 60 g/min
 Mobile Phase: $CO_2$/0.4% DEA in EtOH (60/40)
 Detector Wavelength: 245 nm
 Sample preparation: 10 mg/1 mL MeOH:
Analytical Chiral HPLC Conditions:
 Analytical Column: Chiralpak ADH (250×4.6)mm, 5 um
 BPR pressure: 100 bars
 Temperature: 25° C.
 Flow rate: 3 g/min
 Mobile Phase: $CO_2$/0.4% DEA in EtOH (60/40)
 Detector Wavelength: UV 200-400 nm
 Enantiomer 1: (50 mg, 0.111 mmol, 29.1% yield); chiral HPLC $t_R$=5.59 min; LC-MS, [M+H]$^+$=452.2, {Method C: $t_R$=2.352 min};
 Enantiomer 2: (50 mg, 0.111 mmol, 29.1% yield); chiral HPLC $t_R$=8.23 min; LC-MS, [M+H]$^+$=452.2, {Method C: $t_R$=2.353 min}.
Step-2: To a stirred solution of N-((3S,4S,5R)-5-(5-fluoro-1H-pyrazolo[3,4-b]pyridin-1-yl)-4-hydroxytetrahydro-2H-pyran-3-yl)-N-methyl-4-nitrobenzenesulfonamide Enantiomer 1 (50 mg, 0.111 mmol) in acetone (2 mL) was added $K_2CO_3$ (45.9 mg, 0.332 mmol) followed by thiophenol (0.031 mL, 0.299 mmol) at rt and stirred for 2 h. Then the solvent was removed under reduced pressure to give crude residue and the crude was purified by flash chromatography (5-15% MeOH(5% aq.NH3) in CHCl$_3$) to afford (3R,4R,5S)-3-(5-fluoro-1H-pyrazolo[3,4-b]pyridin-1-yl)-5-(methylamino)tetrahydro-2H-pyran-4-ol (20 mg, 0.075 mmol, 68%). LC-MS, [M+H]$^+$=267.2, {Method D: $t_R$=0.57 min}.
Step-3: To a stirred solution of (4aR,6R,7R,8R,8aR)-8-(4-(3-fluorophenyl)-1H-1,2,3-triazol-1-yl)-7-methoxy-2-phenylhexahydropyrano[3,2-d][1,3]dioxine-6-carboxylic acid (25 mg, 0.055 mmol) and (3R,4R,5S)-3-(5-fluoro-1H-pyrazolo[3,4-b]pyridin-1-yl)-5-(methylamino)tetrahydro-2H-pyran-4-ol (14.62 mg, 0.055 mmol) in DMF (0.6 mL), DIPEA (0.048 mL, 0.274 mmol) and HATU (31.3 mg, 0.082 mmol) were added sequentially at rt and stirred for 16 h. Then the reaction mixture was diluted with 20 mL of ice cold water and stirred for 10 min. The obtained solid was filtered and dried to afford (4aR,6R,7R,8R,8aR)-N-((3S,4R,5R)-5-(5-fluoro-1H-pyrazolo[3,4-b]pyridin-1-yl)-4-hydroxytetrahydro-2H-pyran-3-yl)-8-(4-(3-fluorophenyl)-1H-1,2,3-triazol-1-yl)-7-methoxy-N-methyl-2-phenylhexahydropyrano[3,2-d][1,3]dioxine-6-carboxamide (25 mg, 0.036 mmol, 65%). LC-MS, [M+H]$^+$=704.4, {Method D: $t_R$=1.28 min}.

Step-4: (4aR,6R,7R,8R,8aR)-N-((3S,4R,5R)-5-(5-fluoro-1H-pyrazolo[3,4-b]pyridin-1-yl)-4-hydroxytetrahydro-2H-pyran-3-yl)-8-(4-(3-fluorophenyl)-1H-1,2,3-triazol-1-yl)-7-methoxy-N-methyl-2-phenylhexahydropyrano[3,2-d][1,3]dioxine-6-carboxamide (30 mg, 0.043 mmol) was suspended in 70% aq.AcOH (10 mL) and heated at 75° C. for 16 h. Reaction mixture was cooled to rt and purified by prep-HPLC Method A to afford Example 22a: (2R,3R,4S,5R,6R)-N-((3S,4R,5R)-5-(5-fluoro-1H-pyrazolo[3,4-b]pyridin-1-yl)-4-hydroxytetrahydro-2H-pyran-3-yl)-4-(4-(3-fluorophenyl)-1H-1,2,3-triazol-1-yl)-5-hydroxy-6-(hydroxymethyl)-3-methoxy-N-methyltetrahydro-2H-pyran-2-carboxamide Isomer 1 (13.4 mg, 0.022 mmol, 51%). LC-MS, [M+H]$^+$=616.1, {Method A: $t_R$=1.54 min}. $^1$H NMR (400 MHz, MEOH-d$_4$) δ=8.71 (d, J=7.0 Hz, 1H), 8.52 (dt, J=6.5, 2.0 Hz, 1H), 8.15 (d, J=3.0 Hz, 1H), 7.97 (dt, J=8.4, 3.1 Hz, 1H), 7.70 (d, J=8.0 Hz, 1H), 7.67-7.60 (m, 1H), 7.47 (td, J=7.9, 5.8 Hz, 1H), 7.09 (td, J=8.5, 2.5 Hz, 1H), 5.16-4.95 (m, 2H), 4.79-4.65 (m, 1H), 4.58-4.51 (m, 1H), 4.46-4.41 (m, 1H), 4.25-4.13 (m, 2H), 4.09-3.88 (m, 3H), 3.88-3.65 (m, 4H), 3.26 (s, 1H), 3.12 (s, 2H), 3.09 (s, 2H), 3.01 (s, 1H). hGal3 IC$_{50}$=>10 μM.

EXAMPLE 22b

Prepared in a similar fashion as described for Example 22a, by using enantiomer 2 in Step-2 as the starting material. LC-MS, [M+H]+=616.1, {Method A: $t_R$=1.54 min}. $^1$H NMR (400 MHz, MEOH-d$_4$) δ ppm 8.67-8.75 (m, 1H), 8.39-8.53 (m, 1H), 8.13-8.22 (m, 1H), 7.98 (d, J=2.5 Hz, 1H), 7.38-7.80 (m, 3H), 7.02-7.17 (m, 1H), 5.18-5.32 (m, 1H), 4.92-5.12 (m, 2H), 4.71-4.82 (m, 2H), 4.38-4.49 (m, 1H), 3.66-4.15 (m, 8H), 3.27 (s, 1H), 3.09-3.12 (m, 3H), 3.04 (s, 2H) (rotameric mixture). hGal3 IC$_{50}$=0.04.

We claim:
1. A compound of Formula (I) or Formula (II):

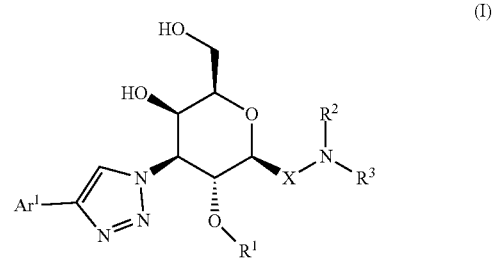

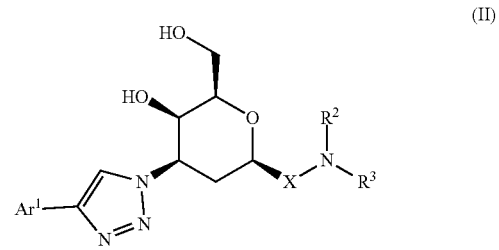

or a pharmaceutically acceptable salt thereof, wherein:
X is independently selected from —C(O)—, —CH$_2$—, and —CH$_2$C(O)—;

Ar$^1$ is independently phenyl or naphthyl; and wherein each ring moiety is substituted with 1 to 5 substituents selected from cyano, halogen, C$_{1-4}$ alkyl, C$_{1-4}$ alkoxy, C$_{1-4}$ haloalkyl, and C$_{1-4}$ haloalkoxy;

R$^1$ is independently selected from H, C$_{1-4}$ alkyl, C$_{1-4}$ haloalkyl, and —CH$_2$C(O)OH;

R$^2$ is independently selected from H, C$_{1-4}$ alkyl substituted with 0 to 1 OH, C$_{1-4}$ haloalkyl, —(CH$_2$)$_{0-2}$—C$_{3-6}$ cycloalkyl, and —(CH$_2$)$_{0-2}$-phenyl substituted with 0 to 3 halogen;

R$^3$ is independently C$_{3-6}$ cycloalkyl or heterocycloalkyl including from 4 to 7 ring atoms, wherein from 1 to 2 ring atoms are each independently selected from N(, N(R$^B$), and O, and S; wherein said ring moiety is substituted with 0 to 1 R$^5$ and 1 R$^{5A}$;

R$^5$ is independently OH, cyano, halogen, C$_{1-4}$ haloalkyl, C$_{1-4}$ alkoxy, C$_{1-4}$ haloalkoxy, and C$_{1-4}$ alkyl substituted with 0 to 1 OH;

R$^{5A}$ is independently selected from

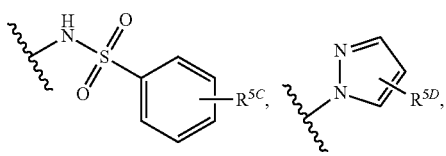

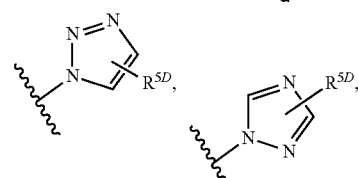

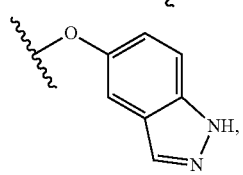

a bicyclic ring selected from

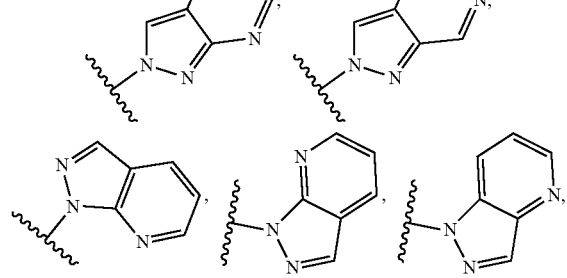

and 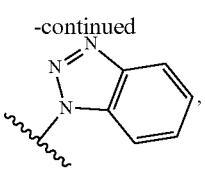, wherein said bicyclic ring is substituted 0 to 2 R$^{5C}$;

R$^{5B}$ is independently

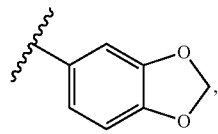 [SMILES: *c1ccc2c(c1)OCO2]

or phenyl substituted with 0 to 2 substituents selected from cyano, halogen, halogen, C$_{1-4}$ alkyl, C$_{1-4}$ alkoxy, C$_{1-4}$ haloalkyl, C$_{1-4}$ haloalkoxy;

R$^{5C}$ is independently selected from: cyano, halogen, C$_{1-4}$ alkyl, C$_{1-4}$ alkoxy, C$_{1-4}$ haloalkyl, and C$_{1-4}$ haloalkoxy;

R$^{5D}$ is independently selected from R$^{5C}$

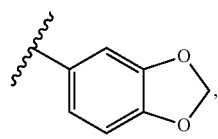

phenyl, naphthyl, pyridinyl, and primidinyl, wherein each ring moiety is substituted with 0 to 2 substituents selected from cyano, halogen, C$_{1-4}$ alkyl, C$_{1-4}$ alkoxy, C$_{1-4}$ haloalkyl, C$_{1-4}$ haloalkoxy;

R$^{5E}$ is independently selected from: H, C$_{1-4}$ alkyl, Bn, —C(O)(C$_{1-4}$ alkyl), —C(O)O(C$_{1-4}$ alkyl), and

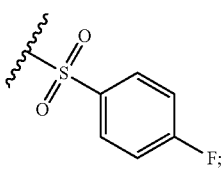

and

R$^{5F}$ is independently —NH-phenyl, wherein said phenyl is substituted with 0 to 2 substituents selected from cyano, halogen, halogen, C$_{1-4}$ alkyl, C$_{1-4}$ alkoxy, C$_{1-4}$ haloalkyl, C$_{1-4}$ haloalkoxy.

2. The compound of claim 1, wherein:

X is —C(O)—; and Ar$^1$ is phenyl substituted with 1 to 3 halogen.

3. The compound of claim 2, wherein:

R$^3$ is independently C$_{5-6}$ cycloalkyl or heterocycloalkyl including from 4 to 6 ring atoms, wherein from 1 to 2 ring atoms are each independently selected from N(R$^B$), N(R$^E$), and O; wherein each said ring moiety is substituted with 0 to 1 R$^5$ and 1 R$^{5A}$.

4. A compound of claim 3, wherein:
$R^3$ is independently selected from:

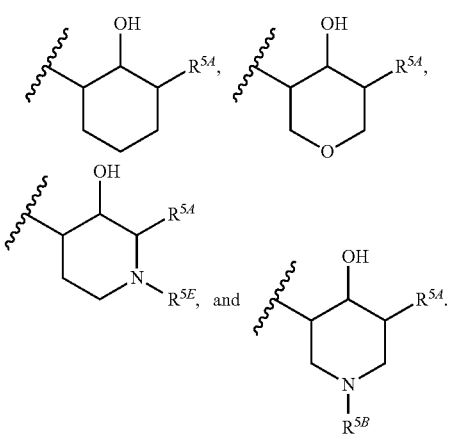

5. A compound of claim 4, wherein:

$R^1$ is independently H or $CH_3$; and $R^2$ is independently selected from: H, $CH_3$, —$CH_2CH_3$, —$CH_2CH_2OH$, —$CH_2CHF_2$, cyclopropyl and cyclopryopylmethyl.

6. A compound of claim 3, wherein:

$R^1$ is independently H or $C_{1-4}$ alkyl; and $R^2$ is independently selected from H, $C_{1-4}$ alkyl substituted with 0 to 1 OH, $C_{1-4}$ haloalkyl, —$(CH_2)_{0-1}$-cyclopropyl, and —$CH_2$-(phenyl substituted with 0 to 2 halogen).

7. A compound of claim 1, wherein the compound is selected from;

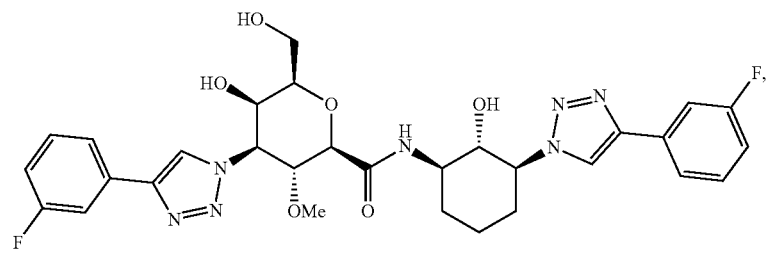

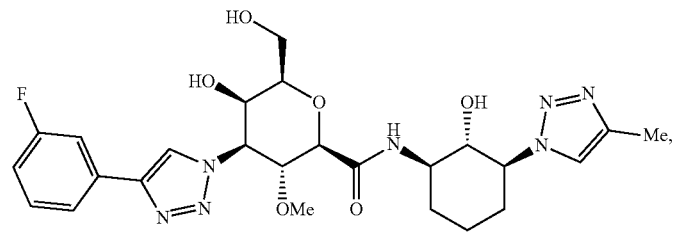 [SMILES: CO[C@@H]1[C@@H](n2cc(-c3cccc(F)c3)nn2)[C@@H](O)[C@@H](CO)O[C@H]1C(=O)N[C@@H]1CCC[C@H](n2cc(C)nn2)[C@H]1O]

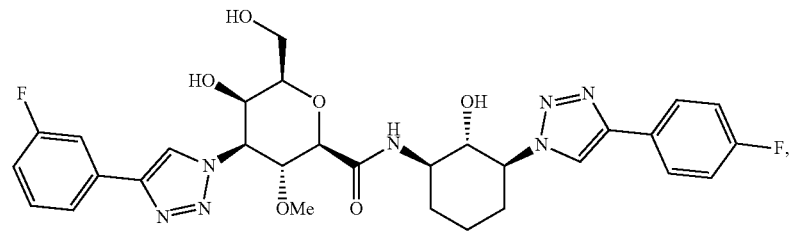 [SMILES: CO[C@@H]1[C@@H](n2cc(-c3cccc(F)c3)nn2)[C@@H](O)[C@@H](CO)O[C@H]1C(=O)N[C@@H]1CCC[C@H](n2cc(-c3ccc(F)cc3)nn2)[C@H]1O]

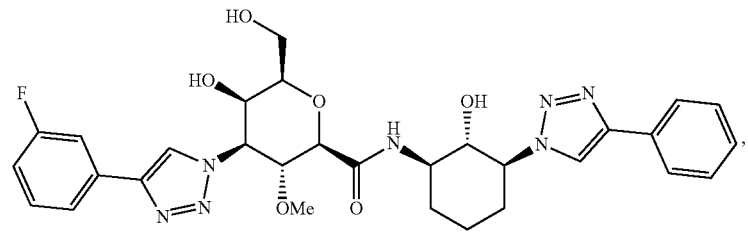

-continued
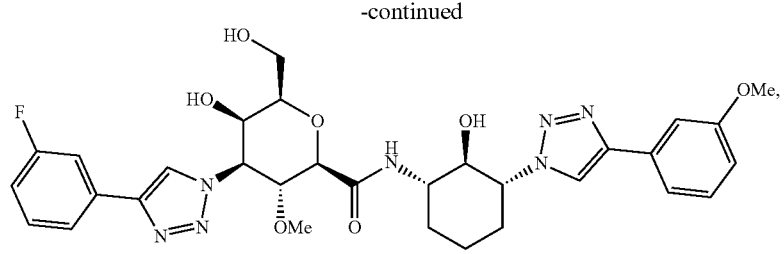
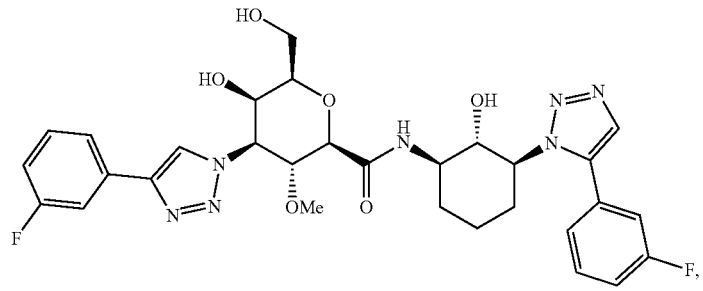
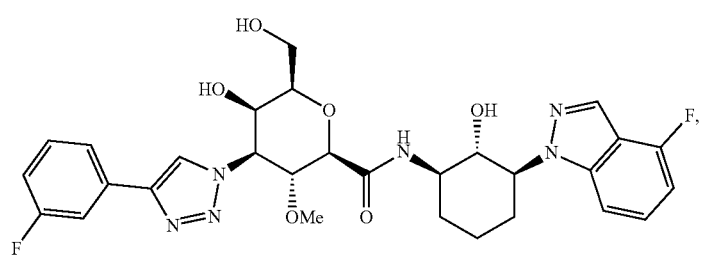
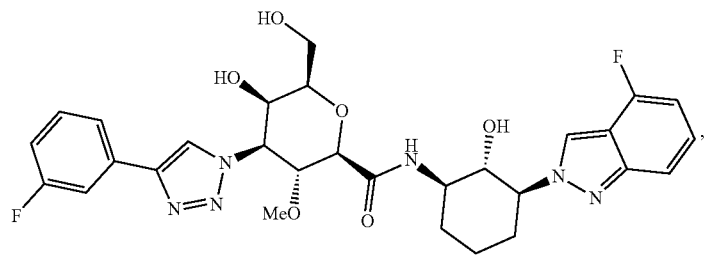
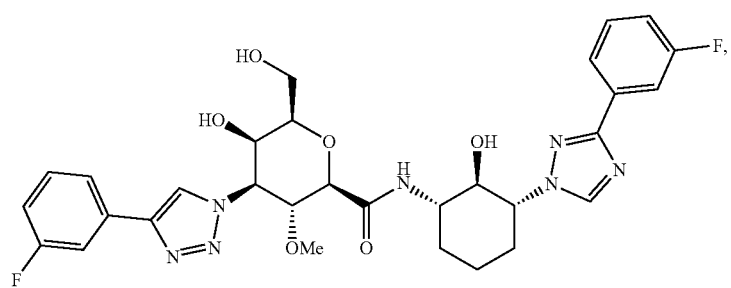
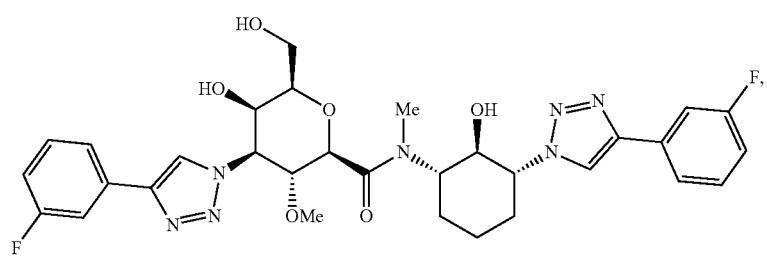

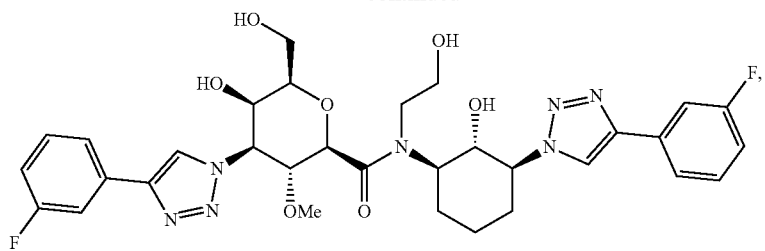 [SMILES: CO[C@@H]1[C@@H](n2cc(-c3cccc(F)c3)nn2)[C@@H](O)[C@@H](CO)O[C@H]1C(=O)N(CCO)[C@@H]1CCC[C@H](n2cc(-c3cccc(F)c3)nn2)[C@H]1O]
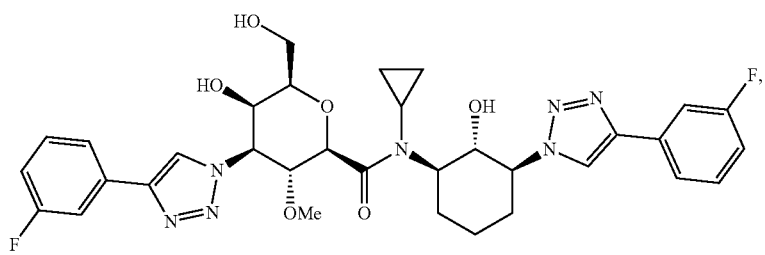 [SMILES: CO[C@@H]1[C@@H](n2cc(-c3cccc(F)c3)nn2)[C@@H](O)[C@@H](CO)O[C@H]1C(=O)N(C1CC1)[C@@H]1CCC[C@H](n2cc(-c3cccc(F)c3)nn2)[C@H]1O]
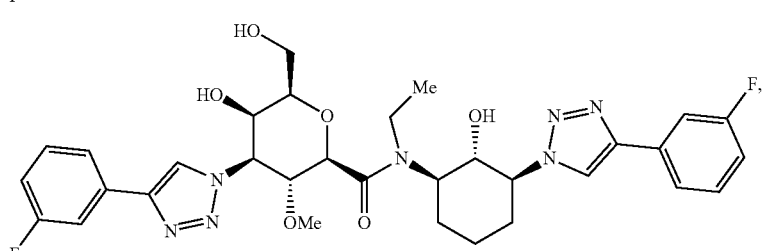
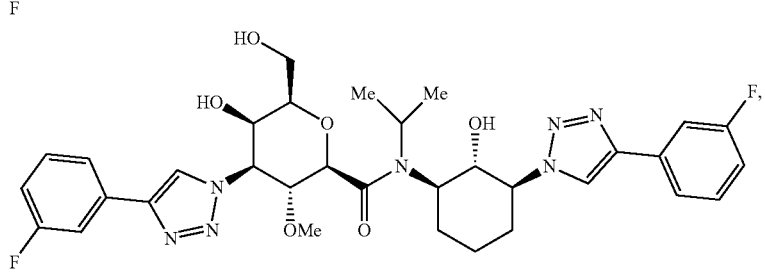
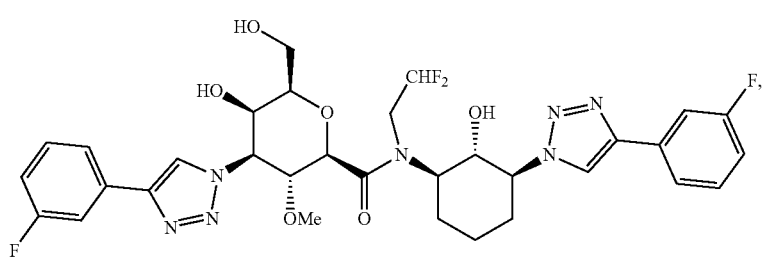 [SMILES: CO[C@@H]1[C@@H](n2cc(-c3cccc(F)c3)nn2)[C@@H](O)[C@@H](CO)O[C@H]1C(=O)N(CC(F)F)[C@@H]1CCC[C@H](n2cc(-c3cccc(F)c3)nn2)[C@H]1O]
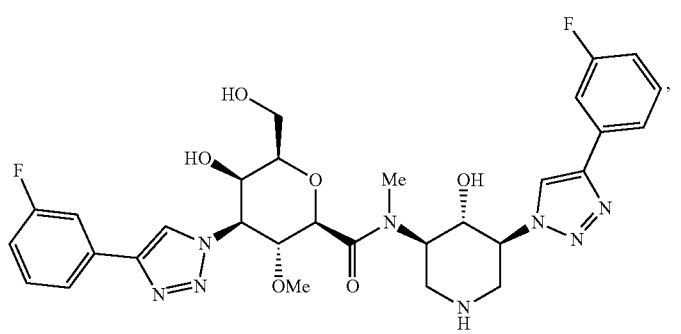

-continued
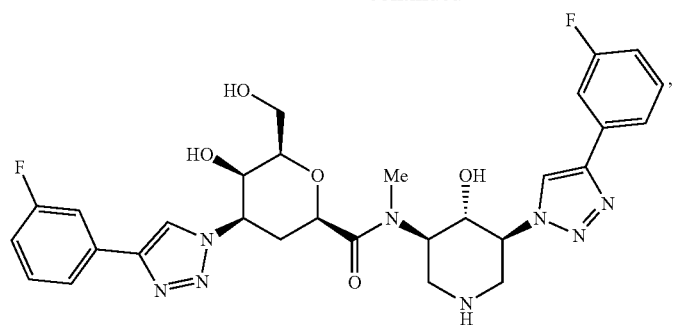
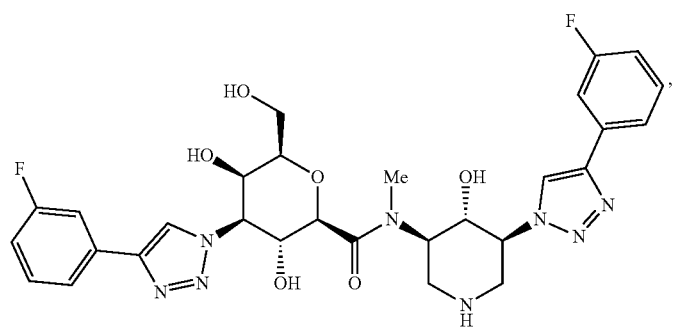
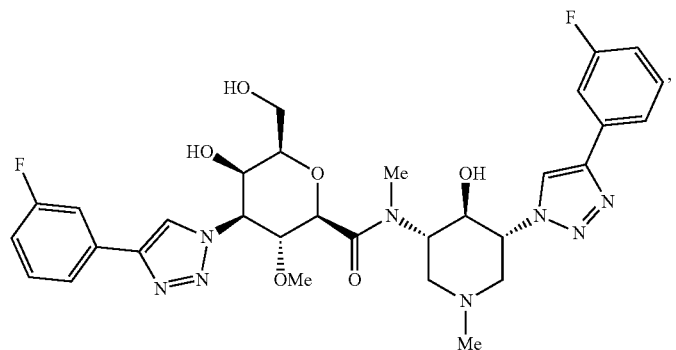
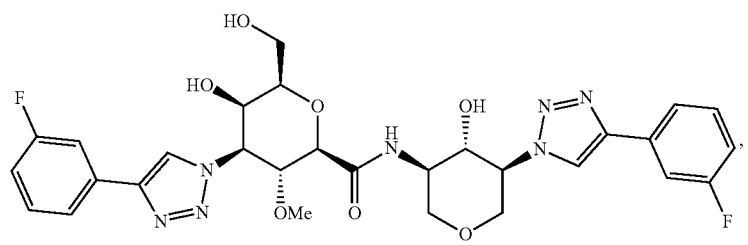
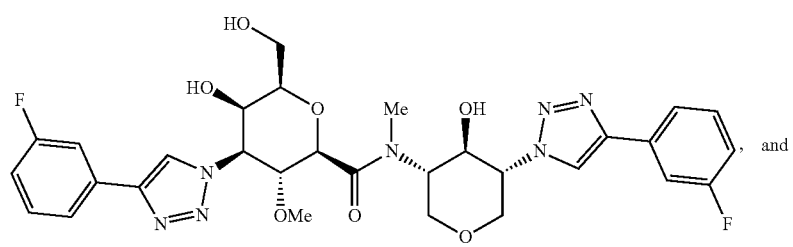, and

-continued

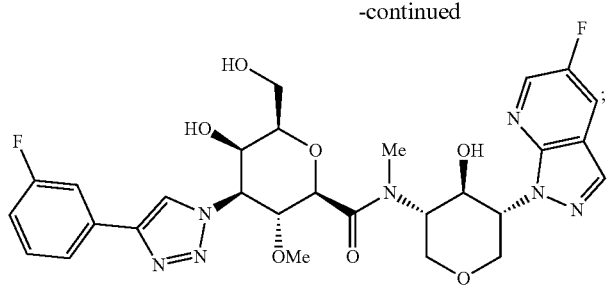

or a pharmaceutically acceptable salt thereof.

8. A composition comprising a therapeutically effective amount of a compound of claim 1, or a pharmaceutically acceptable salt thereof, and a pharmaceutically acceptable carrier.

9. A method for treating fibrosis of organs selected from liver, kidney, lung, heart and skin; liver diseases and conditions selected from acute hepatitis, chronic hepatitis, liver fibrosis, liver cirrhosis, portal hypertension, regenerative failure, non-alcoholic steatohepatitis (NASH), liver hypofunction, and hepatic blood flow disorder; cell proliferative diseases, cancers, and conditions selected from solid tumor, solid tumor metastasis, vascular fibroma, myeloma, multiple myeloma, Kaposi's sarcoma, leukemia, chronic lymphocytic leukemia (CLL)) and invasive metastasis of cancer cell; inflammatory diseases and conditions selected from psoriasis, nephropathy, and pneumonia; gastrointestinal tract diseases and conditions selected from irritable bowel syndrome (IBS), inflammatory bowel disease (IBD), and abnormal pancreatic secretion; renal diseases and conditions, urinary tract-associated diseases and conditions selected from benign prostatic hyperplasia or symptoms associated with neuropathic bladder disease, spinal cord tumor, hernia of intervertebral disk, spinal canal stenosis, and symptoms derived from diabetes; lower urinary tract diseases and conditions of obstruction of lower urinary tract; inflammatory diseases and conditions of lower urinary tract selected from dysuria and frequent urination; pancreatic diseases and conditions, abnormal angiogenesis-associated diseases and conditions of arterial obstruction; scleroderma, brain-associated diseases and conditions selected from cerebral infarction and cerebral hemorrhage; neuropathic pain and peripheral neuropathy, ocular diseases and conditions selected from age-related macular degeneration (AMD), diabetic retinopathy, proliferative vitreoretinopathy (PVR), cicatricial pemphigoid, and glaucoma filtration surgery scarring; comprising administering a therapeutically effective amount of a compound or a pharmaceutically acceptable salt thereof of claim 1 to a patient.

10. A method for treating a disease or condition selected from renal fibrosis, pulmonary fibrosis, hepatic fibrosis, arterial fibrosis, and systemic sclerosis; comprising administering a therapeutically effective amount of a compound of claim 1, or a pharmaceutically acceptable salt thereof of to a patient.

11. A composition comprising a therapeutically effective amount of a compound or a pharmaceutically acceptable salt thereof of claim 7, and one or more pharmaceutically acceptable carriers.

12. A method for treating fibrosis of organs selected from liver, kidney, lung, heart and skin; liver diseases and conditions selected from acute hepatitis, chronic hepatitis, liver fibrosis, liver cirrhosis, portal hypertension, regenerative failure, non-alcoholic steatohepatitis (NASH), liver hypofunction, and hepatic blood flow disorder; cell proliferative diseases, cancers, and conditions selected from solid tumor, solid tumor metastasis, vascular fibroma, myeloma, multiple myeloma, Kaposi's sarcoma, leukemia, chronic lymphocytic leukemia (CLL)) and invasive metastasis of cancer cell; inflammatory diseases and conditions selected from psoriasis, nephropathy, and pneumonia; gastrointestinal tract diseases and conditions selected from irritable bowel syndrome (IBS), inflammatory bowel disease (IBD), and abnormal pancreatic secretion; renal diseases and conditions, urinary tract-associated diseases and conditions selected from benign prostatic hyperplasia or symptoms associated with neuropathic bladder disease, spinal cord tumor, hernia of intervertebral disk, spinal canal stenosis, and symptoms derived from diabetes; lower urinary tract diseases and conditions of obstruction of lower urinary tract; inflammatory diseases and conditions of lower urinary tract selected from dysuria and frequent urination; pancreatic diseases and conditions, abnormal angiogenesis-associated diseases and conditions of arterial obstruction; scleroderma, brain-associated diseases and conditions selected from cerebral infarction and cerebral hemorrhage; neuropathic pain and peripheral neuropathy, ocular diseases and conditions selected from age-related macular degeneration (AMD), diabetic retinopathy, proliferative vitreoretinopathy (PVR), cicatricial pemphigoid, and glaucoma filtration surgery scarring; comprising administering a therapeutically effective amount of a compound or a pharmaceutically acceptable salt thereof of claim 9 to a patient.

13. A method for treating a disease or condition selected from renal fibrosis, pulmonary fibrosis, hepatic fibrosis, arterial fibrosis, and systemic sclerosis; comprising administering a therapeutically effective amount of a compound of claim 7, or a pharmaceutically acceptable salt thereof of to a patient.

* * * * *